US008236498B2

(12) United States Patent
Tanabe et al.

(10) Patent No.: US 8,236,498 B2
(45) Date of Patent: Aug. 7, 2012

(54) METHOD OF DETECTING NUCLEOTIDE SEQUENCE WITH AN INTRAMOLECULAR PROBE

(75) Inventors: Tetsuya Tanabe, Tokyo (JP); Nobuhiko Morimoto, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 12/172,655

(22) Filed: Jul. 14, 2008

(65) Prior Publication Data

US 2009/0004666 A1 Jan. 1, 2009

Related U.S. Application Data

(63) Continuation of application No. PCT/JP2007/050835, filed on Jan. 19, 2007.

(30) Foreign Application Priority Data

| Jan. 20, 2006 | (JP) | 2006-013066 |
| Dec. 27, 2006 | (JP) | 2006-353310 |
| Dec. 27, 2006 | (JP) | 2006-353311 |

(51) Int. Cl.
*C12Q 1/68* (2006.01)
*C12P 19/34* (2006.01)
*C07H 21/02* (2006.01)
*C07H 21/04* (2006.01)

(52) U.S. Cl. ....... 435/6.1; 435/91.2; 536/23.1; 536/24.3

(58) Field of Classification Search ............ 435/6, 91.2, 435/6.1; 536/23.1, 24.3
See application file for complete search history.

(56) References Cited

U.S. PATENT DOCUMENTS

| 4,988,617 | A | * | 1/1991 | Landegren et al. | 435/6 |
| 5,356,776 | A | * | 10/1994 | Kambara et al. | 435/6.12 |
| 5,525,462 | A | * | 6/1996 | Takarada et al. | 435/6.18 |
| 5,683,985 | A | * | 11/1997 | Chu et al. | 514/44 A |
| 5,720,928 | A | * | 2/1998 | Schwartz | 422/186 |
| 5,780,613 | A | * | 7/1998 | Letsinger et al. | 536/25.33 |
| 5,872,105 | A | * | 2/1999 | Kool | 514/44 R |
| 5,942,391 | A | * | 8/1999 | Zhang et al. | 435/6 |
| 6,235,472 | B1 | * | 5/2001 | Landegren et al. | 435/6 |
| 7,563,572 | B2 | * | 7/2009 | Pont-Kingdon et al. | 435/6 |
| 2002/0081598 | A1 | * | 6/2002 | Evans et al. | 435/6 |
| 2003/0113724 | A1 | * | 6/2003 | Schembri et al. | 435/6 |
| 2003/0124544 | A1 | | 7/2003 | Kambara et al. | |
| 2003/0157483 | A1 | * | 8/2003 | Sorge et al. | 435/6 |
| 2004/0086892 | A1 | | 5/2004 | Crothers et al. | |
| 2005/0118616 | A1 | | 6/2005 | Kawashima et al. | |
| 2008/0305486 | A1 | * | 12/2008 | Tan et al. | 435/6 |
| 2009/0004666 | A1 | * | 1/2009 | Tanabe et al. | 435/6 |

FOREIGN PATENT DOCUMENTS

| JP | 9-220099 | 8/1997 |
| JP | 9-509063 | 9/1997 |
| JP | 2000-511060 | 8/2000 |
| JP | 3085409 | 9/2000 |
| JP | 2004-528016 | 9/2004 |
| JP | 3590633 | 11/2004 |
| JP | 2005-143492 | 6/2005 |
| JP | 3753942 | 12/2005 |
| JP | 2006-510372 | 3/2006 |
| WO | WO 97/19193 | 5/1997 |
| WO | WO 97/45559 | 12/1997 |
| WO | WO 98/04746 | 2/1998 |
| WO | WO 99/18241 | 4/1999 |
| WO | WO 00/04193 | 1/2000 |
| WO | WO00/28082 | 5/2000 |
| WO | WO 02/057491 | 7/2002 |
| WO | WO 02/077256 A1 | 10/2002 |
| WO | WO 03/002762 A2 | 1/2003 |
| WO | WO 2004/057017 A2 | 7/2004 |
| WO | WO 2005/079462 A2 | 9/2005 |
| WO | WO 2005/092038 A2 | 10/2005 |
| WO | WO 2006/019155 A1 | 2/2006 |

OTHER PUBLICATIONS

Collins et al., Directional cloning of DNA fragments at a large distance from an initial probe : A circularization method. PNAS 81 (21) : 6812-6816 (1984).*
Perkin-Elmer Cetus GeneAmp DNA amplification Reagent kit 2 pages (1988).*
Chu et al., The stability of different forms of double-stranded decoy DNA in serum and nuclear extracts. Nucleic Acids Research 20 (21) : 5857-5858 (1992).*
Clusel et al., Ex vivo regulation of specific gene expression by nanomolar concentration of double-stranded dumbbell oligonucleotides. Nucleic Acids Research 21(15) :3405-3411 (1993).*
Erie et al., A dumbbell-shaped, double-hairpin structure of DNA: a thermodynamic investigation. Biochemistry 26 : 7150-7159 (1987).*
SantaLucia J., A unified view of polymer, dumbbell, and oligonucleotide DNA nearest-neighbor thermodynamics. PNAS 95 : 1460-1465 (1998).*
Landegren U. et al., "A Ligase-Mediated Gene Detection Technique", *Science 241*:1077-1080 (1988).

(Continued)

*Primary Examiner* — Ethan C Whisenant
(74) *Attorney, Agent, or Firm* — Scully, Scott, Murphy & Presser, P.C.

(57) ABSTRACT

A nucleotide sequence-detecting method, including preparing a first intramolecular detecting sequence having a sequence complementary to a first sequence located at a 3'-side of the detecting site contained in the nucleotide sample and a second intramolecular detecting sequence having a sequence complementary to a second sequence located at a 5'-side of the detecting site, preparing a detecting chain containing a sequence of the detecting chain by connecting the first intramolecular detecting sequence to the 3' terminal of the nucleotide sample and the second intramolecular detecting sequence to the 5' terminal, allowing intramolecular hybridization at two positions of the detecting chain, connecting the 3' terminal of the first intramolecular detecting sequence to the 5' terminal of the second intramolecular detecting sequence, obtaining a cyclic structure, detecting the desired sequence in the nucleotide sample from the cyclic structure.

42 Claims, 25 Drawing Sheets

OTHER PUBLICATIONS

Hardenbol P. et al., "Highly Multiplexed Molecular Inversion Probe Genotyping: Over 10,000 Targeted SNPs Genotyped in a Single Tube Assay", *Genome Research 15*:269-275 (2006).

Hardenbol P. et al., "Multiplexed Genotyping With Sequence-Tagged Molecular Inversion Probes", *Nature Biotechnology 21*(6):673-678 (2003).

Notice of Reasons for Rejection dated Jan. 24, 2012 received from the Japanese Patent Office from related Japanese Patent Application No. 2007-554988, together with an English-language translation.

Official Action dated Mar. 1, 2011 received from the Japanese Patent Office, together with an English-language translation.

* cited by examiner

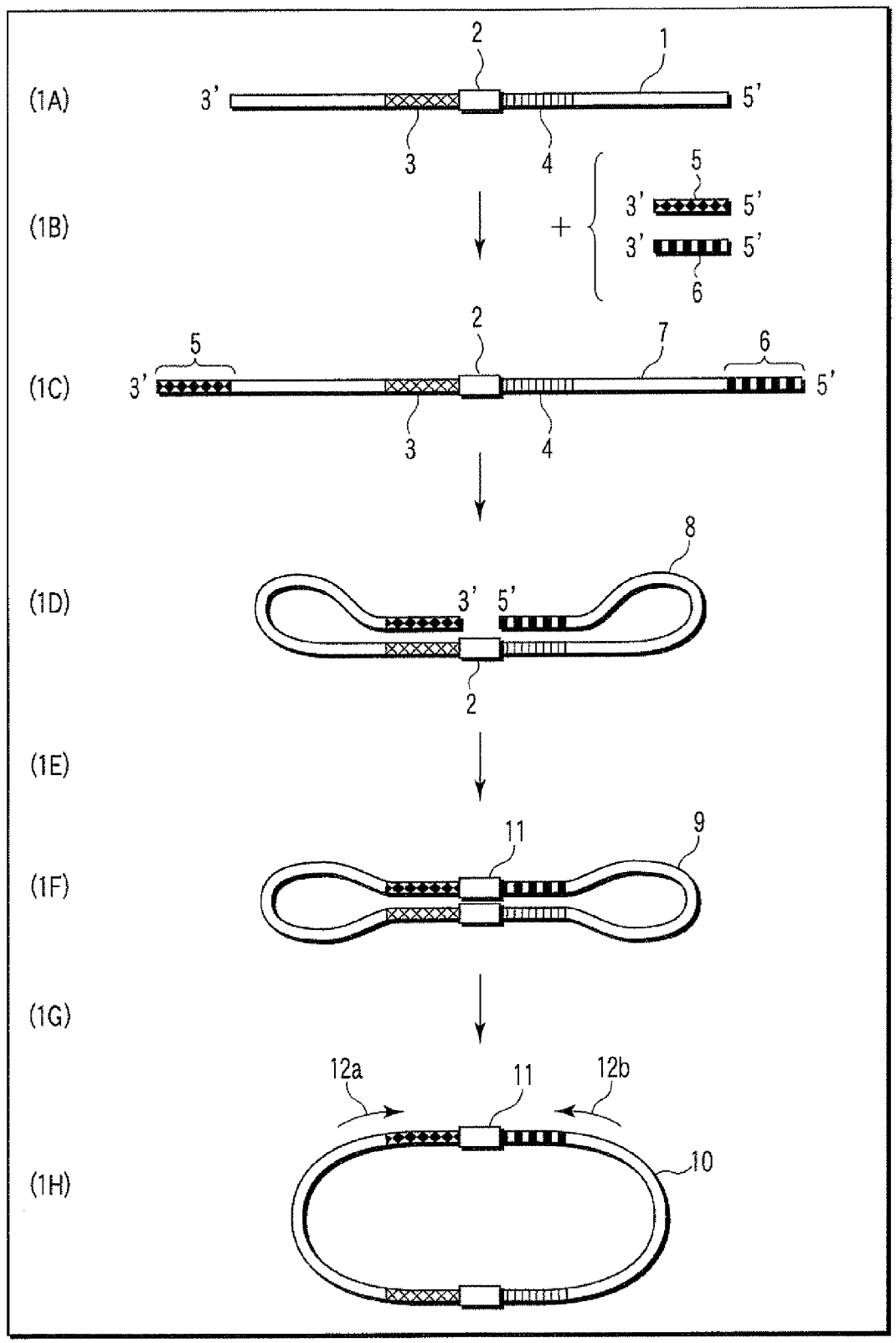
F I G. 1

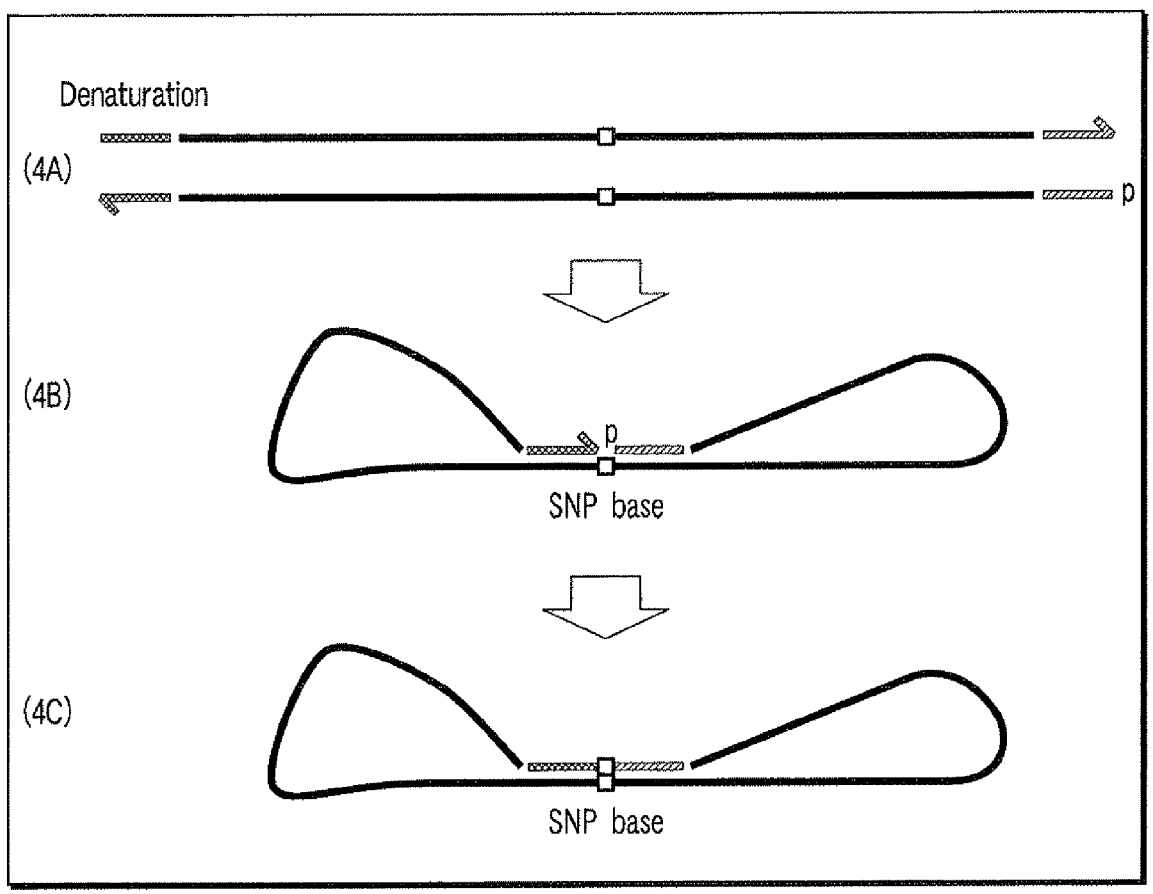
F I G. 4

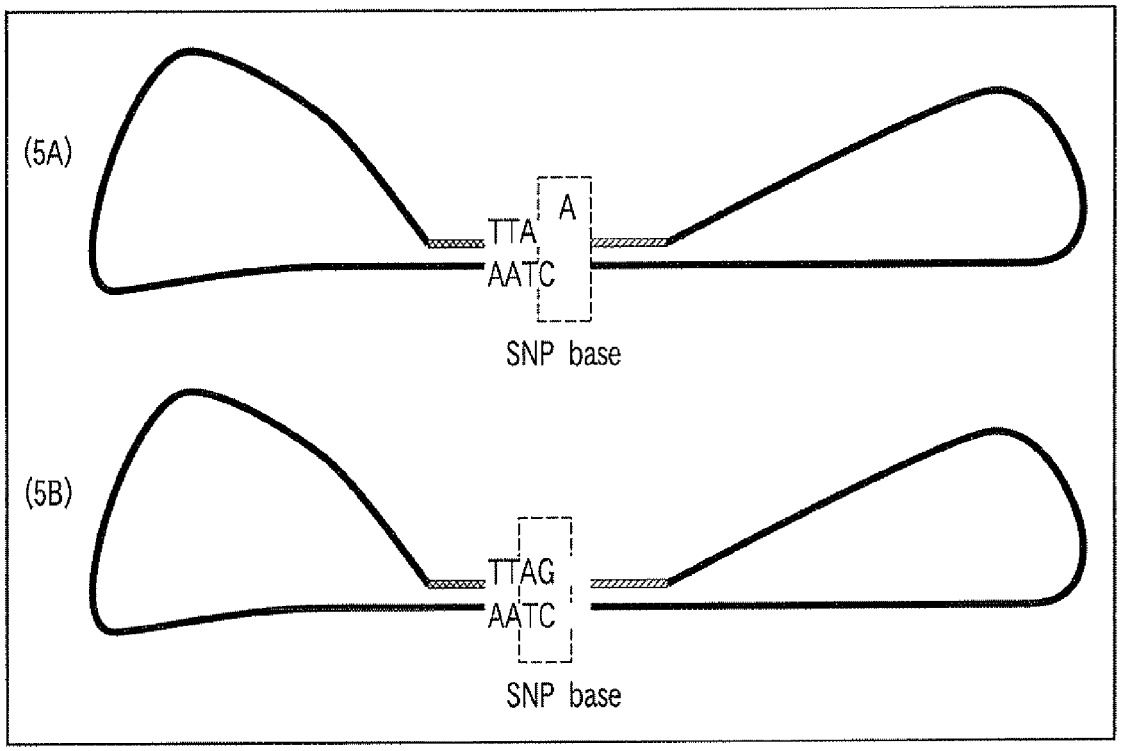
F I G. 5
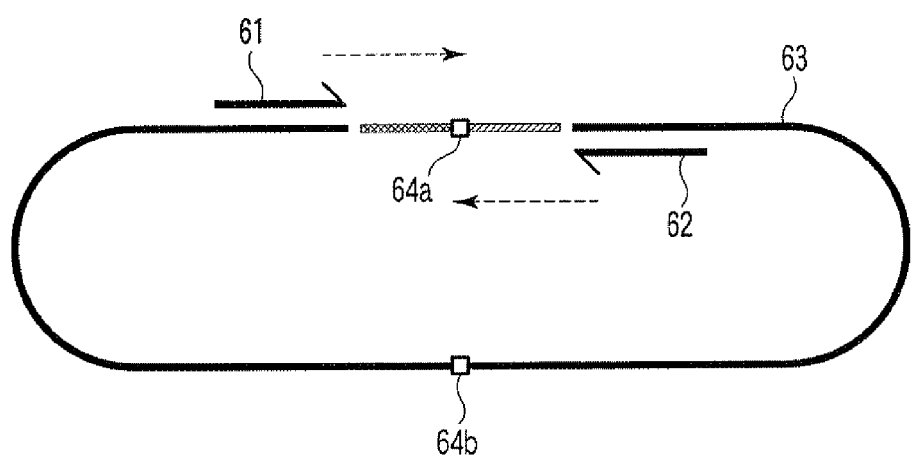
F I G. 6

(A)

Structure of nucleotide 1

(A1) Intramolecularly-detecting common probe sequence (LSO)    Artificial sequence

Phosphoric acid                                    Upstream primer sequence

Structure of nucleotide 2

(A2) Downstream connecting sequence    Artificial sequence

Phosphoric acid                                    Intramolecularly-detecting mutation probe sequence (ASO)

(B)

Structure of nucleotide 1

(B1) Intramolecularly-detecting common probe sequence (LSO)    Artificial sequence

Phosphoric acid                                    Upstream primer sequence

Structure of nucleotide 2

(B2) Downstream connecting sequence    Artificial sequence

Phosphoric acid                                    Intramolecularly-detecting mutation probe sequence (ASO)

FIG. 10

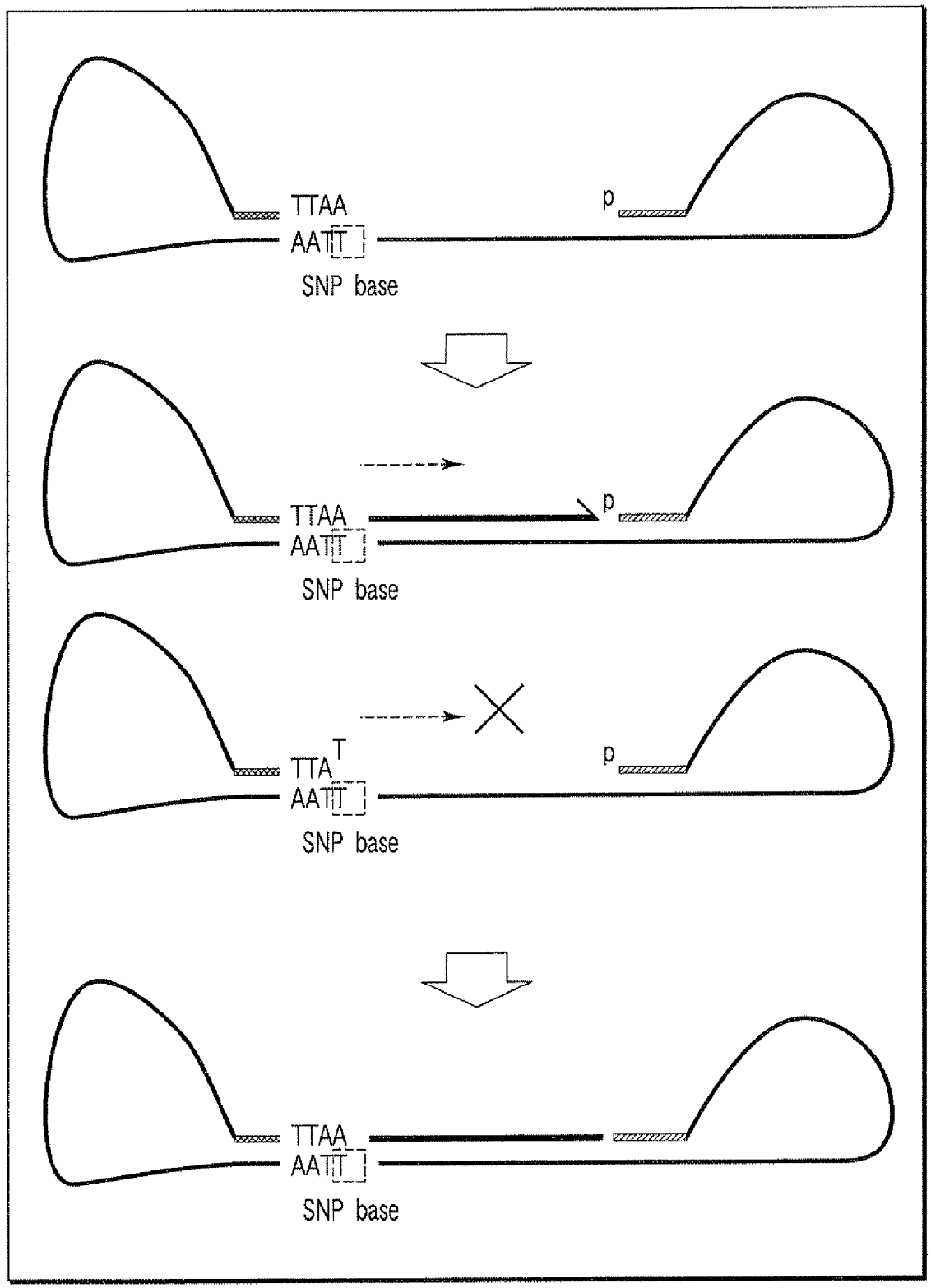
F I G. 12

Adapter 101
Adapter sequence of
restriction enzyme 1
Phosphoric acid
Intramolecular
probe sequence
Adapter 102 (the side containing 5' terminal of detecting chain)
Intramolecular
probe sequence
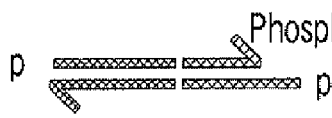
Phosphoric acid
Phosphoric acid
Adapter sequence of
restriction enzyme 2
FIG. 13

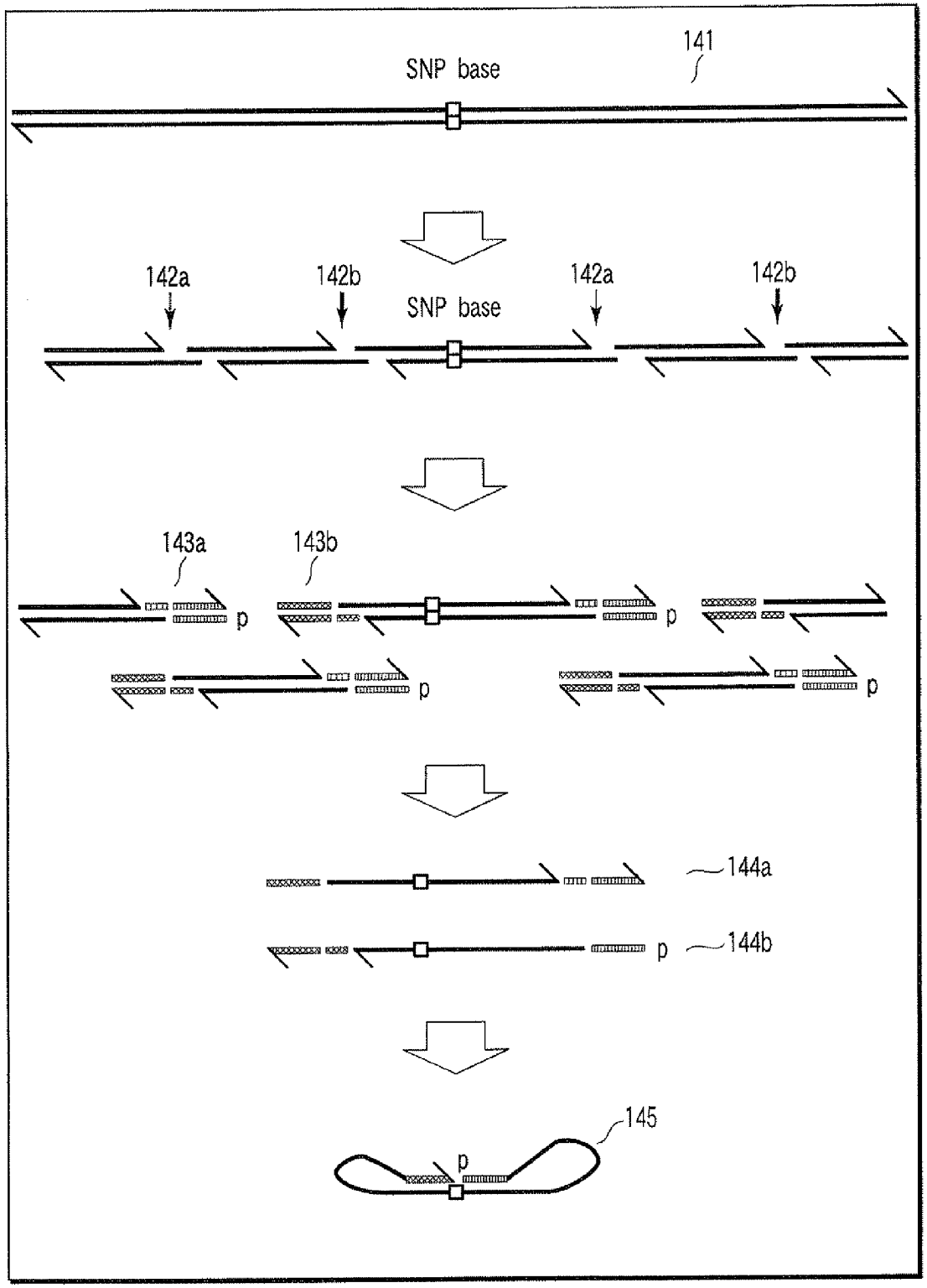
F I G. 14

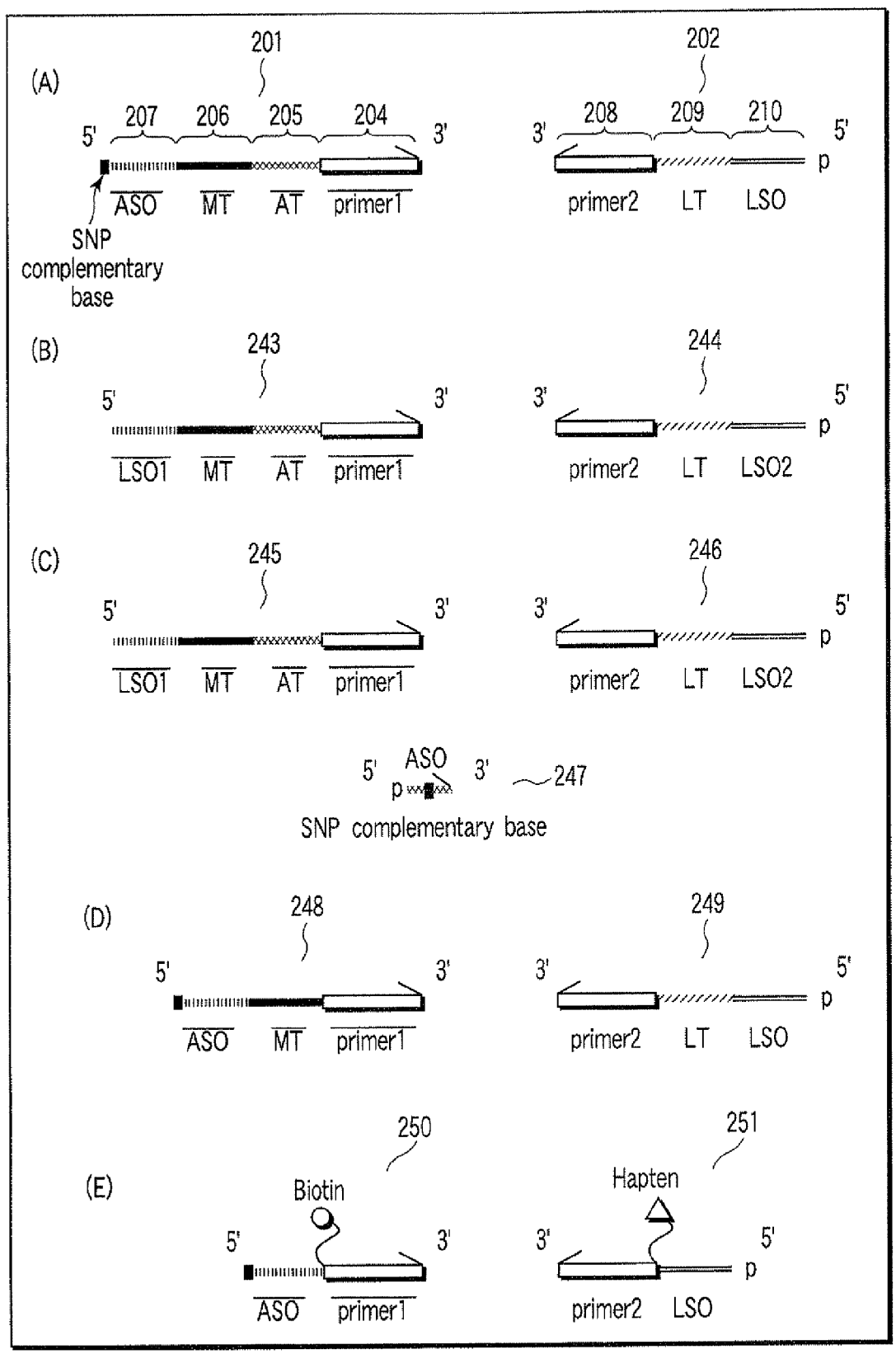
F I G. 18

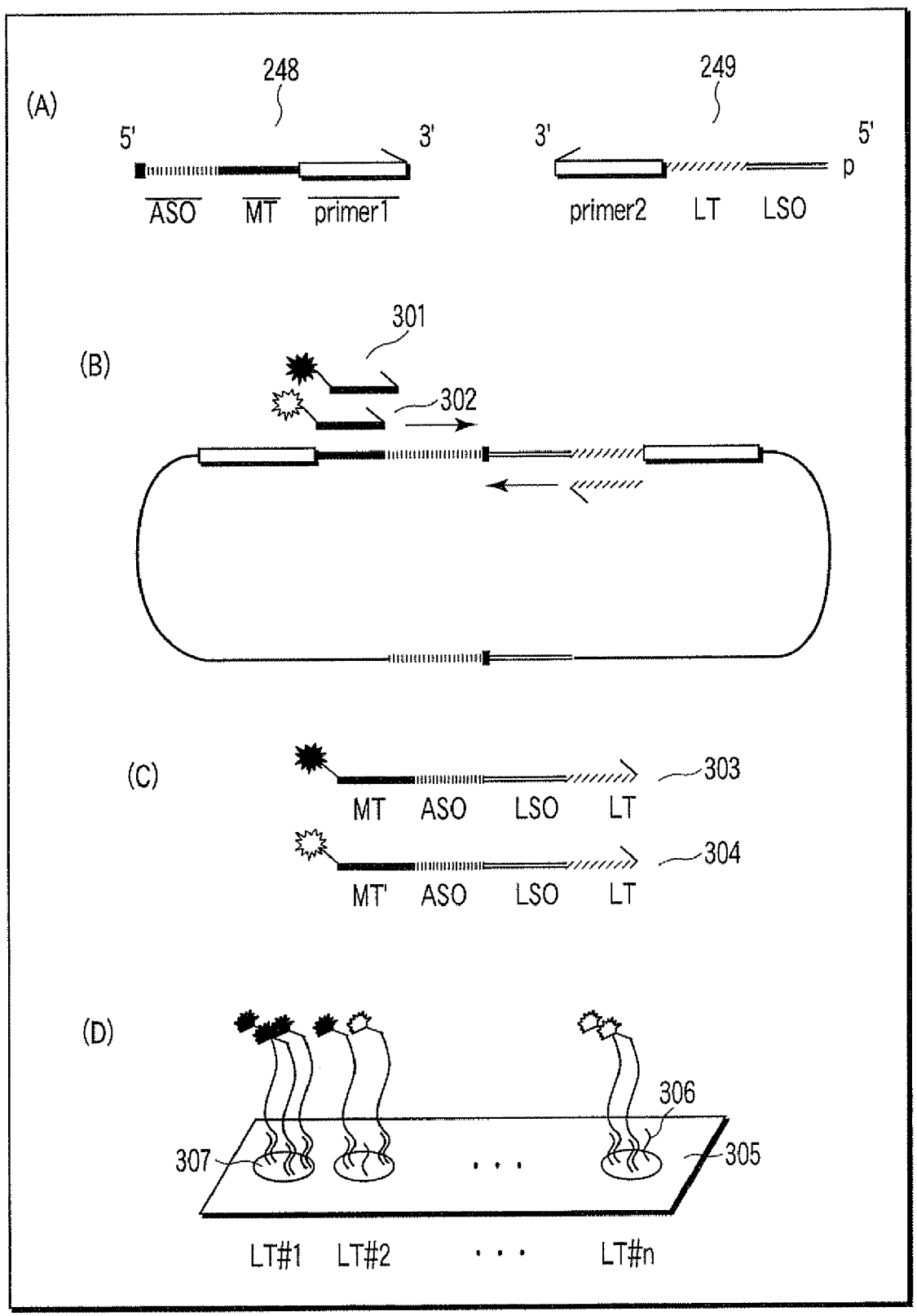
F I G. 26

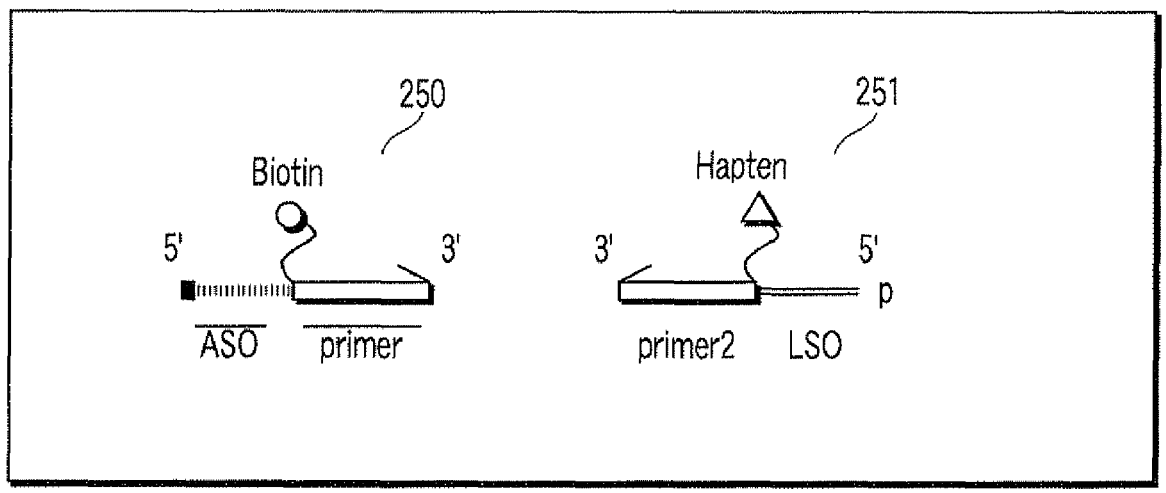
F I G. 27

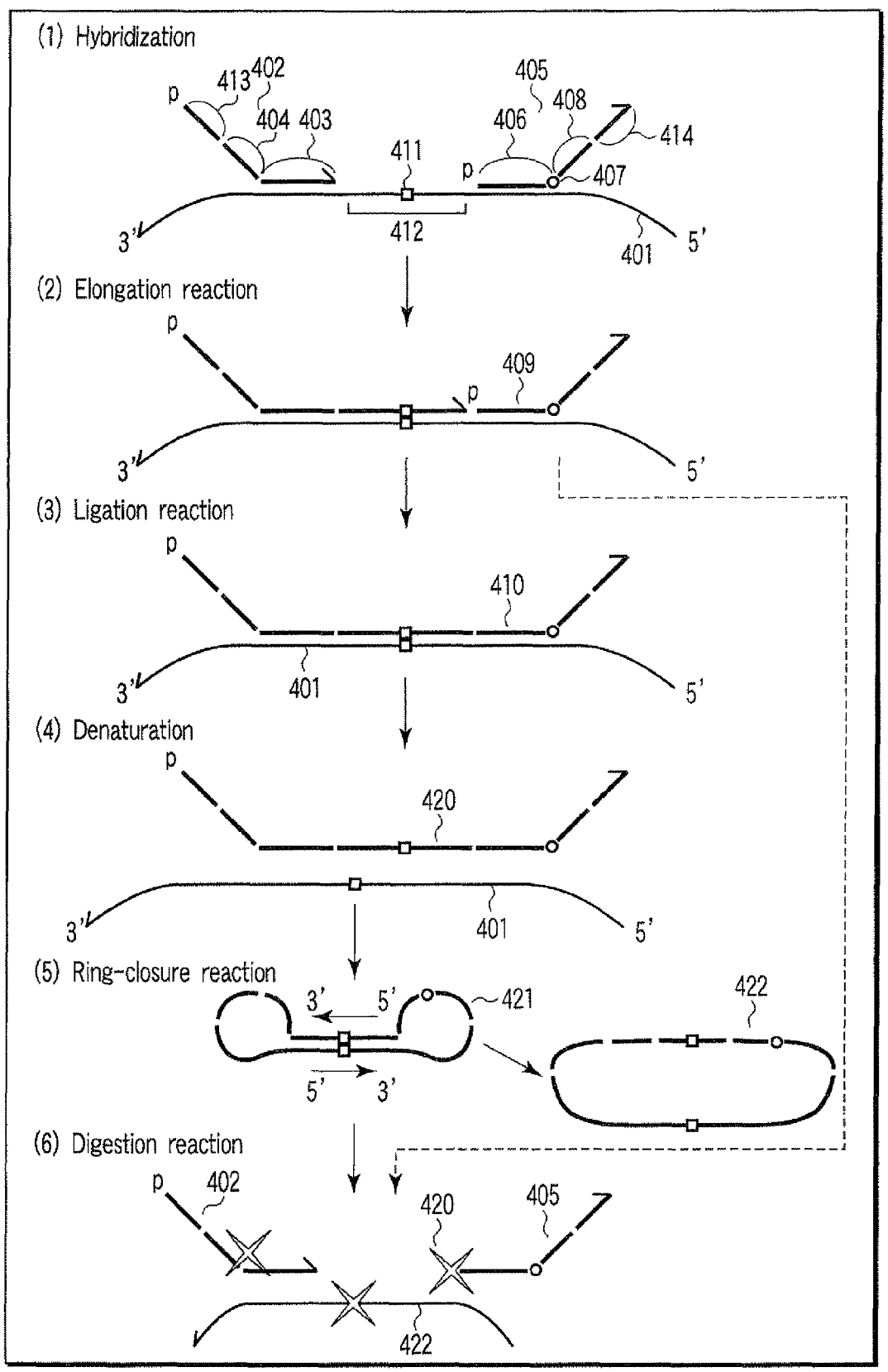
F I G. 28

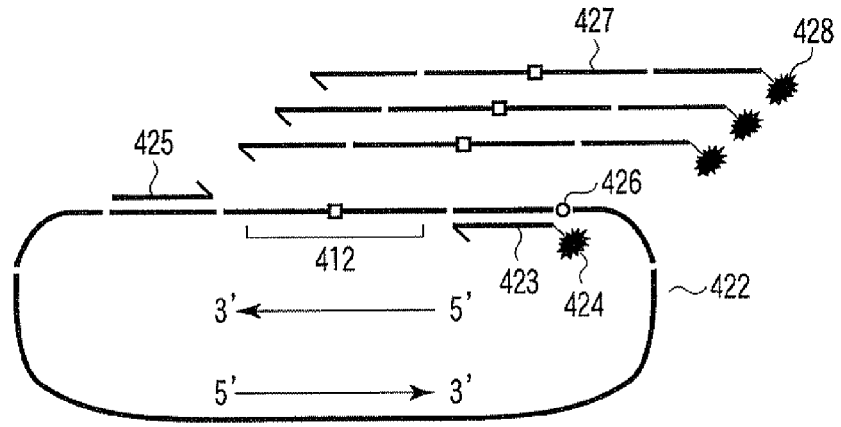
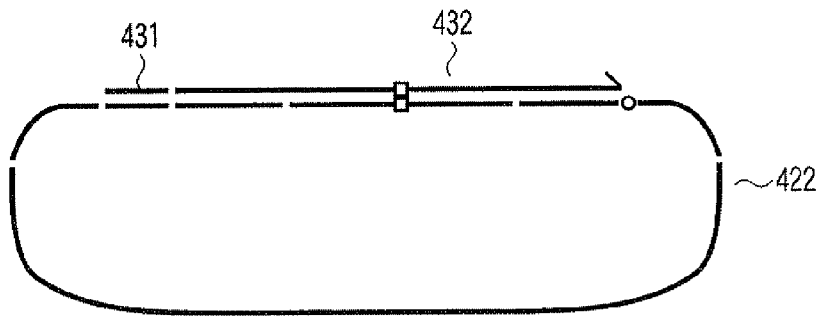
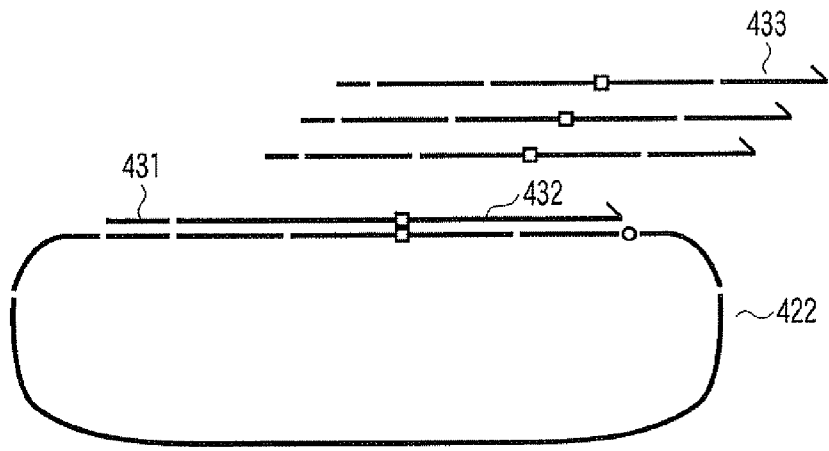
FIG. 29

(8)-A Detection of labeled PCR product on microarray
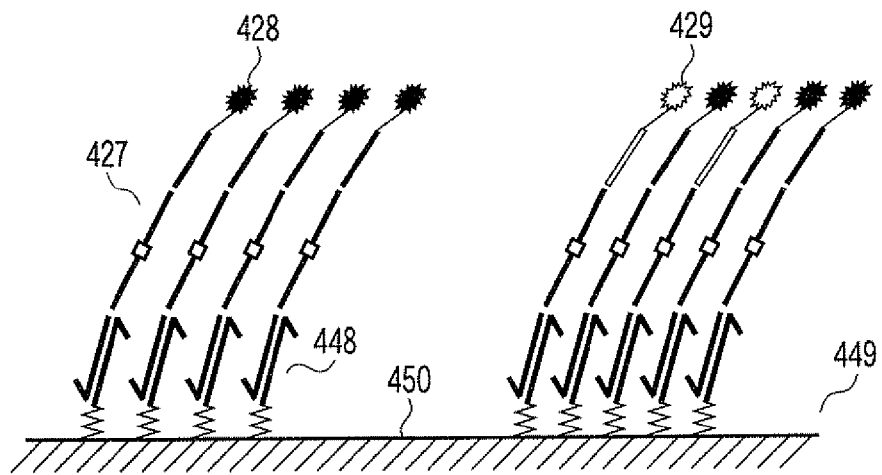
(8)-B Detection of in-vitro transcription product on microarray
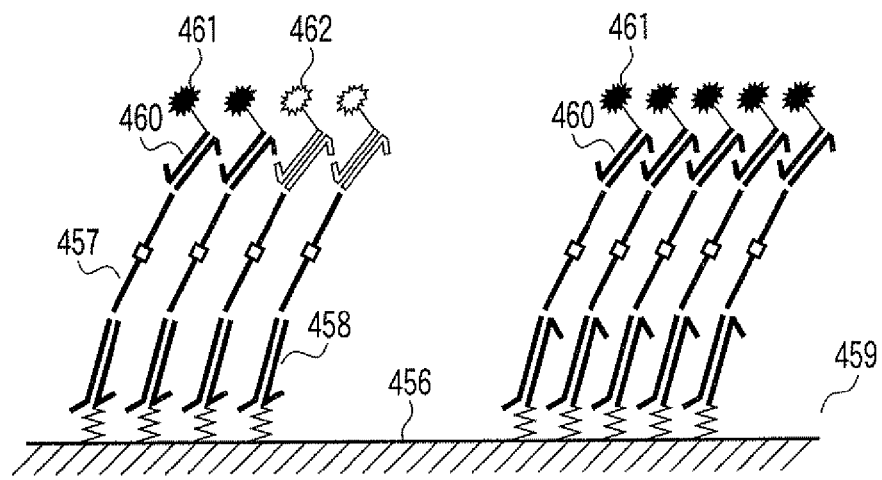
F I G. 30

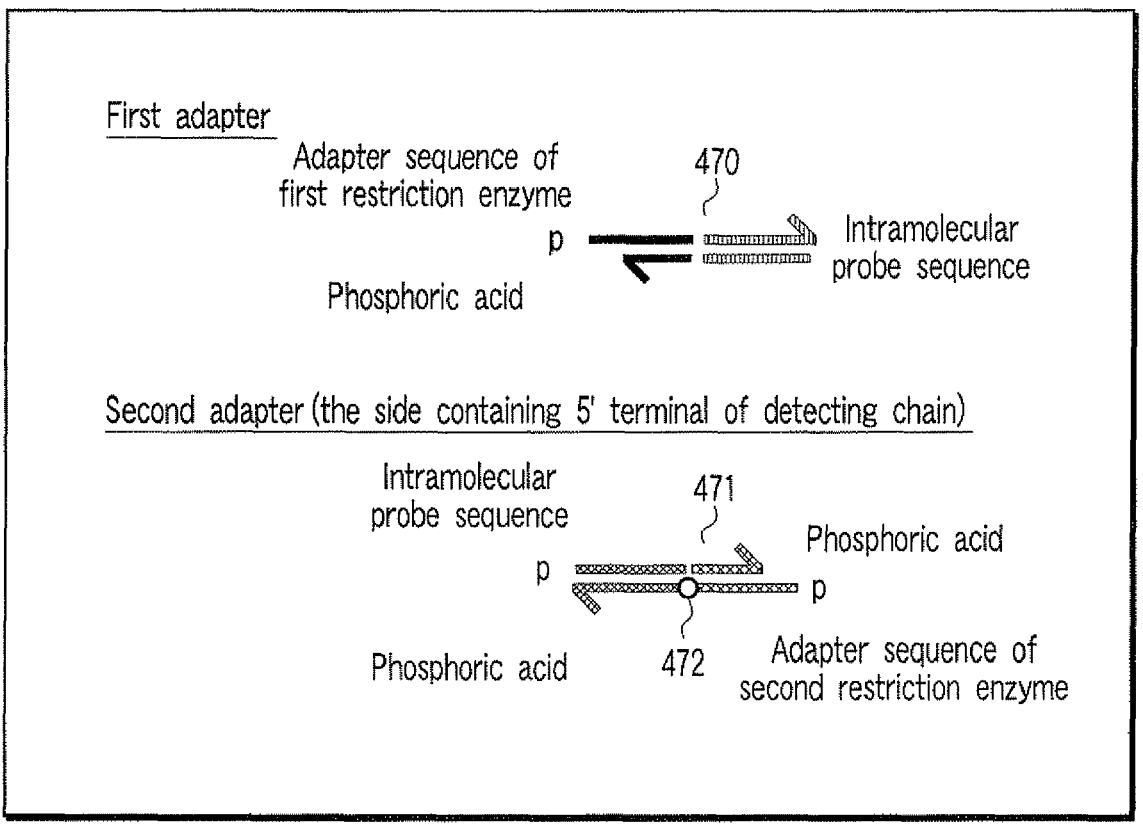
F I G. 31

SEQUENCE LISTING

```
<160> NUMBER OF SEQ ID NOS: 7

<210> SEQ ID NO 1
<211> LENGTH: 73
<212> TYPE: DNA
<213> ORGANISM: Artificial
<220> FEATURE:
<223> OTHER INFORMATION: Primer

<400> SEQUENCE: 1
acaggtcagg tgggaggttt ttctagagtg gacacggaat tgctctgctc ttgtaagtct    60
gggatgcttt cct                                                      73

<210> SEQ ID NO 2
<211> LENGTH: 73
<212> TYPE: DNA
<213> ORGANISM: Artificial
<220> FEATURE:
<223> OTHER INFORMATION: Primer

<400> SEQUENCE: 2
```
gcaggtcagg tgggatgttt tgtattcaag cggtggtaat tgctctgctc ttgtaagtct    60
gggatgcttt cct    73

<210> SEQ ID NO 3
<211> LENGTH: 78
<212> TYPE: DNA
<213> ORGANISM: Artificial
<220> FEATURE:
<223> OTHER INFORMATION: Primer

<400> SEQUENCE: 3
gctatctcgt cagacgcaga ttcattggtc agagaacaag gtgtcagaca taccctcttt    60
ttggagattt cctgttcc    78

<210> SEQ ID NO 4
<211> LENGTH: 23
<212> TYPE: DNA
<213> ORGANISM: Artificial
<220> FEATURE:
<223> OTHER INFORMATION: Primer

<400> SEQUENCE: 4
ccgtgtccac tctagaaaaa cct    23

<210> SEQ ID NO 5
<211> LENGTH: 23
<212> TYPE: DNA
<213> ORGANISM: Artificial
<220> FEATURE:
<223> OTHER INFORMATION: Primer

<400> SEQUENCE: 5
accaccgctt gaatacaaaa cat    23

<210> SEQ ID NO 6
<211> LENGTH: 23
<212> TYPE: DNA
<213> ORGANISM: Artificial
<220> FEATURE:
<223> OTHER INFORMATION: Primer

<400> SEQUENCE: 6
tgttctctga ccaatgaatc tgc    23

<210> SEQ ID NO 7
<211> LENGTH: 23
<212> TYPE: DNA
<213> ORGANISM: Artificial
<220> FEATURE:
<223> OTHER INFORMATION: Primer

<400> SEQUENCE: 7
gcagattcat tggtcagaga aca    23

METHOD OF DETECTING NUCLEOTIDE SEQUENCE WITH AN INTRAMOLECULAR PROBE

CROSS REFERENCE TO RELATED APPLICATIONS

This is a Continuation Application of PCT Application No. PCT/JP2007/050835, filed Jan. 19, 2007, which was published under PCT Article 21(2) in Japanese.

This application is based upon and claims the benefit of priority from prior Japanese Patent Applications No. 2006-013066, filed Jan. 20, 2006; No. 2006-353310, filed Dec. 27, 2006; and No. 2006-353311, filed Dec. 27, 2006, the entire contents of all of which are incorporated herein by reference.

BACKGROUND OF THE INVENTION

1. Field of the Invention

The present invention relates to a method of detecting a nucleotide sequence. The present invention also relates to a method of analyzing a nucleotide, in particular a method of analyzing a gene.

2. Description of the Related Art

A method of detecting nucleotide mutation by using specificity of a ligase enzyme was reported in Science in 1988 (Landegren, Science, 26; 241 (4869): 1077-80, (1988)). The method is much easier in controlling the reaction condition than the traditional mutation detection method by PCR, i.e., the mutation detection method by PCR using a primer having a mutation-complementary sequence at the 3' terminal (i.e., Sequence Specific Primer). For this reason, various more advanced methods such as LCR (ligase chain reaction) of using a heat-resistant ligase in the subsequent step and LDR (ligase detection reaction) by Barany et al. were developed since then (Jpn. Pat. Appln. KOKAI Publication No. 2000-511060). Molecule recognition with ligase is performed in combination of two probes having a nucleotide complementary to mutation at the 3' terminal. In particular, the method has been used frequently for detection of a single nucleotide polymorphism.

Human SNP (single nucleotide polymorphism) is a gene polymorphism occurring at a frequency of approximately one out of hundreds of bases. The mutation occurs over a wide range of genome, independently of the coding or non-coding region, in the form of substitution, insertion, or deletion of bases. The size of the human genome is 3 billion base pairs, and a frequency of $1/1,000$ base means presence of 3,000,000 SNPs. It is not easy to identify a medically useful particular SNP out of the vast number of SNPs. The number of SNP sets sensitive to a medicine or disease is thought to be about hundreds or dozens in the approximately 3,000,000 SNPs. For example, Roche provides a SNP-typing microarray for a medicine-metabolizing protein cytochrome P450. The array is designed to type a total of 31 alleles: 29 alleles for gene CYP2D6 and 2 alleles for gene CYP2C19. Thus, it seems that there is no need for typing tens or hundreds of thousands alleles for diagnosis. Practically, SNP typing of dozens, at most a hundred and several tens, of alleles would be needed.

However, even in typing of such a degree, use of the conventional Sanger's method results in increase in cost for the reagents and apparatus for reaction and also lower detecting efficiency of one mutation in one reaction. In addition, when the reaction specificity or signal is lower, it is not always possible to read the SNP from the waveform obtained. Under the circumstances above, the number of the samples to be detected is too many for the Sanger's method, in continuing typing as described above. Examples of the other typing methods include SSCP (single strand conformation polymorphism) method simpler in experimental procedure, SSP-PCR (sequence specific primers-PCR) method, real time PCR method by using a fluorescent TaqMan probe, and the like. However, these methods are also yet to be commercialized. Thus, there is a need for a method allowing analysis of many SNP types at lower cost, for commercialization of SNP testing. Currently, studies on the advanced methods, in particular based on the method of using the molecule recognition of polymerase or ligase, are eagerly in progress all over the world.

For example, a unique method by using molecule recognition of ligase is MIP (molecular inversion probe) method of Affymetrix (Jpn. Pat. Appln. KOKAI Publication No. 2004-528016). The method is a multiplex typing method of using a tag, which reduced the cost for probe synthesis and raised the reaction efficiency with a closed-ring probe and a gap ligation method (Hardenbol, P. et al., Nat. Biotechnol. 21, 673-678 (2003), Hardenbol, P. et al., Genome Res. 15, 269-675 (2005)). Alternatively, the RCA (rolling circle amplification) method developed by Lizardi of Yale Univ., an attractive nucleotide amplification method replacing PCR, is a method of producing a cyclic DNA from a primer with a strand-displacing polymerase continuously (Jpn. Pat. Appln. KOKAI Publication No. 2001-519172). The template for the amplification method should be cyclic. Thus, a padlock probe in which a terminal of single-strand chain probe hybridizes to a target and the hybrid is ring-closed by a ligase was developed, and a patent application on a detection method using the same was filed (Jpn. Pat. Appln. KOKAI Publication No. 2002-503948). Aisin Cosmos filed a patent application on a padlock probe method of using a protein RecA forming a triple-stranded chain and accelerating specific hybridization (Jpn. Pat. Appln. KOKAI Publication No. 9-220099) in Japan. In addition, the padlock probe is used not only in the RCA method but also in other methods (Jpn. Pat. Appln. KOKAI Publication No. 2001-514483, Japanese Patent Nos. 3085409 and 3590633).

In detecting mutation of a genome nucleotide with the padlock probe, a probe nucleotide is added in a great excess amount to a nucleotide sample amplified, for example by PCR or a reaction solution containing genome nucleotide itself for ligation reaction. It is necessary to prepare a detection probe, in addition to PCR primers, to perform such a reaction. Addition of a great excess amount of the probe nucleotide easily leads to increase of non-specific reaction. Further, when a nucleotide has a secondary structure in the region close to the detection sequence, the padlock probe hardly hybridizes to the object, leading to possible prohibition of detection.

By any one of the conventional methods above, for example when a nucleotide is detected by ligation reaction of the probe, a great excess amount of probe nucleotide should be added to the nucleotide sample, which leads to increase in cost and also increase of nonspecific reaction.

BRIEF SUMMARY OF THE INVENTION

An object of the present invention is to provide means of detecting a nucleotide sequence that is resistant to nonspecific reaction, does not require addition of a great excess amount of probe nucleotide, and allows operation at low cost.

The means of achieving the object above include the followings:

(1) A nucleotide sequence-detecting method, comprising:
  (a) preparing a nucleotide sample;
  (b) preparing a first intramolecular detecting sequence having a sequence complementary to a first sequence located at a 3'-side of the detecting site contained in the nucleotide sample and a second intramolecular detecting sequence having a sequence complementary to a second sequence located at a 5'-side of the detecting site, wherein at least one of the 3'-terminal nucleotide of the first intramolecular detecting sequence and the 5'-terminal nucleotide of the second intramolecular detecting sequence is modified in such a manner that they can bind to each other;
  (c) preparing a detecting chain containing a sequence of the detecting site by connecting the first intramolecular detecting sequence to the 3' terminal of the nucleotide sample and the second intramolecular detecting sequence to the 5' terminal;
  (d) allowing intramolecular hybridization at two positions of the detecting chain between the first sequence and the first intramolecular detecting sequence and between the second sequence and the second intramolecular detecting sequence;
  (e) connecting the 3' terminal of the first intramolecular detecting sequence to the 5' terminal of the second intramolecular detecting sequence directly or indirectly;
  (f) obtaining a cyclic structure by the connection (e); and
  (g) detecting the desired sequence in the nucleotide sample from the cyclic structure.

(2) The nucleotide sequence-detecting method according to (1), wherein a dumbbell structure is formed by means of the intramolecular hybridization in (d) and the connection in (e) between the 5' and 3' terminals of the dumbbell structure occurs by means selected from the group consisting of ligation and gap ligation.

(3) The nucleotide sequence-detecting method according to (2), wherein formation of the dumbbell structure and the connection thereof in (e) are performed together with thermal cycling under a thermal cycling condition previously determined.

(4) The nucleotide sequence-detecting method according to any one of (1) to (3), wherein the connection in (c) is performed by means selected from the group consisting of PCR by using at least a pair of primers and gap ligation, and restriction-enzyme cleavage and subsequent adapter ligation by using at least a pair of adapters.

(5) The nucleotide sequence-detecting method according to any one of (1) to (4), further comprising digesting un-ring-closed nucleotides with an enzyme after obtaining the cyclic structure in (f).

(6) The nucleotide sequence-detecting method according to any one of (1) to (5), wherein the desired sequence is detected in (g) by detection of the cyclic structure by means selected from the group consisting of DNA microarray, fluorescent beads, electrophoresis and mass spectrometry.

(7) The nucleotide sequence-detecting method according to any one of (1) to (5), wherein the desired sequence is detected in (g) by detection of the cyclic structure by detecting the amplification product obtained by using an elongation reaction using a primer that can detect formation of the connecting region of the cyclic structure.

(8) The nucleotide sequence-detecting method according to any one of (1) to (7), wherein the 5'-terminal of the second intramolecular detecting sequence is phosphorylated.

(9) The nucleotide sequence-detecting method according to any one of (1) to (8), wherein the 3' terminal of the second intramolecular detecting sequence includes a primer sequence and the 5' terminal of the first intramolecular detecting sequence is phosphorylated.

(10) The nucleotide sequence-detecting method according to any one of (1) to (9), wherein the connection in (f) is performed by means selected from the group consisting of chemical binding and biochemical binding.

(11) The nucleotide sequence-detecting method according to (10), wherein the chemical binding is performed by photo-assisted reaction.

(12) The nucleotide sequence-detecting method according to (10), wherein the biochemical binding is performed by enzyme-assisted reaction.

(13) The nucleotide sequence-detecting method according to any one of (1) to (12), wherein
  the first intramolecular detecting sequence contains a sequence complementary to the first sequence located at the 3' side and a tag sequence previously designed and allocated to carry information about the detection target at the detecting site, and/or
  the second intramolecular detecting sequence contains a sequence complementary to the second sequence located at the 5' side of the detecting site and additionally a tag sequence previously designed and allocated to carry information about the detection target at the detecting site.

(14) The nucleotide sequence-detecting method according to any one of (1) to (13), wherein the sequence is detected by means selected from the group consisting of SNP detection, gene expression measurement, methylation detection, and detection of deletion, insertion, substitution and microsatellite.

(15) An intramolecular detecting sequence, comprising a first intramolecular detecting sequence containing a sequence complementary to a first sequence located at a 3' side of a detecting site contained in a nucleotide sample, and a second intramolecular detecting sequence containing a sequence complementary to a second sequence located at a 5' side of the detecting site, wherein at least one of the 3'-sided nucleotide of the first intramolecular detecting sequence and the 5'-terminal nucleotide of the second intramolecular detecting sequence is modified to become mutually bindable.

(16) A detection kit for use in the method according to any one of (1) to (15), comprising any or all of enzymes, nucleotides, substrates, a buffer, and a detection microarray.

Another object of the present invention is to provide a method of analyzing a nucleotide that is higher in reaction efficiency and detection sensitivity and allows easy detection with a small amount of sample.

The means of achieving the object above include the followings:

(1) A nucleotide mutation-analyzing method, comprising:
  (a) preparing a duplicated chain complementary to an analyte nucleotide and connecting sequences complementary to the mutation to be detected on the duplicated chain or to the region around the mutation to both terminals of the duplicated chain, wherein
  these complementary sequences are different from each other and are so located to hybridize to the position on the duplicated chain between its terminal and the mutation or between the terminal and the mutation including mutation;
  (b) making the single-stranded duplicated chain have an intramolecular structure containing at least two bending regions;
  (c) making the terminals of the duplicated chain in the structure form a closed-ring nucleotide molecule covalently bound, directly or via a nucleoside monomer or a nucleotide different from mutation, by an oxygen or chemical reaction when there is an analyte mutation present;

(d) preparing a sequence containing the connecting region of the closed-ring nucleotide molecule or its complementary chain sequence, or both of them; and (e) analyzing nucleotide mutation by detecting presence of the sequence containing the region where the prepared closed-ring nucleotide molecule is connected or its complementary chain sequence.

(2) The nucleotide mutation-analyzing method according to (1), comprising:

(a) amplifying an analyte nucleotide first under a condition allowing amplification (first amplification), wherein the primers used consist of first and second primers for amplification of the sequence containing the mutation sequence of the analyte nucleotide, the first primer contains a second single-stranded sequence of the 3' side of the mutation possibly containing the mutation to be detected in the analyte nucleotide (second-primer elongation chain), a first probe sequence homologous to the 3'-sided sequence containing the mutation at the 5'-terminal side of the first primer, and additionally, a first priming sequence complementary to the partial sequence at the 3' side of the sequence corresponding to the first probe sequence on the second single-strand chain to the mutation site in the second single-strand chain, on the 3' terminal of the first primer, the second primer contains an elongation chain of the first primer, i.e., a second probe sequence homologous to the first single-stranded sequence of the 3' side of the mutation, at the 5'-terminal side of the second primer and a second priming sequence complementary to a partial sequence to the 3' side of a sequence corresponding to the second probe sequence at the 3' terminal of the second primer on the first single-strand chain to the first single-stranded the mutation site, and the 5' terminal of the second primer is phosphorylated;

(b) converting the first amplification product obtained by the first amplification into a single-stranded chain;

(c) making the single-strand-chain first amplification product form an intramolecular structure in ring-closure reaction, to give a closed-ring nucleotide molecule;

(d) amplifying the closed-ring nucleotide molecule obtained secondly under a condition allowing amplification (second amplification), to give a second amplification product containing the mutation to be detected contained in the closed-ring nucleotide molecule and sequences derived from at least the first and second probe sequences contained in the same closed-ring nucleotide molecule; and (e) analyzing the mutation to be detected in the analyte nucleotide by detecting the second amplification product obtained.

(3) The nucleotide mutation-analyzing method according to (2), wherein the base bound to the 3' terminal of the first amplification product is eliminated and the terminal is smoothed after the first amplification (a).

(4) The method according to any one of (1) to (3), further comprising decomposing straight chain nucleotide molecules other than the closed-ring nucleotide molecule partially or completely.

(5) The method according to any one of (1) to (4), wherein the first and second primers have an artificially designed sequence usable for identification and/or amplification between the priming sequence and the probe sequence.

(6) The method according to any one of (1) to (5), wherein: the first and second primers have an artificially designed sequence between the priming sequence and the probe sequence; the artificially designed sequence is one or more sequences corresponding to or common to the mutation to be detected; there is a second primer for each mutation site; it is the first primer of the mutation at the mutation site; these primers have different artificially designed sequences; and multiple mutations are detected and analyzed simultaneously.

(7) The method according to any one of (1) to (6), wherein: the first and second primers have an artificially designed sequence between the priming sequence and the probe sequence; the first amplification is performed by using these primers; the first amplification product obtained is amplified further (second amplification); the probe sequence and the artificially designed sequence are detected; and nucleotide mutation is analyzed based on the information thus obtained.

(8) The method according to any one of (1) to (7), wherein: in the single-stranded nucleotide containing the mutation to be detected contained in the first amplification product, the 3' and 5' terminals of the single-stranded nucleotide hybridize intramolecularly to the mutation site or the region around it to form an intramolecular structure, and the gap or nick of the terminal ring is present in the region close to the mutation site in the intramolecular structure or the region close to the mutation site including the mutation site.

(9) The method according to (8), wherein there is a nick between the mutation site of the intramolecular structure and the neighboring base and a closed-ring nucleotide molecule is formed there by action of a ligase.

(10) The method according to (8), wherein there is a gap in the intramolecular structure, and a closed-ring nucleotide molecule is formed there by complementary chain synthesis by a polymerase and ligation by a ligase.

(11) The method according to any one of (1) to (8), wherein the gap is a gap sequence having a sequence complementary to the mutation site of the first chain and the sequence close to the mutation site or a sequence complementary to the mutation site, the first primer contains a first probe sequence having a sequence complementary to part of the continuous sequence present at the 5' side of the first single-stranded mutation site on the 5'-terminal side of the first primer, the second primer contains a second probe sequence complementary to part of the continuous sequence close to the 5' side of the sequence corresponding to the mutation site on the second single-strand chain on the 5' side of the second primer, and a closed-ring nucleotide molecule is formed by action of a ligase in the presence of a 5'-terminal-phosphorylated fragment nucleotide having the nucleotide sequence of the gap sequence, after the first amplification by using the first and second primers.

(12) The method according to (11), wherein the mutation to be detected is a single-nucleotide mutation.

(13) The method according to any one of (1) to (9), wherein: the mutation to be detected is a single-nucleotide mutation; the first primer contains a first probe sequence homologous to the first single-stranded mutation base and part of the continuous sequence present at the 3' side of the mutation base on the 5'-terminal side of the first primer; and the second primer contains a second probe sequence homologous to part of the sequence close to the 3' side of the second single-strand-chain mutation base on the 5' side of the second primer.

(14) The method according to any one of (1) to (13), wherein the first primer used in the second amplification has an identifiable first chemical labeling substance and the second primer has an identifiable second chemical labeling substance, the second amplification product obtained is allowed to react with first particles carrying an antibody to the first chemical labeling substance and second particles carrying an antibody to the second chemical labeling substance, and the mutation to be detected in the analyte nucleotide is analyzed by detecting the particle aggregation caused by the reaction.

(15) The method according to any one of (1) to (13), wherein first and/or second primers previously labeled with a fluorescent dye are used in the second amplification, the second amplification product obtained is allowed to hybridize to a nucleotide microarray carrying a probe for capturing the second amplification product, and the mutation to be detected in the analyte nucleotide is analyzed by detecting the fluorescent dye label-derived fluorescent dye on the nucleotide microarray.

(16) The method according to any one of (6) to (15), wherein the artificially designed sequences are pre-selected so that the multiple identifiable fluorescent dyes are correlated with the mutation types possibly observed at the same mutation site, the sequence of the artificially designed sequences are designed so that the mutated nucleotides containing multiple mutation types possibly observed at the same mutation site hybridize to the same probes immobilized on a microarray previously made available, and the mutation to be detected in the analyte nucleotide is analyzed by detecting the artificially designed sequences selected and designed as described above and labeled with fluorescent dyes in multiple colors on a nucleotide microarray.

(17) The method according to any one of (6) to (15), wherein first and/or second primers previously labeled with a fluorescent dye are used in the second amplification, the second amplification product obtained is allowed to hybridize to fluorescent-identifiable particles, each carrying a probe for capturing one kind of artificially designed sequence, and the mutation to be detected in the analyte nucleotide is analyzed, based on the information on the fluorescence from the fluorescence particle and the second amplification product.

(18) The method according to (17), wherein the fluorescence particle is selected from the group consisting of bead and quantum dot containing a fluorescent dye and bead containing multiple kinds of quantum dots.

(19) A nucleotide mutation-analyzing method, comprising:

(a) amplifying an analyte nucleotide first under a condition allowing amplification (first amplification), wherein primers used include first and second primers for amplification of a sequence containing the mutation sequence of the analyte nucleotide, the first primer contains a second single-stranded sequence of a 3' side of the mutation possibly containing the mutation to be detected in the analyte nucleotide (second-primer elongation chain) or a first probe sequence homologous to the 3'-sided sequence containing the mutation at a 5'-terminal side of the first primer, and additionally, a first priming sequence complementary to the partial sequence at the 3' side of the sequence corresponding to the first probe sequence on the second single-strand chain to the mutation site in the second single-strand chain, on the 3' terminal of the first primer, and the second primer contains a second probe sequence homologous to the first single-stranded sequence of the 3' side of the mutation, an elongation chain of the first primer, at the 5'-terminal side of the second primer, and a second priming sequence complementary to a partial sequence at the 3' side of a sequence corresponding to the second probe sequence at the 3' terminal of the second primer on the first single-strand chain to the first single-stranded mutation site, and the 5' terminal of the second primer is phosphorylated;

(b) converting the first amplification product obtained by the first amplification into a single-stranded chain;

(c) making the single-strand-chain first amplification product form an intramolecular structure in ring-closure reaction, to give a closed-ring nucleotide molecule; and (d) the mutation to be detected in the analyte nucleotide is analyzed by detecting the difference in conformation between the closed-ring nucleotide molecule and non-ring-closed straight chain nucleotide molecules.

(20) The method according to (19), wherein the difference in conformation between the closed-ring nucleotide molecule and the non-ring-closed straight chain nucleotide molecules is detected by an electrophoretic method.

(21) The method according to any one of (1) to (20), wherein the amplification method is a PCR method.

(22) The method according to (21), wherein the second amplification method is asymmetric PCR.

(23) An assay kit for performing the method according to any one of (1) to (22), comprising a primer set, enzymes, substrates, a buffer agent, labeling substances, probes and/or a nucleotide microarray.

(24) The assay kit according to (23), further comprising fluorescence particles.

Another object of the present invention is to provide a method that does not require addition of a great excess amount of probe nucleotide with respect to a nucleotide when the nucleotide is detected by ligation reaction of the probe.

The means of achieving the object above include the followings:

(1) A nucleotide sequence-detecting method, comprising:

(a) preparing a nucleotide sample;

(b) preparing a first detecting chain-preparing nucleotide containing a sequence complementary to a first nucleotide sequence located at a 3' side of the detecting site contained in the nucleotide sample and a primer sequence on a 5' side that hybridizes to the more 3'-side than the first nucleotide sequence, and a second detecting chain-preparing nucleotide containing a sequence complementary to a second sequence located at the 5' side of the detecting site, a complementary chain synthesis-inhibiting structure on the 3' side thereof, and an oligonucleotide sequence on the 3' side that hybridizes to the more 5'-side than the second sequence, wherein at least one of the 5'-terminal nucleotide of the first detecting chain-preparing nucleotide and the 3'-terminal nucleotide of the second detecting chain-preparing nucleotide is modified in such a manner that they can bind to each other;

(c) preparing a detecting chain by allowing the primer sequence of the first detecting chain-preparing nucleotide and the oligonucleotide sequence of the second detecting chain-preparing nucleotide to hybridize to the nucleotide sample, allowing elongation reaction of the second detecting chain-preparing nucleotide with its complementary chain, and allowing ligation reaction at the 5' terminal of the first detecting chain-preparing nucleotide;

(d) allowing intramolecular hybridization of the detecting chain at two positions between the first sequence and the first detecting chain-preparing nucleotide and between the second sequence and the second detecting chain-preparing nucleotide;

(e) forming a cyclic structure by ring closure of the detecting chain at the 3' terminal of the first detecting chain-preparing nucleotide and the 5' terminal of the second detecting chain-preparing nucleotide;

(f) amplifying the sequence containing the connecting region of the cyclic structure; and (g) detecting the detecting-site sequence in the nucleotide sample by detecting the amplification product obtained by amplification (f).

(2) The nucleotide sequence-detecting method according to (1), wherein the ligation and ring closure in (e) is performed by means selected from the group consisting of ligation and gap ligation.

(3) The method according to (2), wherein the steps of intramolecular hybridization and ligation/ring closure are performed together with thermal cycling under a thermal cycling condition previously determined.

(4) The method according to any one of (1) to (3), further comprising digesting non-ligated/ring-closed nucleotides after the ligation and ring closure.

(5) The method according to any one of (1) to (4), wherein the amplification step (f) is PCR producing a product containing the connecting region.

(6) The method according to any one of (1) to (4), wherein the amplification step (f) is RNA synthesis by in-vitro transcription with an RNA polymerase, producing a product containing the connecting region.

(7) The method according to any one of (1) to (6), wherein the modification allowing ligation is phosphorylation of nucleotide.

(8) The method according to any one of (1) to (7), wherein the step (g) is performed by detecting hybridization between the amplification product and a DNA microarray.

(9) The method according to any one of (1) to (7), wherein the step (g) is performed by indirect detection of the amplification product, i.e., by hybridization to the amplification product, hybridization of the amplification product to a nucleotide carrying a detectable label, and detection of the detectable label.

(10) A detection kit for use in the method according to any one of (1) to (9), comprising a reagent containing any or all of enzymes, nucleotides, substrates, a buffer, and a detection microarray.

BRIEF DESCRIPTION OF THE SEVERAL VIEWS OF THE DRAWING

FIG. 1 is a schematic chart showing the present invention;
FIG. 4 is a chart showing an aspect of the present invention;
FIG. 5 is a chart showing an aspect of the present invention;
FIG. 6 is a chart showing an aspect of the present invention;
FIG. 10 is a chart showing an aspect of the present invention;
FIG. 12 is a chart showing an aspect of the present invention;
FIG. 13 is a chart showing an aspect of the present invention;
FIG. 14 is a chart showing an aspect of the present invention;
FIG. 18 is a chart showing an aspect of the present invention;
FIG. 26 is a chart showing an aspect of the present invention;
FIG. 27 is a chart showing an aspect of the present invention;
FIG. 28 is a schematic view showing an aspect of the present invention;
FIG. 29 is a schematic view showing an aspect of the present invention;
FIG. 30 is a schematic view showing an aspect of the present invention;
FIG. 31 is a schematic view showing an aspect of the present invention.

DETAILED DESCRIPTION OF THE INVENTION

Figure 2:
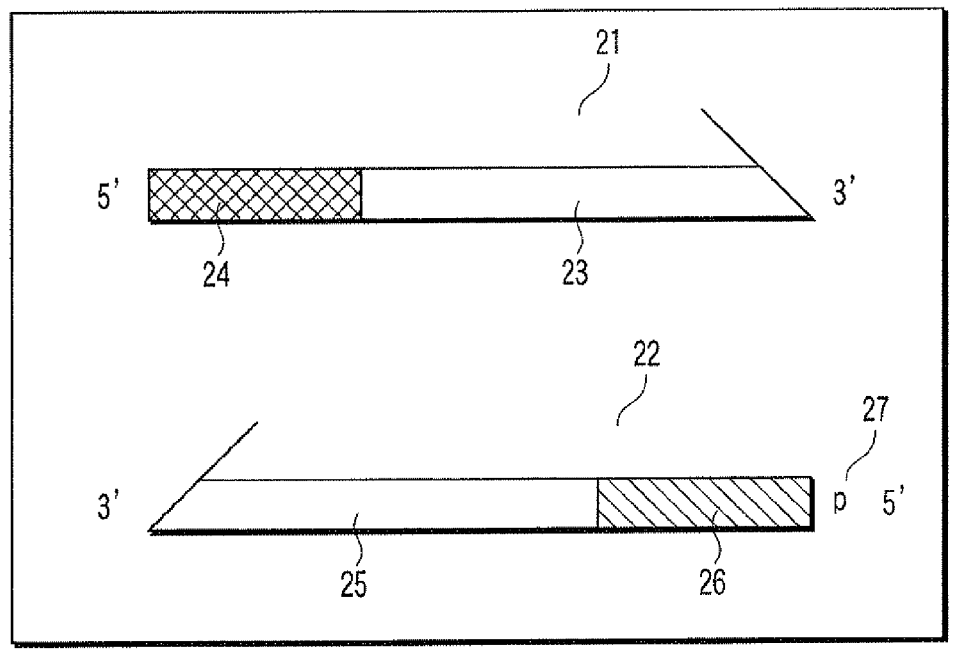
FIG. 2 is a chart showing an aspect of the present invention.

I. Nucleotide Sequence-Detecting Method Using Intramolecular Sequence Detection Reaction

1. EXPLANATION OF TERMS

The term "nucleotide" used below means all DNAs and RNAs including cDNA, genomic DNA, synthetic DNA, mRNA, entire RNA, hnRNA, and synthetic RNA.

The term "gene" used below means both coding and non-coding regions in genome.

In an aspect of the present invention, provided is a nucleotide sequence-detecting method, and the nucleotide to be detected thereby may be a nucleotide having a desirable particular sequence or a nucleotide related to a particular gene mutation. The nucleotide sequence-detecting method according to the present invention allows, for example, analysis and/or detection of gene mutation and/or expression analysis, but the application thereof is not limited thereto. The method according to the present invention may be used favorably not only for gene mutation analysis but also for analysis and/or detection of any nucleotide.

The scope of the term "mutation" used below includes, but is not limited to, gene polymorphism including SNP and repeating sequences such as microsatellite sequences, insertion, deletion and/or substitution of bases, combination thereof, methylation of genome, and the like.

The term "5' side of detecting site" or "3' side of detecting site" may mean an oligonucleotide for example having 1, 2, 3, 4 and 5 bases located to the 5'- or 3'-side of the mutation site or an oligonucleotide excluding the mutation site for example having 1, 2, 3, 4 and 5 bases located to the 5'- or 3'-side of the mutation site, but the number of bases is not limited and may be 6, 7, 8, 9 or 10. The detecting site above may contain additionally the sequence contained in the detecting site, for example, the mutation site, and only the mutation site thereof may be included.

The phrase "at least one of the 3' terminal of the first intramolecular detecting sequence and the 5' terminal of the second intramolecular detecting sequence is so modified to bind to the nucleotide" or "both are modified to bind to each other" used below means that the 3'- and 5'-terminals of the nucleotide are so modified to bind to each other by known chemical or biochemical means. Examples of such modification allowing mutual binding include, but are not limited to, phosphorylation of the 5' terminal, and binding of a photosensitive pyrimidine base having a substituting vinyl group at the 5-carbon to the 5' terminal, as described in Japanese Patent No. 3753942. The latter modification allows reversible nucleotide binding by photochemical reaction.

The "detecting chain" used below is a sequence of a nucleotide sample having "intramolecular detecting sequences" respectively bound to 3' and 5' terminals. The detecting chain is a nucleotide molecule causing intramolecular reaction, according to the present invention.

2. SUMMARY OF THE INVENTION

The present invention provides a nucleotide sequence-detecting method, including the following steps:
(1) detecting chain-preparing reaction,
(2) intramolecular detecting reaction,
(3) straight chain-digesting reaction,
(4) amplification reaction, and
(5) detection reaction.

The detecting chain according to the present invention is prepared in reaction of binding intramolecular detecting sequenced to the 3'- and 5'-terminals of a nucleotide sample.

The intramolecular detecting reaction according to the present invention includes a reaction of hybridizing sequences complementary to the sequences at positions of the 3'- and 5'-terminals of the detecting site contained in the intramolecular detecting sequence intramolecularly to the sequences of the 3'- and 5'-terminals, and a subsequent reaction of preparing a cyclic structure.

The straight chain-digesting reaction according to the present invention is an arbitrary reaction, and may be or may not be performed, but gives more stabilized results finally when performed. The straight chain-digesting reaction is a reaction of digesting the intramolecular detecting sequence that did not form the cyclic structure and other nucleotides contained in the sample.

The amplification reaction according to the present invention is an arbitrary reaction, and may be eliminated, for example, when the cyclic structure is detected, for example, by electrophoresis or mass spectrometry. Alternatively, for example for determining whether binding is performed for production of the cyclic structure by amplification of the region close to the binding site, the region close to the binding site may be amplified. In such a case, the sequence of detecting site complementary to the binding site is preferably not amplified. Thus, the cyclic structure may be amplified after cleavage at any position.

In an aspect of the present invention, provided is a nucleotide sequence-detecting method, comprising:
(a) preparing a nucleotide sample;
(b) preparing a first intramolecular detecting sequence having a sequence complementary to the first sequence located to the 5'-side of the detecting site contained in the nucleotide sample and a second intramolecular detecting sequence having a sequence complementary to the second sequence located to 3'-side of the detecting site, wherein at least one of the 5'-terminal nucleotide of the first intramolecular detecting sequence and the 3'-terminal nucleotide of the second intramolecular detecting sequence is so modified to bind to each other;
(c) preparing a detecting chain by connecting the first intramolecular detecting sequence to the 5' terminal of the nucleotide sample and the second intramolecular detecting sequence to the 3' terminal;
(d) allowing intramolecular hybridization at two positions of the detecting chain between the first sequence and the first intramolecular detecting sequence and between the second sequence and the second intramolecular detecting sequence;
(e) connecting the 5' terminal of the first intramolecular detecting sequence to the 3' terminal of the second intramolecular detecting sequence;
(f) obtaining a cyclic structure by the connection of (e); and
(g) detecting the desired sequence in the nucleotide sample from the cyclic structure.

An aspect of the present invention will be described with reference to FIG. 1. First, a nucleotide sample 1 containing a detecting site 2 to be detected is prepared (FIG. 1, 1A).

Then, a first intramolecular detecting sequence 5 and a second intramolecular detecting sequence 6 are bound to the nucleotide sample 1 (FIG. 1, 1B), to obtain a detecting chain 7 (FIG. 1, 1C). The first intramolecular detecting sequence 5 has a nucleotide complementary to a first nucleotide sequence 3 located at the 3'-sided position of the analyte detecting region 2. The second intramolecular detecting sequence 6 contains a nucleotide complementary to a second nucleotide sequence 4 located at the 5'-sided position of the analyte detecting region 2. The binding method is not particularly limited, and, for example, PCR using at least a pair of primers, single-stranded gap ligation, or adapter ligation by using least a pair of adapters may be used. The first intramolecular detecting sequence 5, which is complementary to the first nucleotide sequence 3, is bound to 3'-sided terminal located at the 3'-side of the first nucleotide sequence 3 of the detecting chain 7. The base complementary to the base located at the most 3'-sided position of the first nucleotide sequence 3 is present at the most 5'-sided position of the first intramolecular detecting sequence 5. The base complementary to the base located at the most 5'-sided position of the first nucleotide sequence 3 is present at the most 3'-sided position of the first intramolecular detecting sequence 5. Similarly, the second intramolecular detecting sequence 6, which is complementary to the second nucleotide sequence 4, is bound to the 5'-sided terminal located to the 5'-side of the second nucleotide sequence 4 of the detecting chain 7. The base complementary to the base at the most 5'-sided position of the second nucleotide sequence 4 is present at the most 3'-sided position of the second intramolecular detecting sequence 6, and the base complementary to the base at the most 3'-sided position of the second nucleotide sequence 4 is present at the most 5'-sided position of the second intramolecular detecting sequence 6. Thus, the first nucleotide sequence 3 and the first intramolecular detecting sequence 5 hybridize to each other with their 3' to 5' directions reversed. Similarly the second nucleotide sequence 4 and the second intramolecular detecting sequence 6 hybridize to each other with their 3' to 5' directions reversed.

The detecting chain 7 obtained by binding of the first intramolecular detecting sequence 5 and the second intramolecular detecting sequence 6 hybridizes intramolecularly at two positions of the first nucleotide sequence 3 located at the 3'-sided position of the analyte detecting region 2 and the second nucleotide sequence 4 located at the 5'-sided position of the analyte detecting region 2 (FIG. 1, 1D), to form a dumbbell-like shape.

Then, the 3' terminal of the first intramolecular detecting sequence 5 and the 5' terminal of the second intramolecular detecting sequence 6 are connected to each other to form a closed-ring structure 9 (FIG. 1, 1F). These terminals may be ligated or not ligated to each other according to the analyte detecting region 2. Thus, these terminals are ligated to each other when the analyte detecting region 2 to be detected is present in the reaction system, but are not ligated when it is not present in the reaction system. Alternatively, for example in SNP detection, the terminals are ligated to each other when the base of the analyte detecting region 2 is a kind of base forming a desirable gene type, but not ligated when another kind of base is present. These terminals are ligated to each other, because at least one of the 5'-terminal nucleotide of the first intramolecular detecting sequence 5 and the 3'-terminal nucleotide of the second intramolecular detecting sequence 6 is modified to bind to each other. The ligation may include or may not include elongation of the 5'- or 3'-terminal nucleotide. In other words, the ligation may be performed by ligation or gap ligation.

The closed-ring structure 9, when heated in the reaction system, dissociates into a cyclic structure 10 having no intramolecular double-stranded chain by dissociation of the double-stranded nucleotide between a connecting region 11 and the analyte detecting region 2 by thermal denaturation (FIG. 1, 1H).

Such a cyclic structure 10 may be detected and/or quantitatively determined by electrophoretic and/or mass spectrometric analysis of the reaction product, or alternatively by forming an elongated or amplified product containing the connecting region 11 in reaction with a primer pair 12a and 12b and analyzing the elongated or amplified product obtained. In addition, nucleotides other than the cyclic structure 10 may be digested with enzyme after formation of the cyclic structure 10. In this way, it is possible to detect and/or determine the cyclic structure 10 quantitatively, more easily and accurately.

The elongated or amplified product may be detected and/or determined quantitatively by any known means of detection and/or quantitative determination. For example, a probe binding to the elongated or amplified product specifically may be used, or a probe bound, for example, to a microarray or fluorescent bead may be used. The primer may be labeled.

A single-stranded nucleotide sample 1 is used in FIG. 1, but a double-stranded chain may be used instead. However, only one of the double strands forms a final cyclic structure, and the nucleotide chain used is decided depending on the design of the first and second intramolecular detecting sequences.

Thermal cycling may be performed simultaneously with the steps from 1B (i.e., during production of detecting chain) to 1H (i.e., during production of cyclic structure) in FIG. 1, or simultaneously with the steps of from 1C (i.e., after production of detecting chain) to 1H in FIG. 1. The "thermal cycling" is to heat and cool a reaction system between particular temperatures, and it is possible to perform the intramolecular hybridization more efficiently in this way. Conversion of the double-stranded nucleotide into a single-stranded nucleotide by thermal denaturation during intramolecular reaction of the PCR-amplified nucleotide is advantageous, because it is possible to install a step of thermally denaturing the double-stranded chain periodically, reliably and advance the intramolecular hybridization while preventing the intramolecular reaction by reassociation of the two strands.

The "intramolecular detecting sequences", which are present at both terminals of the detecting chain according to the present invention, have a sequence complementary to the sequence to be detected by analyzer on the detecting chain. The intramolecular detecting sequence may be as needed a primer for preparation of complementary chain, and the probe for ligation may function as a sequence. In addition, the detecting chain contains intramolecular detecting sequences forming a complementary chain by hybridizing to the upstream and the downstream of the detecting site sequence (i.e., intramolecular hybridization) and forming an intramolecular structure, and it may be a primer that produces a double-stranded chain containing the detecting chain by gap ligation or the detecting chain, or alternatively, it may be a connecting sequence itself. The intramolecular detecting sequence may have, in addition to the primer and the connecting sequence, an additional desirable sequence or any sequence.

The any sequence may be an artificially designed sequence designed artificially. The term "artificially designed sequence" used here means a nucleotide sequence designed artificially. The artificially designed sequence may be designed deliberately according to the application by the user or for a specific purpose. For example, the artificially designed sequence for use in the present invention may be used for the purposes of identification and/or elongation.

It is possible to eliminate a step of preparing the probe separately and adding it in a great amount by the method according to the present invention of designing the sequence by placing probe sequences at both terminals of a nucleotide sample, and to make the hybridization efficiency between the analyte detecting region and each probe higher, because the method uses an intramolecular reaction. Advantageously, it is thus possible to reduce the cost for probe preparation and avoid the nonspecific reactions caused by addition thereof in a great amount.

It is possible to form a hybrid more stable than the secondary structure of the nucleotide sample according to the present invention, because there are probe sequences at both terminals of the nucleotide sample. For this reason, there are often sequences not detected in the conventional method of preparing probes separately and hybridizing them with the nucleotide sample, because of inhibition by the reaction-inhibiting secondary structure of the nucleotide sample. It is possible to detect sequences that were not detected and raise the detection efficiency by forming such a structure more stable than the reaction-inhibiting secondary structure by intramolecular hybridization.

According to the present invention, the ligation reaction occurs only on the PCR-amplified nucleotide because the probe for the intramolecular hybridization is connected in the first amplification reaction. Thus, the method is more advantageous than the conventional method of adding probes separately in that the non-specific ligation reaction occurs less frequently, because there is detection signal observed only when the PCR amplification is performed and the ring-closure reaction occurs at the same time.

3. FIRST ASPECT (1) Method of Preparing a Detecting Chain by PCR

The method of preparing a detecting chain by PCR according to the present invention will be described with reference to FIGS. 2 and 3.

See FIG. 2. A first intramolecular detecting sequence 21 for use in the method has a first primer sequence 23 and a first intramolecularly-detecting probe sequence 24, i.e., a sequence complementary to the sequence close to the 5'-sided sequence of the detecting site. A second intramolecular detecting sequence 22 has a second primer sequence 25 and a second intramolecularly-detecting probe sequence 26, i.e., a sequence complementary to the sequence close to the 5'-sided sequence of the detecting site, and the 5' terminal is phosphorylated additionally.

Figure 3:
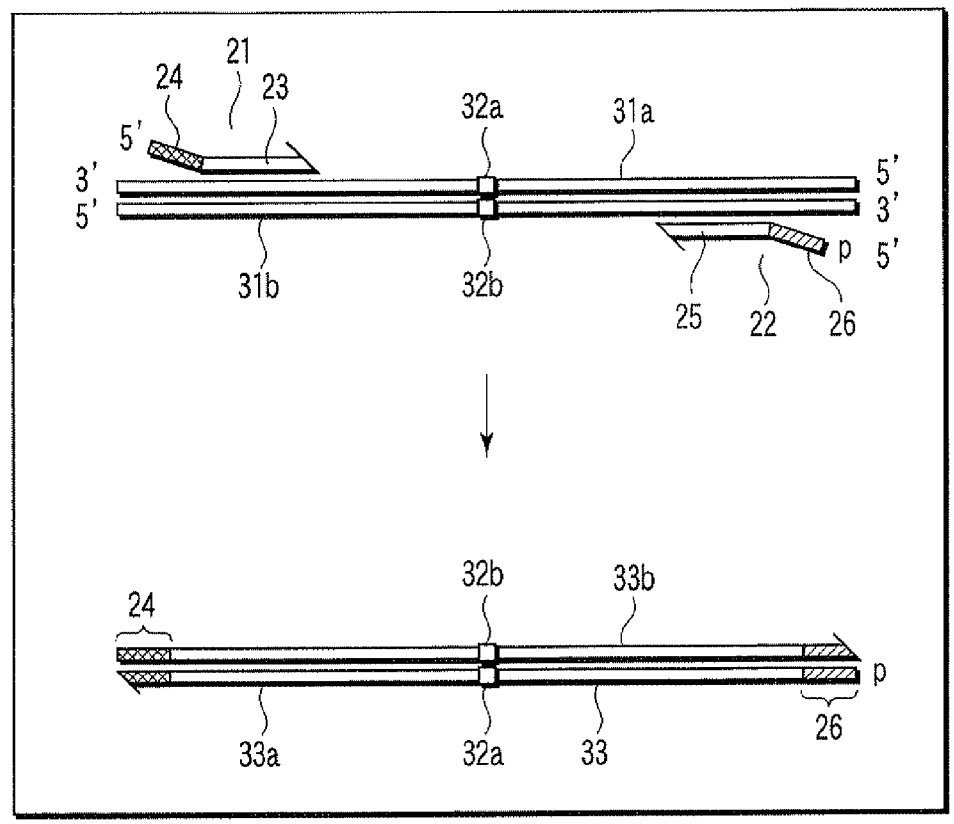
FIG. 3 is a chart showing an aspect of the present invention.

See FIG. 3. A nucleotide sample 31 is a double-stranded chain of a first single-stranded nucleotide 31a and a second single-stranded nucleotide 31b. The nucleotide sample 31 has a first detecting site 32a and a second detecting site 32b.

The first primer sequence 23 and the second primer sequence 25 bind respectively to suitable sites of the nucleotide sample 31. In such a case, the first primer sequence 23 binds to the 3'-sided sequence of the detecting site 32a of the first nucleotide sample 31a. Similarly, the second primer sequence 25 binds to a suitable site of the second nucleotide sample 31b, i.e., the 3'-sided sequence of the detecting site 32b of the second nucleotide sample 31b.

Then, the reaction is carried out under a condition allowing nucleotide elongation, preferably under a condition allowing nucleotide amplification, to obtain a double-stranded chain 33 containing a detecting chain 33a and a single-stranded chain 33b complementary thereto. The 5'-terminal-phosphorylated detecting chain 33a is then converted to a single-stranded chain, and, when the base of the detecting site agrees with the intramolecular detection probe, a cyclic structure is formed by ligation in intramolecular hybridization.

The length of the first or second intramolecular detection probe for use in the present invention may be 5 to 30 bases, preferably 10 to 20 bases and the probe preferably hybridizes at a temperature of 30° C. to 60° C. suitable for the binding reaction by a common ligase and a heat-resistant ligase. The sequence of the complementary chain of the first primer sequence should be so selected that it hybridizes to the sequence downstream of the sequence of the detecting site of the detecting chain. The length of the first or second primer sequence is preferably approximately 15 to 60 bases, and the primers preferably hybridize in a temperature range of 40° C. to 72° C., which is suitable as the annealing temperature in the PCR by using a heat-resistant polymerase. The second primer has an intramolecularly-detecting probe sequence complementary to the sequence to be detected close to the SNP nucleotide, i.e., detecting-site sequencer at the 5' terminal, and the 5' terminal is phosphorylated additionally. The first primer sequence has a sequence identical with the upstream sequence close to the SNP on the detecting site of the detecting chain.

The "condition allowing nucleotide elongation" in the present description may be any known condition allowing nucleotide elongation, but the condition suitable, more suitable, or most suitable, for the elongation reaction may be selected arbitrarily by those who perform the present invention. For example, the condition allowing nucleotide elongation contains the suitable primer according to the present invention, any known enzymes for nucleotide elongation, any known buffer components for adjustment of the salt-concentration balance of reaction solution, a dNTP mixture, and the like, and is under an environment kept to a temperature suitable for the elongation reaction. The term "elongation" used here may be any elongation known to those who are skilled in the art, and thus, may be an amplification method of repeating elongation reactions, and such amplification methods include PCR, asymmetric PCR, and the like.

(2) Method of Detecting SNP by Ligation by Using the Detecting Chain Prepared

An embodiment of the method of detecting SNP by using the intramolecular detecting sequence will be described more in detail. In the embodiment, the method of detecting SNP in human genome according to the present invention will be described.

An example of using the first intramolecular detecting sequence 5 and the second intramolecular detecting sequence 6 shown in FIG. 1 will be described. The length of the primer sequence contained in these first and second intramolecular detecting sequences 5 and 6 is approximately 30 bases, and the length of the first intramolecularly-detecting probe sequence 24 or the second intramolecularly-detecting probe sequence 26 is preferably approximately 15 bases. The stability of the hybrid varies as the length of the primer sequence or the intramolecularly-detecting probe sequence varies, and the first intramolecularly-detecting probe sequence 24 and the second intramolecularly-detecting probe sequence 26 hybridize to their respective complementary sequences, making the PCR resistant to inhibition during PCR. In addition, the SNP on the detecting chain and the 3'-sided sequence of SNP are allocated selectively to the first intramolecularly-detecting probe sequence 24 of the first intramolecular detecting sequence 21. Alternatively, the second intramolecularly-detecting probe sequence 26 of the second intramolecular detecting sequence 6 is preferably a sequence complementary to the 5'-sided sequence of the SNP on the detecting chain. The primer sequence 23 of the first intramolecular detecting sequence 21 is preferably a 5'-sided sequence downstream of the SNP on the complementary chain of the detecting chain. The primer sequence 25 of the first intramolecular detecting sequence 22 is preferably a 5'-sided sequence downstream of the SNP on the detecting chain. In addition, the 5' terminal of the second intramolecular detecting sequence 22 is preferably modified with phosphoric acid.

By using these first and second intramolecular detecting sequences, PCR is performed with about 10 to dozens of ng of genome DNA, as long as it is a human gene, as its template. Commonly used Taq polymerase may be used in PCR, but the polymerase is not limited thereto, and any known enzyme may be used if it is a heat-resistant enzyme. PCR for about 30 to 40 cycles gives a PCR product having the detection sequences at both terminals one of which carries a phosphate group at the 5' terminal of the detecting chain as shown in FIG. 3.

It is possible to carry out the next intramolecular detecting reaction at relatively high temperature, for example, by using a heat-resistant ligase such as Taq ligase. The reaction may be carried out at low temperature that may cause non-specific hybridization more frequently, for example, by using a non-heat-resistant T4 ligase, as long as the reaction certainly proceeds, specifically to the target sequence in the closed-ring product. For intramolecular detecting reaction, the PCR product is collected from the PCR reaction solution obtained in the previous step and mixed in a buffer suitable for ligase reaction. Then, the reaction is carried out, for example, in a PCR thermal cycler that allows control of a wider range of temperature. In thermal cycling, a double-stranded chain is first denatured in a high temperature process of converting the detecting chain into a single-strand chain at around 95° C.

(FIG. 4(4A)), giving an intramolecular structure shown in FIG. 4(4B), which is then annealed and ligated by a ligase as shown in FIG. 4(4C).

Annealing and ligation may be performed at different temperatures, and the thermal cycling including a denaturation step similar to that in PCR may be repeated several to dozens of times. The temperature may be gradually increased along the progress of the thermal cycling. It is possible to obtain high accuracy in the step, by identifying mismatched hybrids by ligase.

As shown in FIG. 5(5A), when the detecting chain does not have a base complementary to the SNP nucleotide at the 3' terminal, the detecting chain is not ligated with the ligase. In contrast, when the region is complementary as shown in FIG. 5(5B), the detecting chain is ligated by the ligase into a terminal-unexposed closed-ring structure, thereby forming a cyclic structure.

After the intramolecular reaction, the reaction mixture may be subjected as needed to a straight chain-digesting reaction of decomposing the primers, genomic DNA, unreacted detecting chains, complementary chains of detecting chain, and others remaining in the reaction solution. In the reaction, the reaction mixture was decomposed at a constant temperature after a nucleotide-digesting enzyme such as exonuclease I or III is added to the intramolecular detecting reaction solution above and the buffer solution conditions, such as salt concentration, addition of denaturing agent, and pH value, are adjusted as needed. The used enzyme such as nuclease may be inactivated for sure by treatment at 95° C. for about 10 minutes after completion of the straight chain decomposition.

Then as shown in FIG. 6, the product in a cyclic structure 63 is then subjected to PCR by using a first primer 61 and a second primer 62. The first primer 61 may be a complementary chain of the first primer sequence 23, and the second primer 62 may be a complementary chain of the second primer sequence 25. When there is a desirable SNP, the intramolecular reaction leads to ring closure and gives an amplification product. Part of the reaction solution containing the closed ring is subjected to normal PCR amplification after straight chain decomposition. The primer used is preferably designed to give an amplification product containing a ring-closed connecting region. For example, the amplification product easily produced has a base length of approximately 1,000 or less, and any other sequence may be selected to give such an amplification product. When the amplification step is carried out in a real-time PCR apparatus, the next detection step may be eliminated.

Finally, the products may be analyzed to determine whether there is a desirable SNP present, for example, by electrophoresis, for detection of the PCR products having a desirable length. A quantitative PCR may be used as the PCR above for confirmation of the PCR products. The electrophoretic gel may be a common slab gel, or alternatively, capillary electrophoresis may be performed instead. Any one of known electrophoretic gels such as agarose and polyacrylamide may be used as the material for the gel. Any matrix may be used, as long as it has a molecular sieving effect and is suitable for electrophoresis. Use of a fluorescent intercalator such as ethidium bromide or SYBR Green for dyeing DNA is also preferable.

4. SECOND ASPECT

Preparation of Detecting Chain by Gap Ligation

Figure 7:
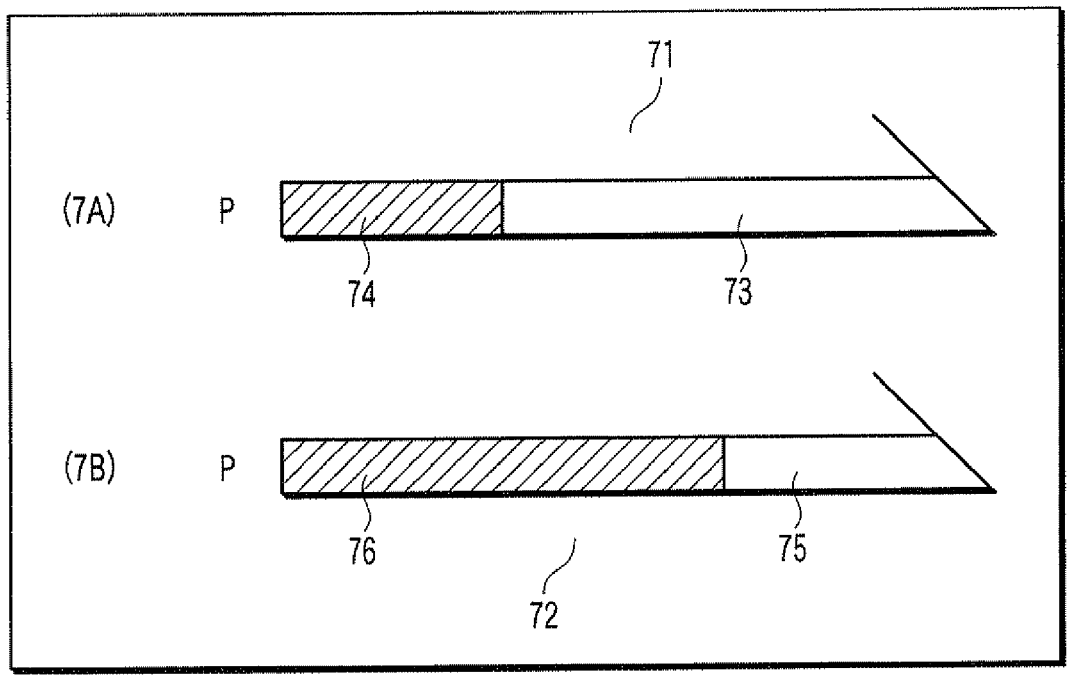
FIG. 7 is a chart showing an aspect of the present invention.

In the present invention, the following intramolecular detecting sequence for preparation of the detecting chain may be used. As shown in FIG. 7, the first intramolecular detecting sequence (7A) and the second intramolecular detecting sequence (7B) may be needed for intramolecular detection of SNP by ligation. The intramolecular detecting sequence 71 is used as a primer, while the intramolecular detecting sequence 72 is a nucleotide downstream of the primer that is ligated by ligase at the end point of producing the complementary chain by polymerase. Both sequences are part of the detecting chain. The intramolecular detecting sequence 71 has an intramolecularly-detecting probe sequence 74 at the 5' terminal. The sequence is complementary to the sequence of the upstream detecting site close to the SNP on the detecting chain produced by the primer 71, and its 5' terminal is phosphorylated. The 3'-terminal primer sequence 73 is a sequence located upstream of the detecting-site sequence of detecting chain. The length of the primer sequence 73 is preferably approximately 15 to 60 bases, and the primer sequence 73 is not particularly limited as long as it hybridizes at a temperature in the range of 40° C. to 72° C., which is suitable as the annealing temperature in the PCR reaction by using a heat-resistant polymerase. The intramolecular detecting sequence 72 has an intramolecularly-detecting probe sequence 75 at the 3' terminal, and is identical with the sequence downstream of the sequence detected by the detecting chain. The 5' terminal is phosphorylated.

Figure 11:
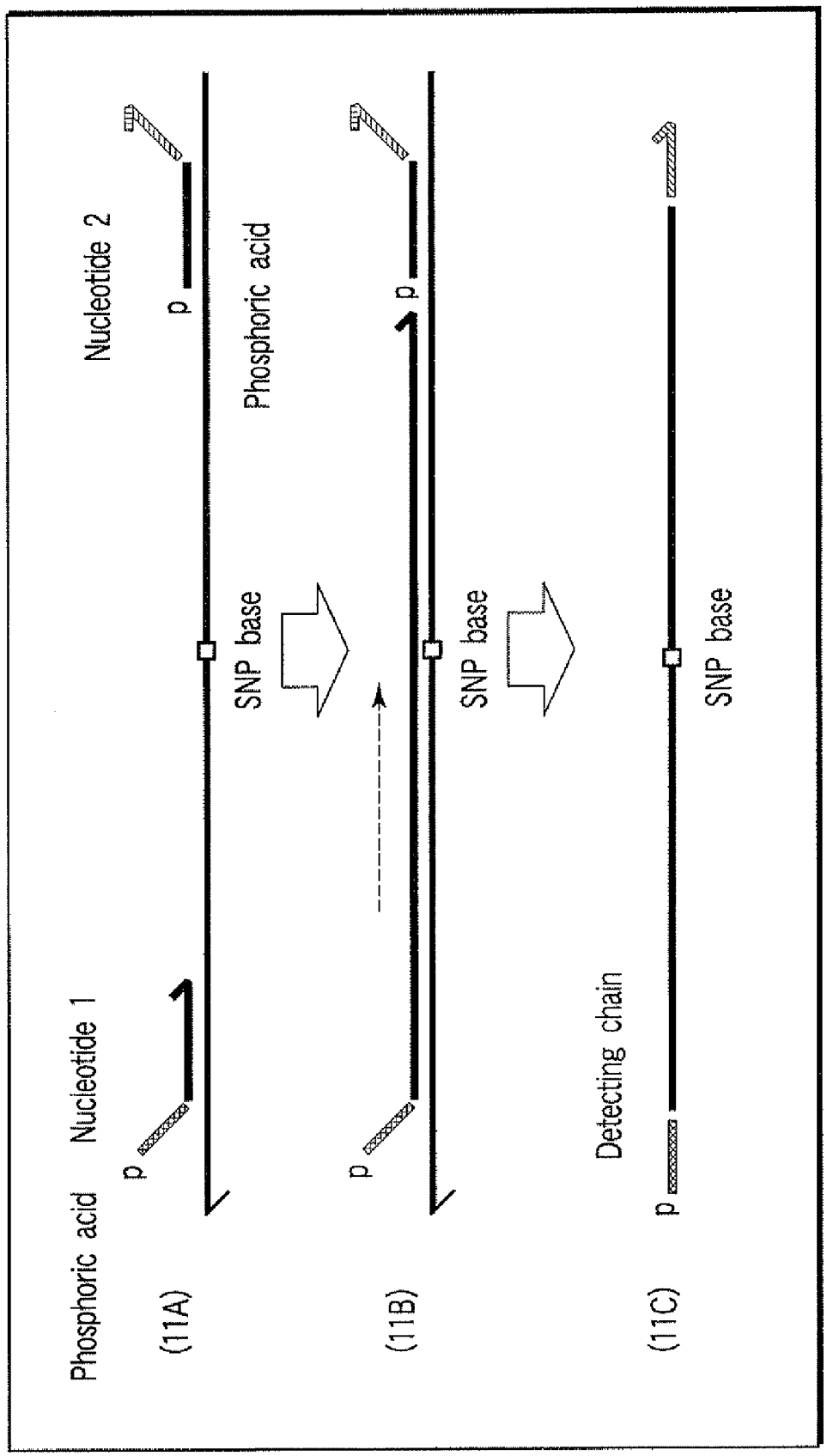
FIG. 11 is a chart showing an aspect of the present invention.

When a method of producing a single strand according to the present invention is used, a nucleotide having detection probes at both terminals (FIG. 11(11A)) is produced as a single-stranded chain (FIG. 11(11B)). Such a method is advantageous, because the nucleotide produced is not a double-stranded chain, as when detection probes are bound to both terminals of the nucleotide containing an analyte sequence in PCR amplification, and there is no inhibition by reassociation of nucleotides during intramolecular hybridization.

5. THIRD ASPECT (1) Preparation of Detecting Chain by Gap Ligation

Figure 8:
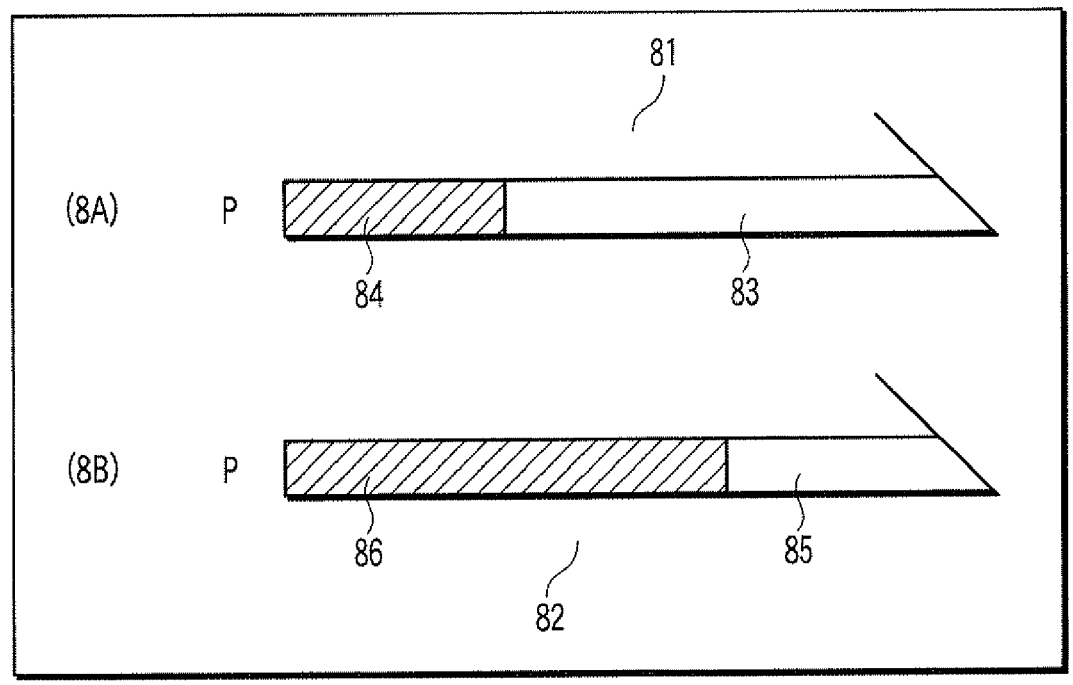
FIG. 8 is a chart showing an aspect of the present invention.

According to the present invention, the following intramolecular detecting sequence for production of the detecting chain may be used. For example, use of the following intramolecular detecting sequence in detection of single nucleotide polymorphism will be described below. See FIG. 8. Unlike the case where the detecting chain is prepared by gap ligation (1), i.e., where the intramolecular detecting reaction is carried out by ligation, an intramolecular detection mutation primer sequence 85 having a 3'-terminal nucleotide complementary to the SNP nucleotide (FIG. 8(8B)) is used as the sequence equivalent to the second intramolecular detecting sequence 75 (FIG. 7(7B)). In the present embodiment, the sequence equivalent to the first intramolecular detecting sequence 74 (FIG. 7(7A)) is preferably a downstream connecting sequence 84 complementary to the sequence downstream of the SNP on the detecting chain. Each sequence is preferably approximately 15- to 40-base long, so that it can stably hybridize in a reaction solution at 30° C. to 72° C. or lower, which is suitable for the elongation reaction by polymerase.

The detecting chain may be produce by a method other than PCR. Nucleotides 1 and 2 having the structures shown in FIG. 10B are first prepared and allowed to hybridize with a sample DNA, for example a human genomic DNA. The analyte DNA is used in an amount, for example, of approximately 400 ng, if it is a human genome, which is much larger than the amount used in chain detection by PCR. The amounts of the nucleotides 1 and 2 used may vary according to the reaction temperature and the amount of analyte DNA, but may be the same as or larger than 1 mole of the analyte DNA. The concentrations of the nucleotides 1 and 2 may be the same as or different from each other.

The detecting-chain synthesis by gap ligation includes complementary chain synthesis by a polymerase by using the nucleotide 1 as a primer and ligation reaction between the 3' terminal of the complementary chain and the nucleotide 2 by a ligase. Both enzymes may be added to the reaction solution together for simultaneous progress of the reaction, or alternatively, the polymerase may be added first and then the ligase, after the polymerase reaction. A denaturation step of facilitating hybridization by denaturing at 95° C. and cooling the reaction solution rapidly to 4° C. may be used when the sample is a genomic DNA. A polymerase without strand displacement activity such as Klenow fragment or Taq polymerase is favorably used as the polymerase. The temperature of the polymerase elongation reaction is decided properly, based on the optimum temperature of polymerase and the melting temperatures (Tm) of the nucleotides 1 and 2. For example, when a Klenow fragment is used as the polymerase, the temperature is kept to approximately 37° C., and the melting temperature Tm of the nucleotide 1 is so designed to make the nucleotide hybridize efficiently and specifically. The temperature of the ligation reaction by ligase is determined properly according to the optimum temperature of ligase and the Tm of the nucleotide 2, favorably in the optimum temperature range of the ligase and 5 to 10° C. higher than Tm. The reaction time is preferably not longer than 90 minutes, because the ligase may be inactivated.

(2) Detection of SNP by Gap-Ligation Ring Closure

Figure 9:
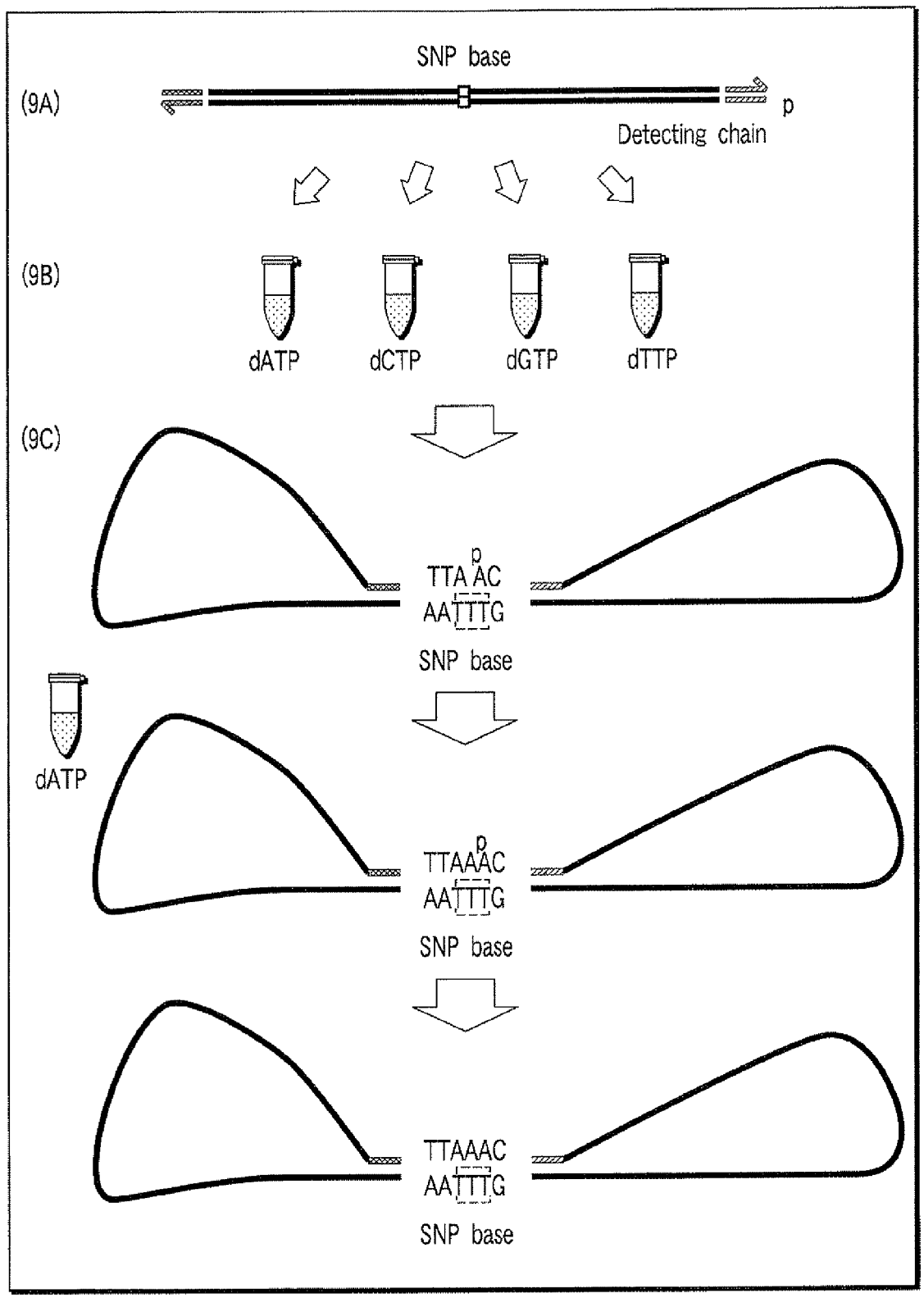
FIG. 9 is a chart showing an aspect of the present invention.

As in the ring-closure reaction of MIP method (Jpn. Pat. Appln. KOKAI Publication No. 2004-528016), the reaction solution is placed as divided in four containers, and dATP, dCTP, dGTP or dTTP is added separately to the solution in each container (FIG. 9(9B)). In this manner, gap ligation is performed while the base incorporated by the polymerase is limited to a single base (FIG. 9(9C)). The intramolecular detecting primer sequence then preferably has a sequence up to the SNP but not containing the SNP nucleotide at the terminal. Similarly to the primer and the connecting sequence by gap ligation, the length of the sequence then is preferably a length suitable for elongation reaction by polymerase allowing stabilized hybridization in a reaction solution at 30° C. up to 72° C., for example, approximately 15 to 40 bases.

The sequence thereof should be selected by calculation with commercially available structural calculation software such as Visual OMP (DNA Software) or Vienna Package available on the Web (University of Vienna, Inst. Theoretical Chemistry, http://www.tbiunivieacat/RNA/) not to make them have an unstable secondary structure at the reaction temperature and to make the reaction proceed rapidly. Alternatively, the sequence may be designed to hybridize to multiple positions and retain its reaction efficiency favorably for a long period, not by selecting the primer and the connecting sequence from the sequence around the desirable mutation, but by selecting a gene-specific sequence. For that purpose, such a gene-specific sequence may be selected, for example, by the tuple method (Japanese Patent No. 3610303) or the BLAST method (ALTSCHUL, S. F., Gish, W., Miller, W., Myers, E. W. & Lipman, D. J. (1990) "Basic local alignment search tool," J. Mol. Biol. 215: 403-410). Such means may be used in other aspects of the present invention.

In addition, after preparation of a detection chain, various nucleotide structures for intramolecular detection may be detected on one or more sequences in one reaction. In the method, multiple synthetic sequences may be incorporated into the detecting chain for detection of multiple sequences in one reaction solution, and the sequences to be detected are determined by the synthetic sequences. Such a method may be used in any one of the aspects of the present invention.

It is possible to determine the order of sequences easily, because such synthetic sequences are used in the present invention. The various detection nucleotides described in the present description are classified into sequences for preparation of the detection chain (such as primer and connecting sequences) and sequences for intramolecular reaction (such as intramolecularly-detecting probe sequence). When classified as above, a synthetic sequence is placed between the sequence for preparation of detecting chain and the sequence for intramolecular reaction. The synthetic sequence may be a sequence unique to the detection nucleotide. However, the number of the second intramolecularly-detecting probe sequences used for SNP detection is four at most, normally two, and two kinds of synthetic sequences may be allocated adequately to respective mutations during detection regardless of the position of SNP to be detected. If n SNPs having two kinds of alleles (wherein, $n \geq 2$), for example 100 SNPs, are to be detected simultaneously, it is possible to detect the SNPs with a total of n+2 kinds (e.g., 102 kinds) of synthetic sequences: two kinds of second intramolecularly-detecting probe sequences (i.e., intramolecularly-detecting mutation probe sequence, indicated by ASO in the figure) and n kinds, for example 100 kinds, of synthetic sequences for the first intramolecularly-detecting probe sequence (i.e., intramolecularly-detecting common probe sequence, indicated by LSP in the figure). Alternatively if n SNPs having four kinds of alleles are to be detected simultaneously, four kinds of alleles and n kinds of the synthetic sequences are needed, and specifically, for simultaneous detection of SNPs at 100 positions, it is possible to detect the desirable SNPs with 104 kinds of synthetic sequences.

A synthetic sequence may be used as a common sequence for amplification. Then, as shown in FIG. 10, an additional synthetic sequence may be introduced to the nucleotide 1. As described above, for detection of SNPs at 100 positions having 2 kinds of alleles, the upstream primer-sided synthetic sequence may be limited to a single kind of sequence as the common primer sequence, and 100 kinds of the LSO-sided synthetic sequences respectively corresponding to the SNP positions may be used. On the other hand, the number of the synthetic sequences for the nucleotide 2 may be only two, i.e., the number of the alleles. In this way, it is possible to PCR-amplify a sequence of two kinds of primers, a common primer sequence and an allele, connected to each other in intramolecular detecting reaction and thus, to detect mutation at each SNP.

The means may also be used in any aspect of preparing the detecting chain by gap ligation in the present invention, and the nucleotide 1 may be used as the first intramolecular detecting sequence, while the nucleotide 2 as the second intramolecular detecting sequence.

In the method of preparing a single-stranded sequence according to the present invention, a nucleotide having detection probes at both terminals (FIG. 11(11A)) is generated as a single-stranded chain (FIG. 11(11B)). Thus, the nucleotide generated is not a double-stranded chain, as when detection probes are connected to both terminals of the nucleotide including the analyte sequence during PCR amplification, and thus, is advantageous because there is no inhibition by reassociation of nucleotides during intramolecular hybridization.

6. FOURTH ASPECT

Adapter Ligation

FIG. 13 shows the structure of an adapter for preparation of a detecting chain by connection of an adapter to a restriction enzyme fragment. In the embodiment, shown are results of using a restriction enzyme 111 or 112 having a 5'-terminal-protruding cleavage terminal. Each of adapters 101 and 102 is mostly a double-stranded chain and partly has a single-strand chain. The adapter containing the 5' terminal of the detecting chain will be called adapter 2. Then, the adapter 101 has a complete double-strand intramolecularly-detecting probe sequence, and an adapter sequence forming a double-stranded chain by hybridization to a cleavage terminal by the restriction enzyme 1. In particular, the 5'-terminal of the sequence complementary to the intramolecularly-detecting probe sequence is not phosphorylated, and the 5' site of the adapter sequence is phosphorylated. On the other hand, the adapter 2 has a structure similar to that of the adapter 1, but has an adapter sequence that hybridizes to the cleavage terminal by the restriction enzyme 2, and the 5' terminal of the detecting chain is phosphorylated. The adapter-sided 5' terminal may be or may not be phosphorylated. During intramolecular detection of SNPs, it is preferable to select a sequence having a base complementary to the SNP nucleotide to be detected at the 3' terminal of the intramolecular detection probe of the 3' detecting chain, and the intramolecularly-detecting probe sequence at the 5' terminal of the detecting chain preferably has a complementary sequence at the position upstream of the SNP nucleotide of the sequence to be detected.

An example of adapter ligation by using the adapter shown in FIG. 13 is shown in FIG. 14.

First, an analyte sample 141 is treated with the restriction enzymes 1 and 2. The analyte sample 141 is then cleaved at a site 142a by the restriction enzyme 1 and at a site 142b by the restriction enzyme 2. Then, the adapter 1 is bound to the cleavage site by the restriction enzyme 1, and the adapter 2 to the cleavage site by the restriction enzyme 2. The adapter 1 forms a site 143a and the adapter 2 forms a site 143b by binding. A single-stranded chain 144b phosphorylated at the 5' terminal forms an intramolecular structure, giving a cyclic structure 145. Thus, the cyclic structure 145 may be detected by any known means.

The both terminals of the restriction-enzyme fragment containing the target SNP may be cleaved only by the restriction enzyme 1 or 2, depending on the restriction enzymes 1 and 2 selected. Care should be given to selection of the restriction enzymes, because the positional relationship between the restriction enzymes 1 and 2 may possibly be reversed from that desirable.

7. FIFTH ASPECT

Detection Method by Electrophoresis

Assuming that a closed-ring nucleotide is obtained according to the presence of the target sequence in any one of the aspects above, an aspect of the method of detecting the closed-ring nucleotide by electrophoresis will be described. Generally when compared with a straight-chain DNA having the same molecular weight in gel electrophoresis, the electrophoretic mobility of a cyclic nucleotide or plasmid is larger than that of a straight chain. It is possible to determine, by gel electrophoresis, whether a closed-ring nucleotide is generated by using the characteristic above.

A method of detecting a partial sequence by amplification of the partial sequence of the cyclic nucleotide obtained by the method according to the present invention will be described. As for (2) of the third aspect, when a synthetic sequence primer placed next to the second intramolecularly-detecting probe sequence is labeled with a fluorescent dye, it is aligned with a synthetic sequence primer placed next to the first intramolecular detection probe, holding a closed-ring region inside, and the mixture is amplified by PCR, an amplification product is obtained. For example, an additional sequence of several bases showing the position and length of the desirable SNP, preferably a tail sequence of approximately 5 bases for each SNP site, is bound to the 5' side of the primer placed next to the first intramolecular detection probe. More preferably, the dye for the fluorescence label of the second intramolecular detection probe-sided primer is preferably altered for each allele. Alternatively, the length of the primer is altered by addition of a tail sequence, while a common dye is used. Electrophoresis of the fluorescence-labeled PCR products thus obtained in an electrophoretic apparatus, such as ABI PRISM 3100 Genetic Analyzer manufactured by Applied Biosystems, allows differentiation of short chains accurately and gives peaks having a molecular weight corresponding to the SNP position and different in fluorescent color according to the allele, and thus, it is possible to read the typing results.

8. SIXTH ASPECT

Detection Method by Mass Spectrometry

The following means are used for detection by mass spectrometry in the present invention. As for (2) of the third aspect, a synthetic sequence primer placed next to the second intramolecularly-detecting probe sequence and a synthetic sequence primer placed next to the first intramolecularly-detecting probe sequence are amplified in such a manner that ring closure gives a PCR product, and the PCR product is detected in a mass spectrometer. For example, iPLEX system by Sequenom is favorable for mass spectrometric analysis of nucleotides.

The mass spectrometric peak positions of the PCR products, which contain the sequences around SNP, are unpredictable. For this reason, the peak positions are examined previously by mass spectrometer. In addition, the primer length is adjusted by addition of a tail sequence for differentiation of the mass peaks of the SNPs and alleles, so that each SNP has a different peak position and the alleles have a small difference in mass. In this way, it is possible to detect mutation easily by mass spectrometry in the present invention.

9. SEVENTH ASPECT

In another aspect of the present invention, provided is a kit for detecting nucleotide sequence.

The kit contains at least a first intramolecular detecting sequence containing a sequence complementary to the first sequence located at the 3'-side position of a detecting site contained in a nucleotide sample, and/or a second intramolecular detecting sequence containing a sequence complementary to the second sequence located at the 5'-sided position of the detecting site (wherein, at least one of the 3'-terminal nucleotide of the first intramolecular detecting sequence and the 5'-terminal nucleotide of the second intramolecular detecting sequence is so modified to bind to each other), and may contain additionally a buffer for desirable PCR, ligation reaction, digestion nucleate reaction and/or hybridization reaction, or the like, enzymes such as exonuclease I, exonuclease III, polymerase and/or ligase, a reaction container such as 384-well microplate, 96-well microplate and/or Eppendorf tube, a detection device such as microarray, and the like.

In another aspect of the present invention, provided is a method of producing a cyclic structure, in addition to the nucleotide sequence-detecting method above.

Also provided in the aspect of the present invention is means of detecting nucleotide sequence that is resistant to nonspecific reaction and allows operation at low cost.

II. Gene Mutation Analysis

In another aspect of the present invention, provided is a method of analyzing gene mutation.

Currently among the approximately 3,000,000 SNP sites described above, the number of the SNP sets related to sensitivity to a medicine or disease is considered to be hundreds or dozens at most. For example, it is possible to study a total of 31 sites by typing 29 alleles of gene CYP2D6 and two alleles of CYP2C19 with a SNP-typing microarray for a medicine sensitivity-related protein cytochrome P450 available from Roche. Thus, typing of thousands or tens of thousands of alleles will not be needed for diagnosis, but typing of dozens, a hundred and tens at most, of SNPs would be needed. Such a number of typing is too large for application of the Sanger's method. Accordingly, a method simpler in experiment procedure, such as SSCP method (single strand conformation polymorphism), SSP-PCR method (sequence specific primers-PCR), or real-time PCR analysis method by using a fluorescent TaqMan probe, is used. Each of these methods is a so-called "monoplext" detection method of studying the presence of a SNP allele in a single reaction tube. In the monoplex method, reaction containers in the number identical with that of SNPs are used, and a sample genomic DNA should be added to the respective containers. Accordingly, the number of the samples simultaneously processed is limited, and the quantity of the sample genomic DNA should be larger.

In contrast to the monoplex methods, mutiplex methods were proposed in late 90's. The microarray for detection of SNPs in cytochrome P450 protein available from Roche may be called a multiplex method, because the SNP is detected in reaction in a single reaction container. However, in addition to the Roche method, more complicated and more flexible detection methods have been proposed.

One of the methods is a multiplex method. It is a method of transforming a natural gene sequence into a synthetic sequence and identifying and/or detecting the transformed artificially designed sequence. The key of the multiplex method is an artificially designed sequence region called tag. In the method, multiple genes are transformed into tags individually as previously allocated, and thus, multiple genes are detected in the same solution. Accordingly, the target gene is detected with a transformed tag. The following two factors are important in designing the tag. One is that the tags react independently and do not hybridize crosswise. The other is that the tags used for simultaneous reaction in the same solution have melting temperatures (i.e., Tm) similar to each other. Detection of individual gene sequence by using a tag is different from detection by using a complementary probe, in that the same series of tags may be used in the detection phase. Thus, it is a flexible method allowing use of the same detection method and/or the same detection device even when the target detection gene is altered.

For example, Barany et al. in Cornell University developed a LDR (ligase detection reaction) method as such a method. The method is combination of a SNP-detecting method by using ligase and a method of transforming a gene into a tag called zip-code. As a result, multiple SNPs are detected in the same reaction solution. Such a system is commercialized as a detection kit SNPlex from ABI (Jpn. Pat. Appln. KOKAI is Publication Nos. 2000-511060, 2001-519648, and 2004-526402).

Alternatively, Orchid Cellmark developed a so-called SNP-IT method of carrying out a detection reaction in a single reaction solution and identifying 48 kinds of alleles with a microarray placed at the bottom of a microplate (Japanese Patent No. 3175110, Jpn. Pat. Appln. KOKAI Publication No. 2002-508664).

The method currently considered most successful is a method provided from Illumina. It is a method of detecting approximately 1,500 kinds of zip-code sequences at maximum simultaneously by detecting SNPs after processing in a polymerase elongation reaction and a ligase-ligation reaction in its original detection device, a system similar to microarray (called Bead Array), and transforming desirable sequences into zip-code sequences (Jpn. Pat. Appln. KOKAI Publication Nos. 2002-519637 and 2003-521252).

TM Bioscience provides a multiplex reaction kit allowing detection by using Luminex fluorescence-colored beads (Jpn. Pat. Appln. KOKAI Publication Nos. 2004-522440 and 2004-526433). The system is supplied as a genetic disease-detecting kit for the research purpose.

In such a method, transformation of a gene into a tag is essential. Currently, the reactions used for the transformation include ligase ligation reaction (OLA: oligonucleotide ligation assay), one-base elongation by polymerase, and the like. In each of the methods, the potential of an enzyme identifying mismatched hybrid is used to the maximum degree. In the ligase reaction, the probe sequence is so determined that the SNP base is bound to the 3' terminal of the probe to be connected (Luo, J. et al, Nucl. Acids Res. 24, 3071-78 (1996)).

Parallele provides an MIP method (molecular inversion probe). It is a multiplex typing method using a tag higher in reaction efficiency and a closed-ring probe and a gap ligation method that is lower in probe-producing cost (Hardenbol, P. et al., Nat. Biotechnol. 21, 673-678 (2003), Hardenbol, P. et al., Genome Res. 15, 269-675 (2005))

Along with development and commercialization of many multiplex methods, DNA computing is a method that may cause drastic change in gene detection. The DNA computing was first proposed by Adelman of University of Southern California in 1994. It is a report on an experiment to solve a combination problem that is difficult for computer by reaction of DNA. The report showed that it was possible to calculate by using DNA, at a speed faster and at energy consumption far lower than those of computer, depending on the problem. However, results on DNA computing research since the report led to progress of the method of designing an artificially designed sequence having smaller in error, i.e., less cross-hybridizable from the viewpoint of gene test, and sequences having similar reactivity, i.e., having similar Tm values, and to an idea of calculating with genes, because the calculation is performed with DNA itself.

Suyama et al., in Japan, who found the possibility of applying the DNA computing technology to gene analysis, focused on the availability of the artificially designed sequence obtained by studies on the DNA computing technology, and proposed a multiplex detection method of transforming natural gene sequences into artificially designed sequences similar in characteristics, as disclosed in Japanese Patent No. 3103806 and WO 01/025481 pamphlet. As disclosed in Jpn. Pat. Appln. KOKAI Publication No. 2002-181813, they also proposed a method of analyzing a gene by logical operation with artificially designed sequence extracted as correlated with a gene, i.e., logical operation with gene, and identifying combinations of disease-related SNPs without use of a computer. As disclosed in Jpn. Pat. Appln. KOKAI Publication No. 2002-318992, they also proposed a hybrid architecture of a DNA computer and the shape and the experiment method when the DNA computer is applied to gene expression and analysis almost at the same time. The multiplex detection probe proposed by Suyama et al. includes two probes called anchor probe and adapter probe. Artificially designed sequences and priming sequences for amplification thereof are placed densely in the adapter probe side, during expression analysis. Unlike the probe structure for the multiplex methods described above, the probe does not contain any gene sequence between primers, and thus, there is almost no difference between amplification characteristics of respective artificially designed sequences.

After these pioneering studies, Mills in the U.S. showed a possibility of using the DNA computing technology in gene expression and analysis (Mills, Trends Biotechnol. vol. 20: pp. 137-40 (2002)). Shapiro et al. in Israel showed basic experimental results for diagnosis of a disease by using logical operation by DNA computing in cancer cell and gene treatment according to the diagnosis results (Shapiro, et al., Nature. vol. 429: pp. 423-9. (2004)).

There is an increasing importance in the multiplex method allowing analysis of a number of items at low cost under such a technical trend, and many researches and developments aimed at reduction of cost, shortening of period, improvement in sensitivity, and increase in the number of test items are now in progress worldwide.

1. Gene Analysis Method Using Intramolecular Ligation Reaction (1). Explanation of Terms The term "gene" used below includes both the coding and non-coding regions of a genome. The present invention provides a method of analyzing and/or detecting gene mutation, but the method may be used favorably not only for gene mutation analysis but also to any analysis and/or detection of nucleotides.

The term "nucleotide" used below includes all DNAs and RNAs such as cDNA, genomic DNA, synthetic DNA, mRNA, entire RNA, hnRNA, and synthetic RNA.

The term "mutation" used below means gene polymorphism such as SNP and microsatellite sequence including repeating sequence, insertion, deletion and/or substitution of a base, combination thereof, or the like.

The "condition allowing nucleotide amplifications" in the present description may be any known condition allowing nucleotide amplification, but the condition suitable, more suitable, or most suitable for the amplification reaction may be selected arbitrarily by those who perform the present invention. For example, the condition allowing nucleotide amplification includes suitable primers according to the present invention, any known enzymes for nucleotide amplification, any known buffer components for adjustment of the salt concentration balance of reaction solution, a dNTP mixture, and the like, and is under an environment kept to a temperature suitable for the amplification reaction.

The term "amplification" used below may be any amplification known to those who are skilled in the art, and examples thereof include amplification methods such as PCR and asymmetric PCR.

The "priming sequence" used below is a sequence on the primer 3' terminal that hybridizes to a desirable nucleotide and extends nucleotide in the 3' direction under the condition allowing nucleotide amplification.

The "artificially designed sequence" used below means an artificially designed sequence. The artificially designed sequence may be designed arbitrarily according to the purpose of the user and for a particular purpose. For example, the artificially designed sequence for use in the present invention may be used for identification and/or amplification.

The term "3' side of the mutation" used below may mean only the mutation site itself, the mutation site and a nucleotide at the 3' side, for example, having 1 to 5 bases, or a nucleotide at the 3' side of the mutation site excluding the mutation site, for example, having 1 to 5 bases, but the number of the bases is not limited to the number above, and may be 6 to 10. The length of the probe sequence described below may also be considered.

(2). Summary

Figure 15:
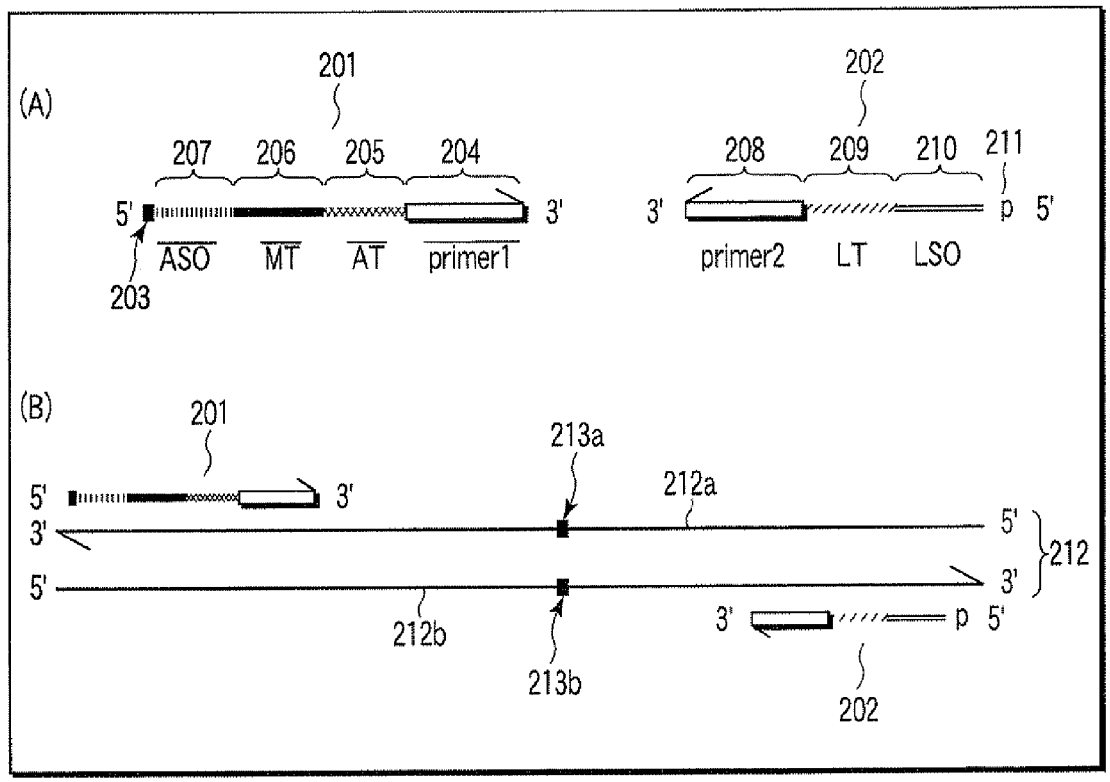
FIG. 15 is a chart showing an aspect of the present invention.

The summary of the present invention will be described, with reference to the aspect shown in FIGS. 15 to 17.

See FIG. 15A. An analyte nucleotide to be detected and two primers corresponding to the mutation to be detected, i.e., a first oligoprimer 201 and a second oligoprimer 202, are prepared (FIG. 15A) (the "oligoprimer" will be referred to simply as a "primer" in the present description). First, a region of the analyte nucleotide including the mutation site to be detected is amplified by using these two primers. The amplification will be called the first amplification. For example, the amplification may be performed by PCR, and, in such a case, the amplification may be called the primary PCR.

(i) Analyte Nucleotide

See FIG. 15B. In the present aspect, an analyte nucleotide 212 is a double-stranded nucleotide. It includes a first single-stranded nucleotide 212a and a second single-stranded nucleotide 212b. The second single-stranded nucleotide 212b includes mutation to be detected 213b. The first single-stranded nucleotide 212a includes a nucleotide 213a complementary to the mutation to be detected 213b.

The sequence to be analyzed in the present aspect is the mutation nucleotide to be detected 213b. Thus, analysis results on the final mutation and information on presence of mutation and others are related to the mutation nucleotide to be detected 213b.

The analyte nucleotide may be a genome nucleotide, a nucleotide derived from any gene, or a synthetically prepared nucleotide. The definition of the nucleotide is described above.

Hereinafter, a method of analyzing an analyte nucleotide of double-stranded nucleotide will be described as an example, but the analyte nucleotide may be a single-strand chain in the present invention. Because, even when the analyte nucleotide is, for example, a single-strand chain, the chain of the absent side are also produced from the priming sequence of the first or second primer in the first thermal cycling when the first amplification is performed for example by PCR. Thus, the reaction proceeds as if there was a double-strand analyte nucleotide from the beginning.

(ii) First Oligoprimer

See FIG. 15B. The first oligoprimer 201 is so designed that it hybridizes to the continuous sequence in a region of the second single-stranded nucleotide 212b. It is thus designed that part of the first oligoprimer 201 is complementary to part of the second single-stranded nucleotide 212b.

See FIG. 15A for details. In the present embodiment, the first oligoprimer 201 has four regions. A first priming sequence 204 (indicated by "primer 1" with top line in the figure) is present in the most 3'-terminal side. The first priming sequence 204 is complementary to part of the second single-stranded nucleotide, and after hybridization, it plays a role as a primer under a suitable condition.

A first probe sequence 207 (indicated by "ASO" with top horizontal line in the figure) is placed at the most 5' side of the sequence bound to the first priming sequence 204. In the present aspect, the most 5' terminal of the first probe sequence 207 contains a nucleotide 203 homologous to the nucleotide to be detected, the nucleotide 213b. Presence of the first probe sequence 207 enables the information on the mutation to be detected and/or analyzed to be reflected in the artificially designed sequence described below.

In the case of the first oligoprimer 201 used in the present embodiment, two kinds of artificially designed sequences are connected. A first artificially designed sequence 206 (indicated by "MT" with top horizontal line in the figure) is placed at the 3' side of the first probe sequence 207. A second artificially designed sequence 205 (indicated by "AY" with top horizontal line in the figure) is placed at the 5' side of the first priming sequence 204.

Details of the terms, purposes and functions of the artificially designed sequences "AT", "MT" and "ASO" will be described below and omitted here.

The length of the probe sequence 207 is not particularly limited, and is 10 to 30 bases, preferably 15 to 25 bases.

The first artificially designed sequence 206 and the second artificially designed sequence 205 are artificially designed sequences carrying information about the analyte mutation site 213b. For example, at least one of them may be a sequence corresponding to the gene mutation of the analyte mutation site 213b, or at least one of them may have a role as a tag identifiable during detection. They may be sequences artificially designed to carry information about the mutation site. The length of the artificially designed sequence is 5 to 30 bases, preferably 10 to 25 bases. The length of the multiple artificially designed sequences contained in one oligoprimer may be the same as or different from each other.

Also in the present embodiment, the number of the artificially designed sequences contained in the first oligoprimer is 2, and that of the probe sequence is 1, but the numbers are not limited thereto, and the number of the artificially designed sequences may be 1 or more, or alternatively, the oligoprimer may contain no artificially designed sequence and contain only a probe sequence. The lengths of the multiple artificially designed sequences and the probe sequences contained in an oligoprimer may be the same as or different from each other.

See FIG. 15B. The first priming sequence 204 is complementary to the partial sequence of the first single-stranded nucleotide 212a, and these sequences hybridize to each other, but the position is the 3' side of the mutation site 213a of the first single-stranded nucleotide. In the first PCR amplification, the first single-stranded nucleotide 212a and the first oligoprimer 201 hybridize to each other only in the region of the first priming sequence 204.

(iii) Second Oligoprimer

See FIG. 15B. The second oligoprimer 202 is so designed that it hybridizes to the second single-stranded nucleotide 212b.

See FIG. 15A. The 5' terminal of the second oligoprimer 202 is phosphorylated 211. The sequence at the 5' terminal is the second probe sequence 210, and there is an artificially designed sequence 209 (indicated by "LT" in FIG. 15A) at the 3' side thereof, and a second priming sequence 208 at the 3' side thereof. The term "LT" will be described below in detail.

See FIG. 15B. The second probe sequence 210 is a sequence homologous to the partial sequence close to the 3' side of the mutation site 213b on the second single-stranded nucleotide 212b. The length of the probe sequence is not particularly limited, but is 10 to 30 bases, preferably 15 to 25 bases.

The artificially designed sequence 209 is a artificially designed sequence carrying information about the analyte mutation site 213b. It may be, for example, an artificially designed sequence carrying information on a mutation site. Alternatively, it may be a sequence corresponding to gene mutation of the analyte mutation site 213b, or may have a role as a tag identifiable during detection. The length of the artificially designed sequence is 5 to 30 bases, preferably 10 to 25 bases.

Also in the embodiment above, the number of the artificially designed sequences contained in the second oligoprimer is 1 and that of the probe sequences is 1, but the numbers are not limited thereto, and the number of the artificially designed sequences may be 1 or more, or the oligoprimer may contain no artificially designed sequence and contain only a probe sequence. The lengths of the multiple artificially designed sequences and probe sequences contained in an oligoprimer may be the same as or different from each other.

See FIG. 15B. The second priming sequence 208 is complementary to a partial continuous sequence in the second single-stranded nucleotide 212b and these sequences hybridize to each other. The position is the 3' side of the mutation site 213b of the second single-stranded nucleotide. In the first PCR amplification, the second single-stranded nucleotide 212b and the second oligoprimer 202 hybridize to each other only in the region of the second priming sequence 208, allowing elongation and amplification of the nucleotide chain.

(iv) First PCR Amplification

An analyte nucleotide 212 is amplified (first PCR amplification) under a condition allowing nucleotide amplification by using the first oligoprimer 201 and the second oligoprimer 202 described above. A first PCR amplification product 220 thus obtained is shown in FIG. 16. The first PCR amplification product 220 contains a 5'-terminal phosphorylated nucleotide (second single-stranded nucleotide 222) and an unphosphorylated nucleotide (first single-stranded nucleotide 221) (FIG. 16).

(v) Intramolecular Hybridization

The first PCR amplification product 220 obtained in (iv) above is denatured into a single-strand chain (FIG. 17A). Any known conventional method may be used for denaturation from double-stranded chain to single-strand chain. Ligation reaction by using an enzyme such as ligase under a suitable condition after denaturation results in intramolecular hybridization.

At this time, the first single-stranded nucleotide 221 produced by denaturation of the first PCR amplification product, which is not phosphorylated at the 5' terminal, does not react in the intramolecular hybridization, and remains in its straight-chain shape (FIG. 17B). On the other hand, the 5' and 3' terminals bend toward the mutation site base 231, in the 5'-terminal phosphorylated second single-stranded nucleotide 222; the mutation site base 231 and the complementary base 232, the probe sequence 207 and the complementary chain 226, and also the second probe sequence 210 and the complementary chain 230 hybridize to each other; and additionally, the nick between the nucleotide 232 and the second probe sequence 210 is connected by a ligase, forming an intramolecular structure; and thus, the second single-stranded nucleotide 222 is converted into a closed-ring product. In this way, a closed-ring nucleotide molecule is obtained (FIG. 17C).

(vi) Second PCR Amplification

Subsequently, second PCR amplification of the region 233 in the closed-ring product obtained above, i.e., the second double-stranded nucleotide 222, is performed by using an artificially designed sequence 209 and an artificially designed sequence 234, which is a chain complementary to the artificially designed sequence 205, as primers under a condition allowing nucleotide amplification. At this time, one or both of the primers used may be labeled with an identifiable labeling substance. For example, the artificially designed sequence 234 may be used as a labeled primer.

(vii) Detection

It is possible to obtain information about the analyte mutation site 231, the mutation to be detected, contained in a second PCR amplification product 235 obtained by amplification above, by detecting an identifiable labeling substance 241. The information about the analyte mutation site 231 may be obtained, for example, by detecting the labeling substance 241 after recovery of the mutation site with a probe complementary to any probe sequence or any artificially designed sequence contained in the second PCR amplification product 235. In this way, it becomes possible to perform analysis on the mutation to be detected.

As described in the basic aspect above, the method according to the present invention characteristically includes first PCR amplification, intramolecular hybridization, second PCR amplification, and detection and/or analysis. As shown in the aspect of the present invention, provided is a nucleotide-analyzing method higher in reaction efficiency and detection sensitivity that allows detection easily with a small amount of sample.

FIG. 18 shows an oligoprimer set favorably used in the present invention. Oligoprimers used in the method described above are a first oligoprimer 201 and a second oligoprimer 202 in FIG. 18A. In an aspect of the present invention, the first oligoprimer containing no base complementary to the analyte mutation site base at the 5' terminal may be used. Examples thereof include first oligoprimers 243, 245 and the like (FIGS. 18B and 18C). The probe sequences in such a case are shown in the figures, as indicated with "LSO 1" with top horizontal line. The term will be described below.

Also in the embodiment above, the first oligoprimer 201 contains artificially designed sequences 205 and 206, but it may contain only one or no artificially designed sequence. An example of the first oligoprimer containing only one artificially designed sequence is a first oligoprimer 248 (FIG. 18D). An example thereof containing no artificially designed sequence is a first oligoprimer 250. The second oligoprimers 202, 244, 246 and 249 contain one artificially designed sequence (indicated by "LT" in the figure, the term will be described below in detail), but may not contain any artificially designed sequence. An example thereof is shown as a second oligoprimer 251. The oligoprimer may contain an identifiable labeling substance or hapten for facilitating detection. Examples thereof include the first primer 250 and the second primer 251 in FIG. 18E.

(viii) Duplicated Chain

The term "duplicated chain" used below means a nucleotide obtained by preparation of the complementary chain of the analyte nucleotide or a nucleotide complementary to the complementary chain of the analyte nucleotide. Examples thereof include nucleotides 221 and 222 prepared by using the analyte nucleotide in FIG. 2 as a template.

(ix) Intramolecular Structure

The term "intramolecular structure" used below is a structure containing a double-stranded-chain hybrid in one nucleotide molecule. It is also called secondary structure.

(x) Nucleoside Monomer

Examples of the nucleoside monomers capable of forming a polynucleotide in polymerization reaction include deoxyadenosine 5'-triphosphate, deoxycytidine 5'-triphosphate, deoxyguanosine 5'-triphosphate, deoxythymidine 5-triphosphate, deoxyuridine 5'-triphosphate, adenosine 5'-triphosphate, cytidine 5'-triphosphate, guanosine 5'-triphosphate, thymidine 5'-triphosphate, uridine 5'-triphosphate, and the like. However, the nucleoside monomers are not limited thereto, and include similar artificially prepared substances containing a nucleoside that can be a substrate for enzyme.

(xi) Terminal

The nucleotides may or may not have a phosphoric acid group at the 5' terminal and an OH group at the 3' terminal. In addition, the nucleotide molecule may have a chemically active group capable of forming a covalent bond on the terminal sugar chain or base. In the present description, the "terminal" may also be referred to as "end".

Hereinafter, preferred embodiments of the present invention will be described in more detail, but it should be understood that the invention is not limited thereto.

2. Preferred Embodiments (1). Aspects of Detecting Single Nucleotide Polymorphism (SNP)

(1-1). Aspect of Detecting Mutation by Ligation Reaction

Hereinafter, a SNP-detecting reaction by using a sample DNA obtained by processing of human cell will be described. In the aspect, two primers shown in FIG. 15A are used as the primer for use in detection. In the present embodiment, the first oligoprimer 201 will be called an ASO (i.e., allele specific oligonucleotide) primer, while the second oligoprimer 202, a LSO (i.e., locus specific oligonucleotide) primer (FIG. 15A). Also in the present embodiment, an analyte SNP 213b is selected as the mutation to be detected, i.e., the nucleotide to be detected 213b. ASO 207 and LSO 210 are used as the probe sequences 207 and 210, while MT 206, AT 205 and LT 209 are used respectively as the artificially designed sequences 206, 205 and 209.

See FIG. 15B. The LSO primer 201 and the analyte SNP 213b are located on the same chain. The 5' terminal of the LSO primer 201 is modified by phosphorylation. In the figure, the sequences on the chain complementary to the chain 212b to be detected in SNP 213b are indicated with horizontal line. Any known means may be used for modification by phosphorylation. The arrow indicating an nucleotide is shown in the direction from 5' to 3' terminal. The priming sequences 204 and 208 may be selected from genome sequence, while the regions of the ASO 207 and LSO 210 may be selected from the sequences complementary or almost complementary with a mismatched base to the sequences close to the SNP 213b and SNP 213b.

When a mismatched base is inserted, for example, the base at the position separated by 4 or 7 bases from the 3' terminal is modified to become mismatched; preferably, the base at the position separated by 7 bases is modified; and the base at the position separated by 4 bases is modified if the identification efficiency is not sufficient. The position from the 3' terminal, the number of mismatching, and the base to be mismatched may be decided arbitrarily, and it is possible to detect mutation without error by lowering the hybrid nucleotide stability with the mismatched bases added. The position may be substituted with a synthetic base such as inosine, instead of being substituted with a mismatched base.

The base of the SNP 213b is placed at the 5' terminal of the ASO 207.

The term "AT" is an abbreviation of amplification tag, and is used for the sequence of amplification primer. The term MT is an abbreviation of "mutation tag" and is a sequence corresponding to gene mutation. The term "LT" is an abbreviation of locus tag and is a sequence corresponding to a mutation site.

In principle, the MT 206 sequence is determined according to the ASO 207 sequence, while the LT 209 sequence to the LSO 210 sequence. However, the LT 209 sequence may be a common sequence when all the MT 206 sequences are sequences different from each other in the respective ASO 207 sequences. When the LT 209 sequences are different at respective mutation sites, the MT 206 sequences are determined, according to the kinds of mutations at respective mutation sites, in the number of alleles of SNP.

Figure 19:
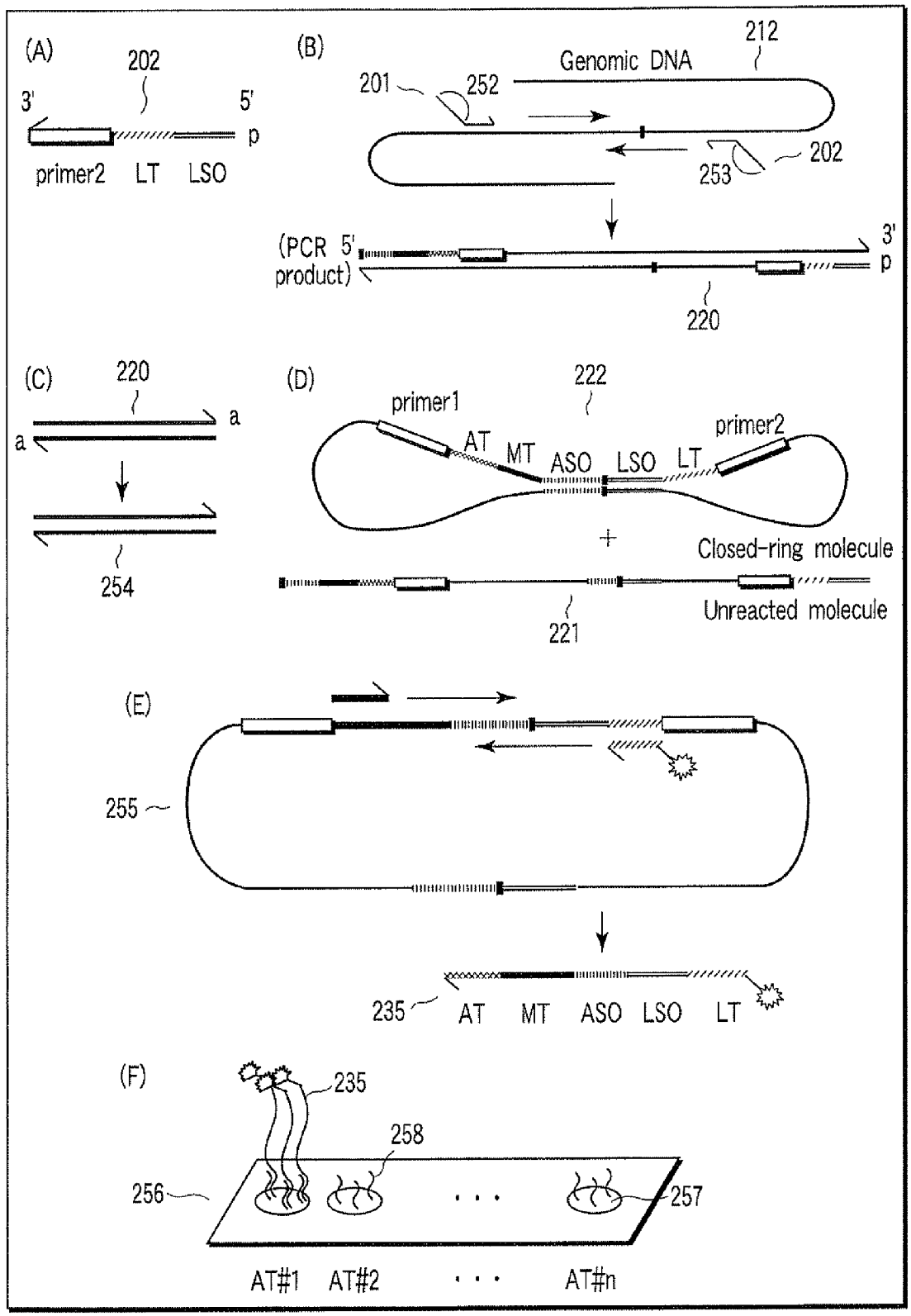
FIG. 19 is a chart showing an aspect of the present invention.

Hereinafter, the protocol in the present aspect will be described briefly, with reference to the scheme shown in FIG. 19. First, a 5'-terminal phosphorylated second primer, an LSO primer 202, is prepared (FIG. 19A).

In the first PCR, an analyte nucleotide containing a target SNP sequence 213b, a genome fragment 212, is first amplified (FIG. 19B) by using an ASO primer 201 and an LSO primer 202 as first primers. The number of the SNPs 213b to be amplified and/or detected with the ASO primer 201 and the LSO primer 202 may be one or more. However, a set of primers is used for detection of SNP at a single position, and the position of the SNP is to be decided at a particular site on the genome to be detected. Accordingly, when there are multiple SNPs, multiple primer sets are required.

Figure 16:
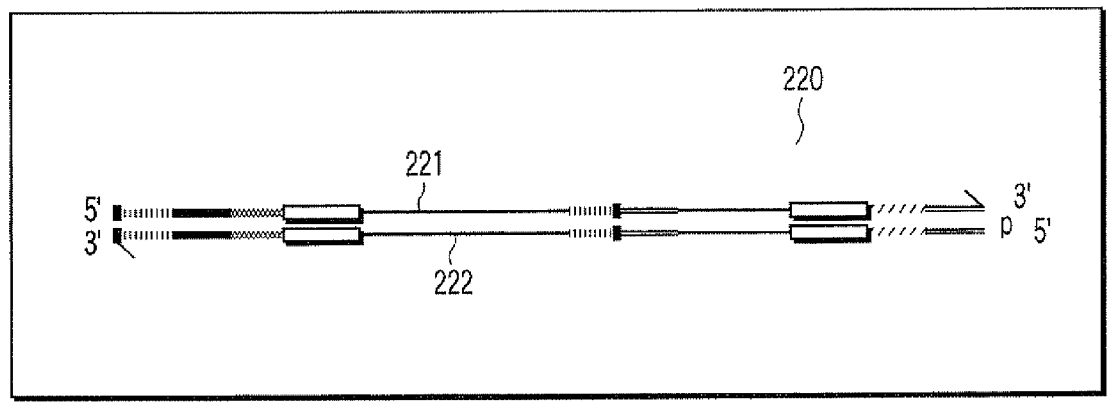
FIG. 16 is a chart showing an aspect of the present invention.
Figure 17:
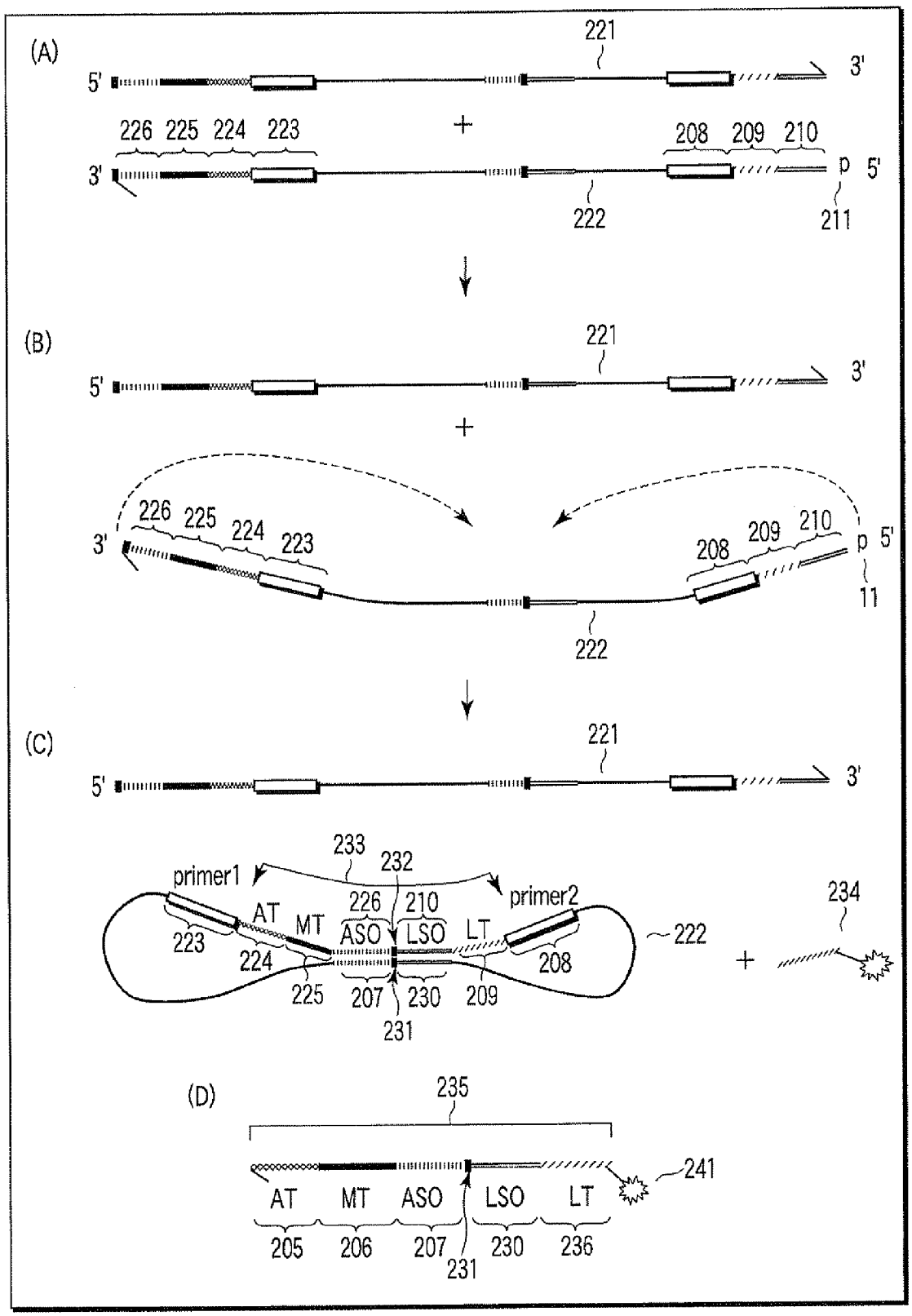
FIG. 17 is a chart showing an aspect of the present invention.

The product obtained by amplification is a first PCR amplification product 220 having the structure shown in FIG. 16. It is described as "PCR product 220" in FIG. 19B. A tag 252 region contained in the ASO primer 201 of FIG. 19B corresponds to the regions of the probe sequence 207 and the artificially designed sequences 206 and 205 shown in FIG. 15A, and plays a role as a tag. Similarly, a tag 253 contained in the LSO primer 202 corresponds to the regions of the probe sequence 210 and the artificially designed sequence 209 shown in FIG. 15A, and plays a role as a tag.

After the first PCR, the group "a" connected to the 3' terminal of the first PCR amplification product 220 is eliminated by processing in smoothing reaction (FIG. 19C). Here in the step, the nucleotide sticking out of the first PCR amplification product 220 is removed. Any enzyme may be used then, as long as it is an enzyme having an exonuclease activity in the direction from 3' to 5'. When a polymerase having a high proof-reading activity is used in the first PCR, the process, i.e., the smoothing reaction, may be eliminated.

A first PCR product 254 after the smoothing reaction is then subjected to intramolecular ligation reaction (FIG. 19D). Ligation reaction proceeds when there are sequences corresponding to ASO and LSO in the PCR product, giving a molecule 222 having the structure shown in FIG. 19D. Caution should be given to the fact that the SNP alleles in the product and the ASOs used for amplification do not always correspond to each other. The product is then ligated with a thermophilic bacterium-derived ligase enzyme such as Taq ligase at high temperature for improvement in nucleotide selectivity. Alternatively, the product may be ligated optically with a probe prepared with a photoreactive nucleotide, similarly at high temperature. The ligation reaction leads to ring closure by ligation of the probes at both terminals, giving a dumbbell-shaped molecule 222 similar to that shown in FIG. 19D, and, when there is no target SNP, the product remains as a linear, open-ring nucleotide 221 in the solution.

The reaction solution thus obtained is then subjected to digestion reaction of digesting part of the unreacted ASO primer 201 and LSO primer 202, and unreacted straight-chain molecule nucleotides 221 used in the first PCR, before the second PCR for amplification of tag sequences. The step prevents PCR mispriming and generation of unpredictable products caused by complicated sequence structure, by partially digesting the residual straight-chain molecule, i.e., the nucleotide 221. The digestive enzyme digests the nucleotide from the single-stranded chain terminal, and thus, the sequences and the tags of the SNP-detecting probes present at the terminal of the unreacted first PCR product, ASO 207 and LSO 210r are favorably decomposed first. However, the step is not needed in principle, and may be or may not be used.

In the present invention, the reaction product may be digested by using the exonuclease activity of a KOD polymerase available from Toyobo, but any other enzyme may be used instead, as long as it has an exonuclease activity to single-stranded nucleotides. Alternatively, a DNA ring-closed by ultrasonication may be converted into a straight chain, or long-chain DNAs may be fragmented by exposure to a low-salt concentration solution at high temperature, for prevention of PCR-inhibiting complicated secondary structures.

See FIG. 19E. In the second PCR amplification, the region between AT and LT in a closed-ring nucleotide 255 is amplified. By attaching a detection label to the tag by labeling AT or LT chemically, it is possible to perform amplification of the tag or simultaneous amplification of the tag and conversion into the single-strand chain. For example, when the amount of the AT and LT primers are the same, it is normal PCR amplification. During the PCR amplification, the system may be made asymmetric by using a primer with a detection label in an amount greater than that of the other primer. The asymmetric PCR gives a product 235 similar to that shown in FIG. 19F. FIG. 19F shows an example when a solid-phase probe 258 is used as a probe solid-phase region 257 of nucleotide microarray 256. After hybridization of the product 235 labeled with a labeling substance to the solid-phase probe 258, the labeling substance is measured. However, as will be described below, the method is not limited thereto.

When a single-stranded detection tag is amplified in the second PCR, it may be used for detection after completion of the reaction. If a double-stranded-chain detection tag is amplified, it should be denatured into a single-strand chain before it is subjected to detection reaction. The conversion may be performed in the following manner. For example, biotin is labeled to the 5' terminal of the primer producing a detection tag chain on the undetected side. Thus, after PCR amplification in the second PCR reaction, the biotinated double-stranded chain tag is separated from the solution, for example, with biotin-coated magnetic beads or a porous plate well. The labeled tag is converted into a single-strand chain and separated from the solution, by denaturing the separated double-stranded chain by heating in a low-salt concentration buffer at 95° C. or by exposure to an alkali such as aqueous NaOH solution. Alternatively, the solution may be heated to 95° C. and then quenched in ice immediately before detection.

Examples of the detection labels include fluorescent dyes suitable for nucleotide labeling such as Cy3, Cy5, FITC, Alexa and TAMPA, beads containing a fluorescent dye, beads containing a quantum dot or multiple quantum dots, DIG (digoxigenin) used in chemiluminescent detection, biotin, and the like. However, the labels are not limited thereto, and any label may be used, as long as it can be bound to a nucleotide such as DNA for detection of hybridized tag.

In the final detection reaction, each of the sequences in the single-stranded labeled tag obtained after the second PCR is determined quantitatively. For example, a nucleotide microarray 56 having minute probe spots fixed on a slide glass (see FIG. 5F), fluorescence-identifiable beads available from Luminex, or a bead array having beads adsorbed on both ends of filaments available from Illumina may be used for detection.

The capillary array disclosed in Jpn. Pat. Appln. KOKOAI Publication No. 11-75812 is also a detection device suitable for detection by using many kinds of tags present in solution as probes. The single-strand-chain label tag obtained in the denaturation process after the second PCR reaction is then hybridized on such a detection device, and nonspecific hybrids are removed by washing. Then, the label on the tag is detected, for example, by chemiluminescent reaction, image detection by a microarray scanner or a charge coupled device (CCD) camera when the label is a fluorescent dye, or fluorescent bead detection in a flow cytometer.

The amounts of corresponding label tags are determined from these detection data; the state of SNP allele whether it is homozygous or heterozygous is determined from the data by analysis with software; and the typing results are stored electronically as a file, recorded on a data-recording medium, or displayed or printed on paper as a graph.

In the sequences constituting the tags used as primers such as AT, LT, and MT, an orthonormal sequence disclosed in Jpn. Pat. Appln. KOKAI Publication No. 2002-318992 is preferably selected as the base unit. The orthonormal sequence is designed to have a melting temperature (Tm) in a particular range (i.e., normal), when it forms a double-stranded chain and not to form a stable hybrid when two sequences other than complementary chains hybridize or when it hybridizes to a sequence newly obtained by combination of two sequences (i.e., orthogonal). Preferably, an orthonormal sequence that does not form a stable hybrid with the genome or gene sequence to be detected is selected and used.

The length of the tags is determined according to the respective reactions, and the composition and the length of the nucleotides are preferably so determined that they has Tm's in a temperature range close to the annealing temperature of the PCR, asymmetric PCR, or hybridization reaction. The length is preferably approximately 15 to 35 bases, and such a tag is lower in purification cost when produced. The optimum reaction temperature is preferably 40° C. or higher and not higher than the optimum temperature of 72° C. for the thermophilic bacterium-derive polymerase commonly used in PCR.

(1-2). Aspect of Detecting Mutation in Combination of Complementary Chain Synthesis and Ligation Reaction (Gap Ligation)

Instead of using the ligation reaction described in (1-1) above, an example of using a ring-closure reaction in combination of complementary chain synthesis and ligation reaction, called a gap ligation, will be described.

Figure 20:
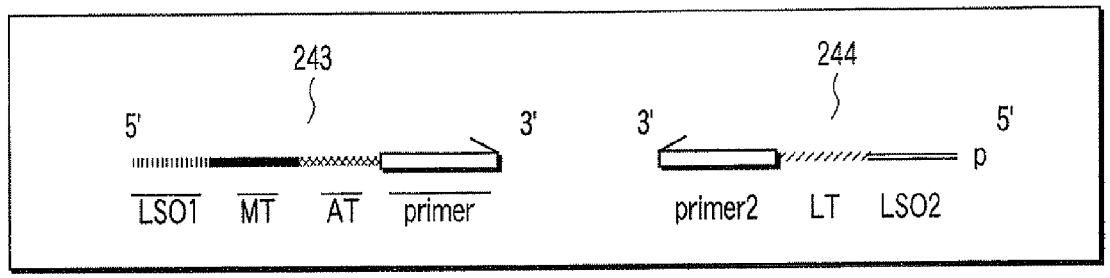
FIG. 20 is a chart showing an aspect of the present invention.

Two primers shown in FIG. 20, i.e., a first primer 243 and a second primer 244, are needed for the gap ligation. The structures thereof are different from those used for detection by ligation. The first primer 201 shown in FIG. 15A has an ASO sequence 207 having a base 203 corresponding to the SNP nucleotide at the 5' terminal, while in the first primer 243 shown in FIG. 20, a sequence called LSO 1 excluding the base 203 at the sequence terminal is placed as the first probe sequence. On the other hand in second primer 244, the sequence called LSO will be called LSO 2 and is placed as the second probe sequence. Both of the first primer 243 and the second primer 244 and other sequences, i.e., artificially designed sequences MT, AT and LT, and the first and second priming sequences, for use are the same as those described in (1-1) above.

The reaction requires a step of removing dNTP remaining after the first PCR. Any known means for removal of dNTP may be used in the step after the first PCR amplification or smoothing reaction. For example, the PCR product may be recovered with a filter, or alternatively, a labeling substance of the first primer LSO 1 (primer 243) or the second primer LSO 2 (primer 244) may be removed, for example, by adsorption on magnetic beads. The labeling substance of the primer used then is not particularly limited as long as it is a substance, such as biotin, that allows selective binding and can be bound to the primer easily by known means.

Figure 21:
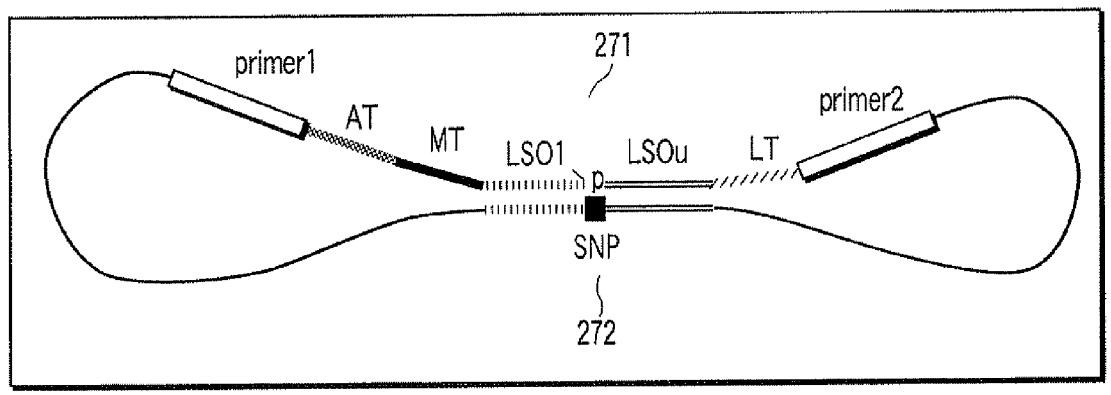
FIG. 21 is a chart showing an aspect of the present invention.

Then, for gap ligation reaction, reaction tubes respectively containing only one of dATP, dCTP, dGTP and dTTP are made available. As described above, the sample solution after the first PCR amplification and the smoothing reaction is added to each reaction tube containing only dATP, dCTP, dGTP or dTTP. A polymerase and a ligase are then added additionally to the respective reaction tubes. A nucleotide 271 having a dumbbell-shaped structure that lacks a base in forming a closed ring is then formed by temperature change, as shown in FIG. 21. The temperature change at this time is, for example, a temperature change generating a cyclic hybrid, and is preferably temperature drop, for example, from 95° C. to 65° C., although it may depend on the salt concentration of the reaction solution.

Figure 22:
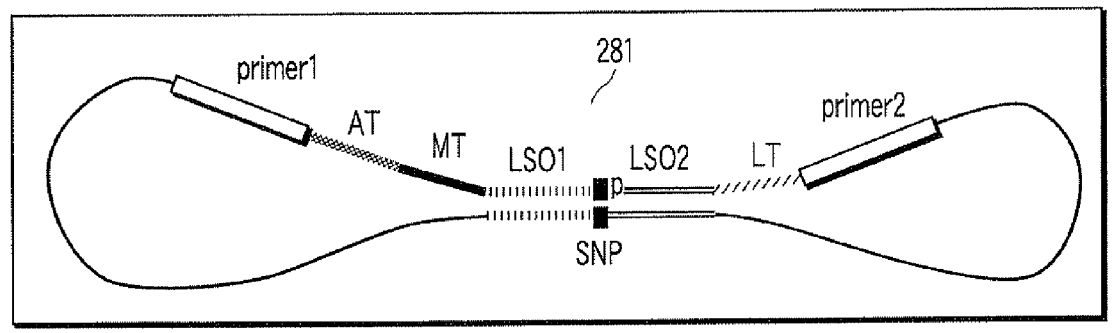
FIG. 22 is a chart showing an aspect of the present invention.

Subsequently, if there is a base complementary to the desirable SNP sequence 272 in the reaction solution, the complementary chain is elongated by one base by the polymerase, giving a nucleotide 281 having the structure shown in FIG. 22.

Then, the elongated base and the 5' terminal of the phosphate-modified LSO 2 are ligated. The following reactions are performed respectively in the four tubes that are divided before gap ligation. However, if the kinds of the labels used in the second PCR amplification are altered for A, C, G and T, the reaction solutions in the four tubes may be detected after they are combined again into a single solution.

Figure 23:
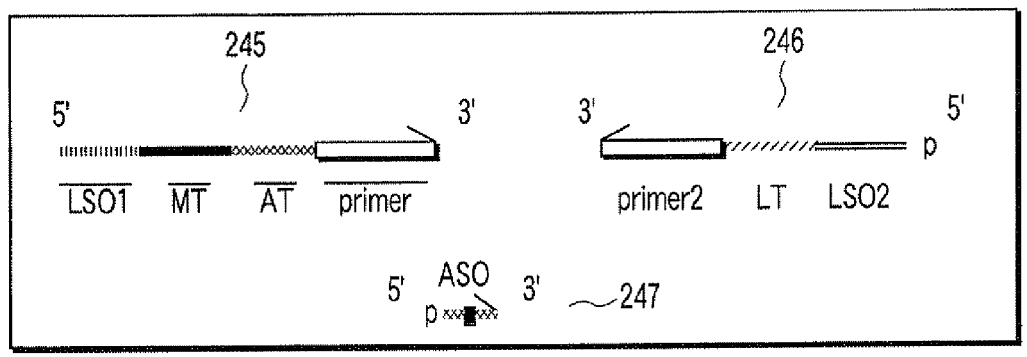
FIG. 23 is a chart showing an aspect of the present invention.

(1-3). Aspect of Detection by Using Ligation Reaction of Connecting Two or More Gaps As shown in FIG. 23, the probe may be divided into three pieces for detection. In detection by the gap ligation method described in (1-2) above, the SNP nucleotide is eliminated from the 5' terminal of the first primer. In the embodiment shown, three bases, including a desirable SNP nucleotide and the bases close thereto, are present as independent probes, which together represent a gap sequence 247 (indicated by "ASO" in the figure).

Because there are many sequences of SNPs, a nucleotide having a SNP selected from four kinds: A, C, G, and T, and mixed base as the bases at both sides of the SNP is prepared and the 5' terminal thereof is phosphate-modified. A universal base such as inosine may be used, instead of the mixed base. In contrast to the gap ligation method described in (1-2) above, the probe sequence of the first primer 245, LSO 1 sequence, and the probe sequence of the second primer 246, LSO 2 sequence, both have sequences respectively missing a SNP-sided base. In addition, the 5' terminal of the LSO 2 sequence in the second primer 246 is modified by phosphorylation (FIG. 23).

Figure 24:
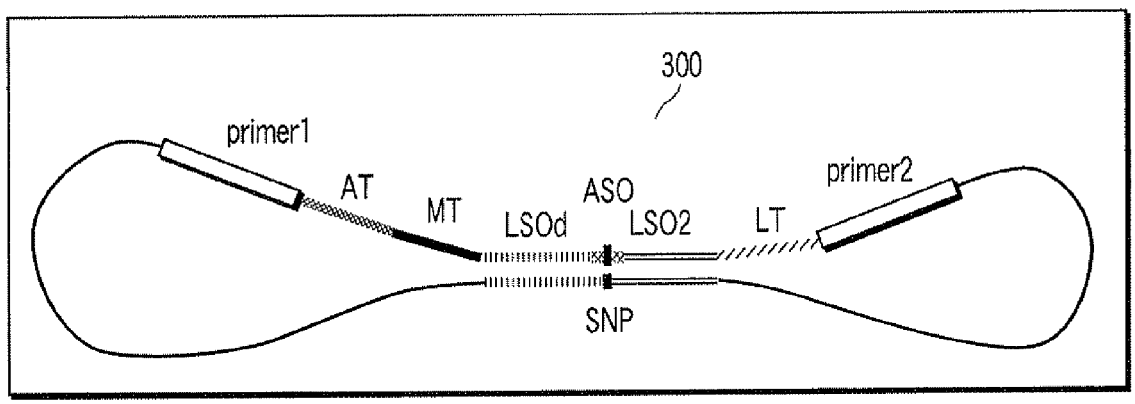
FIG. 24 is a chart showing an aspect of the present invention.

First, the first PCR amplification is performed by using the first primer (LSO 1 primer 245) and the second primer (LSO 2 primer 246). The reaction is carried out, similarly to the ring closure by a common ligation method. Before the ring-closure reaction by ligation, ASO sequences 247, of which the desirable SNP-equivalent unit is a gap sequence of A, C, G or T, are placed respectively in four reaction tubes previously. The reaction solution before ring-closure reaction by ligation is added to the respective four reaction tubes, as it is divided. Because the gap sequence ASO 247 is short, the ligation reaction in each of these tubes may be carried out at a relatively low temperature, for example, of 37° C. Any known ligase highly active at the temperature may be used as the ligase. In addition, the reaction mixture is then processed, similarly to the gap ligation described above until the detection reaction. FIG. 24 shows a nucleotide molecule 300 in the ring-closed state after detection of the desirable SNP.

(1-4). Embodiment of Using ASO and LSO Primers with Simplified Tag Structure

Figure 25:
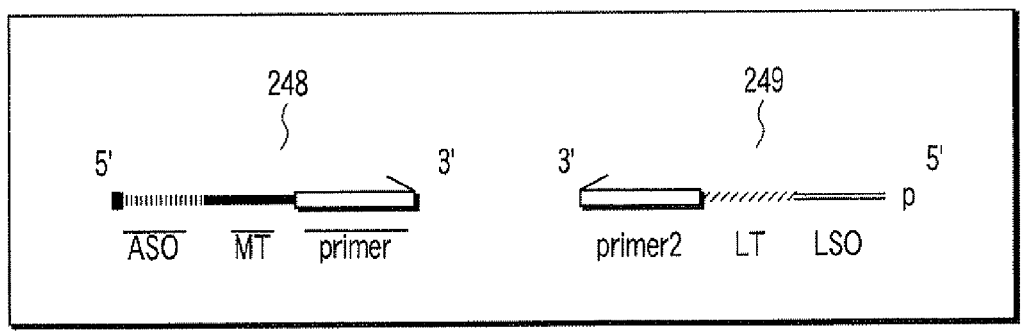
FIG. 25 is a chart showing an aspect of the present invention.

FIG. 25 shows an example of using artificially designed sequences: the first primer not containing AT (ASO primer 248) and the second primer (LSO primer 249).

In addition, an embodiment of the present invention will be described with reference to FIG. 26. In the method in the present embodiment, for example, among the tag sequences (i.e., sequences other than priming sequence, such as "ASO", "MT" and "AT" sequences) on the allele-specific ASO side (i.e., the first primer 1), an artificially designed sequence lacking the AT sequence, i.e., the first primer 248 is used as in the first primer 201 shown in FIG. 15 (FIG. 26A). The analyte nucleotide is subjected to the first PCR amplification (FIG. 26A), by using the first primer 248 and the second primer 249 shown in FIG. 26A.

Two kinds of MT sequences for use as the primer in second PCR amplification are made available according to the two kinds of alleles of the desirable SNP. During the second PCR amplification, the two kinds of MT sequences are used respectively as primers, but they are labeled with fluorescence labels different from each other and used as a first MT primer 301 and a second MT primer 302 (FIG. 26B). A probe sequence, an artificially designed sequence LT close to LSO, is so determined that it has a sequence varying according to each desirable SNP. Thus in the second PCR amplification, two kinds of MT sequences are needed as primers, and the LT sequences are prepared in the number of the SNPs to be detected.

Then, they are subjected to second PCR amplification reaction (FIG. 26B). As shown in FIG. 26C, when the sequence of the probe 306 is so determined to detect the chain complementary to the LT sequence during detection of the second PCR products 303 and 304 thus prepared, for example, on microarray 305, it is possible to compare the allele amount rate from the difference in fluorescence intensity of the same spot 307 on the microarray 305. By the method in the present embodiment, it is also possible to shorten the length of the first primer ASO.

(1-5). Aspect of Using a Tag Labeling Substance Instead of a Tag Sequence Nucleotide It is possible to provide a favorable aspect of the method according to the present invention by using a first primer of ASO primer 250 and a second primer of LSO primer 251 having an identifiable chemical, for example biotin or hapten, as a label at the position not at the terminal of the nucleotide as shown in FIG. 27. The first primer 250 and second primer 251 described above may be prepared by any known traditional method.

For example, a linker molecule or a continuous spacer sequence of base A (such as, adenine) may be inserted between the first probe sequence ASO and the first priming sequence (indicated by "primer 1" in FIG. 27) and between the second probe sequence LSO and the second priming sequence (indicated by "primer 2" in FIG. 27).

The first PCR amplification is performed by using such an ASO primer 250 and an LSO primer 251, and a closed-ring molecule is formed, for example, by ligation. The ring-closure reaction then is aimed at detecting alleles and protecting nucleotides. Straight chain molecules are digested and straight chain nucleotides having chemical labels at both terminals disappear in digestion reaction after the ring-closure reaction.

When the closed-ring molecule is mixed with streptavidin-coated latex beads and anti-hapten-antibody-coated latex beads, the latex beads respectively bind to the closed-ring molecule and the beads aggregate if there is a target allele. On the other hand, straight chain molecules are decomposed by exonuclease treatment and thus do not cause aggregation of the beads. In this way, it is possible to detect presence of a particular allele.

In addition, the reaction may be performed while the chemical labeling substance bound to the ASO primer is changed for detection of multiple alleles even at the same SNP site; and specifically, the reaction may be performed while biotin is labeled to the ASO primer for detection of an allele and DIG (digoxigenin) is labeled to the ASO primer for detection of another allele. As a result, there may be two kinds of closed-ring molecules obtained, but SNP can be detected by examining bead aggregation while using respectively different bead suspensions: suspensions of anti-DIG-antibody-coated beads and anti-hapten-antibody-coated beads, or suspensions of streptavidin-coated beads and anti-hapten-antibody-coated beads.

Another bead-detecting method when such a labeling is performed is a detection method by using magnetic beads. After the closed-ring molecule is first generated, the reaction solution is allowed to react with anti-hapten-antibody-coated magnetic beads. A hapten-labeled nucleotide is captured then by the magnetic beads, and the beads are recovered form the solution by B/F separation. It is possible to detect presence of an allele by measuring the fluorescence from the beads by mixing the beads with an anti-hapten antibody labeled with streptavidin and a fluorescent dye and thus allowing specific binding of the antibody while the B/F separation is continued. For detection of the nucleotide on the magnetic beads after B/F separation, chemiluminescence or light absorption may be used, instead of fluorescence.

Alternatively, the ASO and LSO primers may not be labeled, and different identifiable chemical labels may be bound to the MT and LT primers in the second PCR, and specifically, biotin may be labeled to the MT primer and hapten to the LT primer. In such a case, the second PCR amplification is performed not by asymmetric PCR but by normal PCR for obtaining a double-stranded-chain tag amplification product. The product is then allowed to aggregate with the streptavidin-coated latex bead and the anti-hapten-antibody-coated latex beads as described above, and the desired SNP is detected by detection of the aggregation.

(1-6), Aspect of Detection by Single-Colored Fluorescence

It is possible to detect SNP alleles without using multiple kinds of fluorescent dyes. For example, MT sequences different from each other are designed according to the ASO sequence by the method described in (1-1) above and the SNPs are detected on a microarray. Probes detecting the MT sequences are previously fixed on the microarray. It is thus possible to detect fluorescence in spots different in each allele, only by binding a single-colored fluorescent dye to the MT primer for use in the second PCR amplification. As a result, it is possible to detect which allele is present.

(1-7). Aspect Concerning Detection

Examples of detection means for use in the present aspect of the invention will be described below, but the present invention is not limited thereby. As described above, in an aspect of the present invention, it is possible to perform first amplification of a sample nucleotide with primers and introduce a probe sequence for intramolecular detection to the amplification product terminal simultaneously. As a result, the probe region hybridizes when there is mutation, and the amplification product obtained acquires a particular internal structure, which is then ring-closed by an enzyme. It is thus possible to detect nucleotide mutation by analyzing the amplification product containing a closed-ring region obtained by the second amplification, for example by PCR.

For example, for simultaneous detection of multiple mutations in a sample nucleotide, it is possible to examine presence of one or more kinds of mutations by using artificially designed sequences and tags and detecting the tags by hybridization.

Means for use in detection of mutation in the aspect of the present invention will be described below. The detecting means include methods of detecting presence of a single mutation and methods of detecting presence of multiple mutations. Examples of the methods of detecting presence of a single mutation include gel electrophoresis, method of using bead aggregation, and the like. Examples of the methods of detecting presence of multiple mutations include a method of using microarray, bead aggregation, and identifiable beads, and the like.

When gel electrophoresis is used, the next method may be used. A ring-closed nucleotide molecule formed according to the method of the present invention and straight-chain nucleotide molecules are different from each other in electrophoretic mobility. Generally, a closed-ring molecule has a greater electrophoretic mobility, and thus, has a smaller apparent molecular weight. For example, when gel electrophoresis is used for detection of a mutation, a closed-ring molecule, when present, gives a band having a larger electrophoretic mobility. When molecular weight markers for reference, actual ring-closed nucleotide molecules and straight-chain nucleotide molecules, and others are analyzed simultaneously by electrophoresis, for easier comparison of electrophoretic mobility, it is possible to detect presence of mutation more accurately.

An example of the detection method by using a microarray will be described below. The microarray is prepared by immobilizing many nucleotide probes complementary to artificially designed sequences on a substrate such as slide glass or dish (including multi-well dish) as fine spots. It is possible to detect presence of mutation, by detecting presence of hybridization on the immobilized nucleotide probe. For example, an identifiable chemical may be labeled on the primer according to the present invention used in the second amplification. As a result, the second amplification product contains artificially designed sequences. Thus, these sequences are allowed to hybridize to the complementary probes on the microarray, and the chemical substance labeled on the second amplification products is detected via the primer. It is possible, by using such a microarray, to detect easily multiple kinds of artificially designed sequences that are present, i.e., mutations thereon. In the example above, fluorescent detection by labeling with a fluorescent dye is favorable in convenience. However, the detection method is not limited thereto, and other identifiable means such as chemiluminescence, color development or the like may be used. The operator may select better means according to the needed sensitivity and density of the probes.

Alternatively, a fluorescent bead system available from Luminex Corp., means similar to microarray, may be used according to the present invention. The fluorescent beads contain two kinds of fluorescent dyes respectively at 10 different concentrations. Thus, it is possible to identify 100 kinds of beads by fluorescent detection. For example, a probe of artificially designed sequence according to the present invention is immobilized on each of the fluorescent beads different in kind. It is possible then to detect presence of mutation by labeling the amplification product according to the present invention obtained in the second amplification phase for example with a fluorescent dye, allowing it to hybridize to a fluorescent-bead probe, detecting the fluorescent bead one by one optically by a mechanism similar to that of a flow cytometer, and examining hybridization of the artificially designed sequence on the respective fluorescent beads.

Alternatively, semiconductor particles, such as quantum dot, identifiable by using fluorescence may be detected according to the aspect of the present invention. The quantum dot is a semiconductor fine particle. It is a fluorescent material showing various characteristics not found in other organic dyes, and any material known by those who are skilled in the art may be used, and such a material prepared by any known method may be used in the present embodiment of the invention. For example, when quantum dot is used, a probe is first immobilized on the quantum dot; the particles are spread on a flat plate separately and individually; and the kinds of the particle and the artificially designed sequence that hybridize on the particle are to be detected. However, the detecting means according to the present invention is not limited thereto, and any known traditional detection method may be used.

(2). Embodiment of Detecting Mutation by Insertion or Deletion

An example of detecting whether the mutation on an analyte nucleotide is caused by insertion or deletion will be described below. For example, for detection of insertion or deletion mutation of genome, a method of ligating at two or more sites by using a first primer, a second primer and a gap sequence is favorably used as described in (1-3) above. The gap sequence ASO is so designed that it becomes a sequence for detection of insertion sequence itself. For example, when the insertion sequence is TTTTAAAA and the sequence during insertion mutation is TTTATGCAAAA in the same direction, the gap sequence ASO is preferably an insertion-site sequence of CGTATTT from the 5' terminal.

In the case of deletion mutation, the sequences of the first primer LSO 1 and the second primer LSO 2 are so determined that they are bound directly to each other.

Similarly to (1-3) above, first PCR amplification is performed by using the first primer LSO 1 and the second primer LSO 2. Immediately before ligation, the reaction solution after the first PCR amplification is added to a reaction tube for detection of insertion mutation and a reaction tube for detection of deletion mutation, respectively as divided. The reaction tube for detection of insertion mutation then contains a gap sequence ASO, while the reaction tube for detection of deletion mutation contains no gap sequence ASO. Respective tubes are then subjected to ring-closure reaction in common ligation reaction. In addition, respective tubes are subjected to detection reaction similarly to the gap ligation described above, for determination of whether the mutation is an insertion or deletion mutation.

The reaction solution may be mixed during detection, and, in such a case, the PCR product produced by second PCR amplification is simply analyzed by electrophoresis. A long fragment, if detected, possibly indicates insertion mutation, while a short fragment, if detected, indicates deletion mutation.

(3). Aspect of Detecting Genome Methylation

In an aspect of the present invention, it is possible to detect methylation of genomic DNA. In this case, bisulfite treatment of converting cytosine specifically into uracil should be performed first. The treatment converts unmethylated cytosine into uracil and leaves methylated cytosine as it is, i.e., as cytosine. The first and second primers used in (1-1) above are designed to detect the converted uracil or the cytosine remaining unconverted, and they are allowed to react in a manner similar to that in (1-1) above for detection.

Alternatively, it is possible to detect presence of unmethylated cytosine by performing elongation and ligation by using the first and second primers used in (1-2) above and a reaction tube containing dTTP and analyzing the product.

Alternatively, it may be detected by using the first, second and third primers used in (1-3) above. In such a case, the methylation may be detected by preparing an ASO complementary to a particular CpG island, i.e., a gap sequence, allowing detection and reaction thereof, and analyzing presence of a closed-ring molecule. Alternatively, it is possible to detect desirable methylation by using the method in any embodiment described above.

(4). Embodiment of Detecting the Repetition Number of Repeating Sequences

The Sanger's method has been used for detection of the repetition number of repeating sequences, but it is also possible to detect the repetition number of repeating sequences according to the method of the present invention. The sequences of the first probe sequence LSO 1 and the second probe sequence LSO 2 are designed to have the repeating sequences inside by application of the gap ligation method described in (1-2) above; the first and second primers are also designed; and the first PCR amplification is performed. Then, a reaction tube containing the monomer for the base constituting the repeating sequences is made available. The first PCR amplification product is added thereto, and subsequent complementary chain synthesis and ligation reaction give a closed-ring molecule. It is subjected to second PCR amplification by using MT and LT primers. It is possible to determine the repetition number of the repeating sequences by analyzing the second PCR product obtained properly by electrophoresis and thus determining the length.

(5). Aspect of Measuring Expressed Gene

According to the aspect of the present invention, it is possible to determine the amounts of genes expressed in a cell. Hereinafter, embodiments of such detection will be described.

First, mRNA is extracted from cells, and cDNAs are prepared with a reverse transcriptase. The positions of ASO and LSO as probe sequences are so determined to detect exons having a smaller number of detection gene mutations.

SNP may not be considered in measurement of gene expression, but the sequences of ASO and LSO and also those of primers 1 and 2 are preferably selected to be highly specific to the target gene. The gene expression is detected similarly to detection of other mutation, by a method similar to that described in (1-1) above.

In such a case, it is possible to determine the ratio of expression amounts, by using a single-colored fluorescence label per one sample, changing the fluorescence label for each sample, and detecting the florescence different in color simultaneously on the same microarray.

(6). Advantageous Effects

According to the method in an aspect of the present invention described above, it is possible to carry out a detection reaction by intramolecular reaction of the PCR amplification product of analyte nucleotide. Accordingly, addition of no detection probe is need after PCR amplification. It is thus possible to make both terminals of the PCR product function as probes. The conventional detection reaction requires a total of four components, two oligo probes, an analyte nucleotide and an enzyme, but according to the present invention, it is possible to reduce the number of the components needed for detection only to two: an analyte-nucleotide amplification fragment and an enzyme. In addition, the reaction efficiency was improved drastically, and it became possible to detect mutation from a trace amount of nucleotide. Accordingly, such a method would be effective in shortening the reaction step and reducing the cost.

It is also possible to detect the DNA sequence of a final analyte gene as an artificially designed sequence according to the present invention above. Thus, it is possible to use the same detection device, for example, a device called universal chip, for detection. Thus, there is no need for change in the order or formats of the detection devices, regardless of the type of gene mutation to be detected. It is also possible to analyze multiple items simultaneously, because it can use an artificially designed sequence.

In an aspect of the present invention, the product is subjected to a smoothing reaction by a double-stranded-chain-terminal-smoothing enzyme, after the first PCR, i.e., first PCR amplification, before ring-closure reaction. dATP added by Taq polymerase is eliminated by action of an enzyme smoothing double-stranded chain terminal, and thus, the terminal of the first PCR amplification product is smoothed. It is thus possible to prevent deterioration in the efficiency of ring-closure reaction by ligation reaction or by combination of one-base elongation reaction and ligation reaction and to improve the detection sensitivity and specificity.

According to the aspect of the present invention, a cleanup reaction is performed with a nucleotide-digesting enzyme after ring-closure reaction and before second PCR amplification reaction. Thus, undesirable single-stranded nucleotides, such as abnormal nucleotides produced in the intermolecular reaction other than the desired product ring-closed nucleotides and residual primers, are digested. As a result, the amplification reaction does not produce undesirable products, leading to decrease of false positive signals.

Further, according to one aspect of the present invention, it is possible to detect mutation easily by aggregation between anti-hapten-antibody-coated latex beads and streptavidin-coated latex beads, when a probe with its tag sequence replaced with an identifiable chemical such as hapten or biotin is used. If there is target sequence, the latex beads aggregate, and thus, the change can be easily detected visually or by a simple absorption analysis.

Applications and places for use of the detection method according to the present invention include the followings: research applications such as studies on the relationship between gene type and disease, detection of medicine sensitivity, and molecular biological analysis of gene polymorphism in human and other animals. The studies will be conducted in research institutes and laboratories such as university and company. When the relationship between a gene and a particular disease, morbidity risk, or medicine sensitivity is more available, applications thereof will also include medical applications such as tests for determining treatment methods in test laboratories of hospitals, preventive diagnosis during medical check up, medicine sensitivity tests for selection of an anti-cancer drug with smaller adverse reaction, and the like. The detection method according to the present invention may also be used in DNA computing.

The method according to the present invention may be used, for example, during use of a gene polymorphism-detecting reagent kit for the user's research or diagnosis purpose, automatic analysis in an automatic reaction apparatus, licensed research for the user or patient, and tests in test laboratories.

The reactions may be combined arbitrarily in applying the present method. For example, it is possible to initiate detection reaction directly from genomic DNA, by establishing a cell line and culturing the cell in a great amount, collecting a greater amount of peripheral blood, or preparing the human genomic DNA needed for the present method in a great amount. Alternatively, the detection reaction may be initiated in a sample prepared by collecting a small amount of genomic DNA and amplifying the genomic DNA non-specifically by the WGA method (Whole Genome Amplification) of using a chain-substitution polymerase and a random primer. Yet alternatively, the detection reaction may be started in a solution in which a particular sequence is amplified with a primer, for example by a PCR method, multiplex PCR method, or asymmetric PCR method. A sample prepared by an enzymatic amplification method may be detected, when it is a double-stranded chain sample, after conversion into a single-strand chain, for example, by heating to 95° C. and subsequent quenching at 4° C., fragmentation by heating to 95° C. in a low-salt concentration solution, fragmentation by ultrasonic irradiation, cleavage with a restriction enzyme, to a degree that does not impair detection.

Thus in the aspect of the present invention, provided is sequence-detecting means that is resistant to nonspecific reaction and allows operation at lower cost.

III. Method of Using Complementary Chain Synthesis-Inhibiting Structure

An embodiment of the nucleotide sequence-detecting method according to the present invention will be described with reference to FIG. 28. In the embodiment, the detection method according to the present invention concerning a nucleotide chain 401 containing a detecting site 412 for detection of single-nucleotide polymorphism (hereinafter, referred to as "SNP") will be described.

The nucleotide chain 401 may be any one of DNAs and RNAs including cDNA, genomic DNA, synthetic DNA, mRNA, entire RNA, hnRNA, and synthetic RNA.

The nucleotide chain 401 may be a nucleotide derived from any origin. The nucleotide chain 401 used in the method according to the present invention may be prepared by any known method. The "nucleotide chain" is also called a "nucleotide sample", and the terms "nucleotide chain" and "nucleotide sample" are used interchangeably in the present description.

1. Synthesis by Single-Stranded Gap Ligation

A first detecting chain-preparing nucleotide 402 contains a sequence 413 homologous to the 3'-sided partial sequence of the detecting site 412, a first tag 404, and a primer sequence 403. The primer sequence 403 may be the 3'-sided sequence of the detecting site 412 of the nucleotide chain 401, i.e., a sequence complementary to the 3'-sided sequence of the detecting site 412.

A second detecting chain-preparing nucleotide 405 contains a sequence 414 homologous to the 5'-sided partial sequence of the detecting site 412, a second tag 408, a complementary chain synthesis-inhibiting structure 407 close to the 5' side of tag 408, and additionally, an oligonucleotide sequence 406 complementary to the 5' side of the detecting site 412, on the 5' side thereof.

The reaction starts with hybridization of the nucleotide chain 401 with the first detecting chain-preparing nucleotide 402 and the second detecting chain-preparing nucleotide 405 (FIG. 28(1)).

Then, the first detecting chain-preparing nucleotide 402 is elongated in the direction from 5' to 3' side under a condition allowing elongation (FIG. 28(2)). The phrase "under a condition allowing elongation" is not particularly limited, as long as it is an environment suitable for the first detecting chain-preparing nucleotide to extend. Thus, it is a condition containing an enzyme and a substrate needed for elongation. Any environment and/or condition known to those who are skilled in the art may be used.

Then, the 3' terminal of the elongated first detecting chain-preparing nucleotide 402 and the 5' terminal of the second detecting chain-preparing nucleotide 405 are ligated (FIG. 28(3)). In the embodiment, the 5' terminal of the second detecting chain-preparing nucleotide 405 is phosphorylated, and thus, it is connected by the ligase. However, the method according to the present invention is not limited to the combination of phosphorylation and ligation, and at least one of the 3'-nucleotide of the first detecting chain-preparing nucleotide 402 and the 5'-terminal nucleotide of the second detecting chain-preparing nucleotide 405 is preferably so modified to bind to each other. Thus, for example, the group may be modified with known means such as the photoreactive pyrimidine base described in Japanese Patent No. 3753942, in addition to phosphorylation, but the modification is not limited thereto.

The nucleotide is then denatured, to give a single-strand chain (FIG. 28(4)). Any known denaturation means may be used for denaturation. Examples of the denaturation means include, but are not limited to, heating, alkali denaturation, exposure to low-salt concentration by dilution, and the like.

The detecting chain 410 is so designed to cause intramolecular hybridization. Thus, the single-strand chain obtained by denaturation has a dumbbell shape 421 after the ring-closure reaction (FIG. 28(5)). The chain further changes into a cyclic structure 422, for stabilization of the molecule (FIG. 28(5)).

In addition, single-stranded nucleotides may be digested after ring-closure reaction. The digestion is favorable, because it leads to high detection sensitivity and/or operability during subsequent detection and/or operation (FIG. 28(6)). Nucleotides not elongated favorably during elongation reaction in FIG. 28(2) are decomposed in the digestion reaction.

The cyclic structure obtained may be analyzed by electrophoresis or by mass spectrometry. The complementary chain synthesis-inhibiting structure 407 contained in the second detecting chain-preparing nucleotide 402 may not be contained in such detection.

A method of detecting SNP has been described in the embodiment above, but the analyte may be mutation other than SNP, detection of deletion, insertion, substitution, or repeating sequence, detection of methylation, measurement of gene expression, or the like, and any sequence other than mutation may be detected. The detecting site may contain a sequence to be detected or may be only the sequence to be detected.

In the aspect, it is possible to detect gene mutation economically without use of a great number of probes.

The complementary chain synthesis-inhibiting structure is more effective during the following analyses. The phrase "complementary chain synthesis-inhibiting structure" is not particularly limited, as long as it is, for example, a structure which a polymerase does not recognize as a DNA base and form a complementary chain with, and examples thereof include nucleotides modified with Spacer 9 linker available from Greiner Bio-one, synthetic nucleotides absent in nature, nucleotides containing no baser and the like.

2. Detecting Means

In another aspect of the present invention, the detection method according to the present invention may be performed by obtaining nucleotide fragments containing a connecting region from the formed cyclic structure and detecting the nucleotide.

For that purpose, nucleotide fragments containing a connecting region are obtained from the cyclic structure. The "nucleotide fragments" obtained by the following means are also called "amplification products".

(1) Asymmetric PCR

For obtaining the nucleotide fragments, for example, an asymmetric PCR may be used, although the method is not limited thereto.

See FIG. 29. Shown in FIG. 29(7)-A is a method of subjecting the cyclic structure 422 to asymmetric PCR, together with a first primer 425 and a second primer 423 carrying an identifiable label. The first primer 425 has a sequence complementary to the 3'-sided sequence of the detecting site 412 of cyclic structure 422. The second primer 423 has an identifiable label bound to the 3' terminal and has a sequence complementary to the 5'-sided sequence of the detecting site 412 of the cyclic structure 422.

These third primer 425 and second primer 423 and the cyclic structure 422 are subjected to asymmetric PCR under a suitable condition. As a result, an amplification product 427 having an identifiable label is obtained. Favorably, the concentration of the labeled-sided primer is, for example, 10 with respect to 1 of the concentration of the unlabeled-sided primer, although the ratio is not limited thereto, as described in literatures such as Kinjo M. et al., "Detection of asymmetric PCR products in homogeneous solution by fluorescence correlation spectroscopy," Biotechniques, 1998 October; 25 (4): 706-12, 714-5, or website (Molecular Biology Techniques Manual, http://www.mcb.uct.ac.za/pcrcond.htm).

(2) In-Vitro Transcription Reaction

For example, in-vitro transcription by using a T7 promoter may be used for obtaining the nucleotide fragments.

As shown in FIG. 29(7)-B(i), the first detecting chain-preparing nucleotide in the cyclic structure is preferably designed to have a T7 promoter inserted into its tag region. It is possible to obtain desirable nucleotide fragments, by producing double-stranded DNAs under a condition allowing suitable in-vitro transcription of such a cyclic structure 422 and denaturing them into single-strand chains repeatedly. The condition allowing suitable in-vitro transcription may be any condition known to those who are skilled in the art.

As shown in FIG. 29(7)-B(ii), the first detecting chain-preparing nucleotide in the cyclic structure is preferably designed to have a T7 promoter inserted in the region close to the 5' side of the tag region, similarly to FIG. 29(7)-B(i) described above. Such a cyclic structure 422 is subjected to RNA in-vitro transcription by a RNA polymerase under a suitable condition allowing suitable in-vitro transcription. In this way, it is possible to obtain the amplification product continuously, because there is no need for denaturation operation. It is also possible to type correctly when hetero alleles by mutation such as SNP are detected, because the cyclic structure is amplified almost linearly. Examples of the suitable conditions include, but are not limited to, those described in literature (Philips J., Eberwine J. H., "Antisense RNA Amplification: A Linear Amplification Method for Analyzing the mRNA Population from Single Living Cells," Methods. 1996 December; 10 (3): 283-8).

As described above, as there is a complementary chain synthesis-inhibiting structure between the tag and the primer sequence, production of the complementary chain is terminated at the inhibition position, and thus, favorably, there is no undesirable long chain product produced, when the presence of the cyclic structure is reflected to other nucleotides.

As there is a complementary chain synthesis-inhibiting structure between the tag and the primer sequence, production of the complementary chain is also terminated at the inhibition position. Because production of the complementary chain is terminated halfway as described above, it is possible to obtain a product having the minimum length needed by tag amplification by in-vitro transcription by using a T7 promoter.

(3) Detection

The amplification product obtained by the methods described above can be detected in the following manner. For example, as shown in FIG. 30(8)-A, it is possible to detect presence of a desirable detecting site by allowing an amplification product carrying an identifiable label to hybridize to a probe 448 immobilized on a substrate 450 of microarray 449 and detecting the label. It can also be detected on a similar microarray 449, by preparing an amplification product carrying second different identifiable label according to the sequence. Any methods known to those who are skilled in the art may be used as the methods of producing and using the microarray.

Any known labeling substance known to those who are skilled in the art may be used as the identifiable label, and examples thereof include, but are not limited to, fluorescent materials, biotin, digoxigenin, fluorescent proteins, HRPs for chemiluminescence, and the like.

Alternatively, fluorescent beads may be used for detection. Examples of the methods include those described in literatures (Dunbar S. A., "Applications of Luminex xMAP technology for rapid, high-throughput multiplexed detection nucleic acid detection", Clin. Chim. Acta. 2006 January; 363 (1-2): 71-82. Epub 2005 Aug. 15).

For example, the method described in FIG. 30(8)-B may be used, when an in-vitro transcription product is detected. For example, the in-vitro transcription product 457 is allowed to hybridize to a first probe 458 immobilized on the substrate 456 of microarray 459. In addition, a second probe carrying the identifiable label described above is allowed to hybridize to the single-stranded regions for example to the tag region, of the in-vitro transcription product 457. It is then possible to detect presence of the detecting site by detecting the identifiable label.

3. Adapter Ligation

In an aspect of the present invention, it is also possible to detect nucleotide sequences by using a principle and detecting means similar to those for the single-stranded gap ligation described above except that adapter ligation with a restriction enzyme and adapters is used.

See FIG. 31. The adapters for use in adapter ligation are a first adapter 470 and a second adapter 471. The first adapter is so modified to bind to the cleavage region of the first restriction enzyme. The 5' terminal of one of the double-strand is phosphorylated. The second adapter is so modified to bind to the cleavage region of the second restriction enzyme, and may contain a complementary chain synthesis-inhibiting structure. The second adapter is an adapter on the side containing the 5' terminal of the detecting chain. The 5' terminal of the double-stranded chain region is so modified that it can be bound. In the present embodiment, it is phosphorylated. The 5' terminal of the single-strand chain region is also so modified that it can be bound. Similarly in the present embodiment, it is phosphorylated.

The terminal is phosphorylated for easier binding as described above. Such modification is not limited to phosphorylation, and may be, for example, the modification with a photosensitive pyrimidine base described in Japanese Patent No. 3753942.

Figure 32:
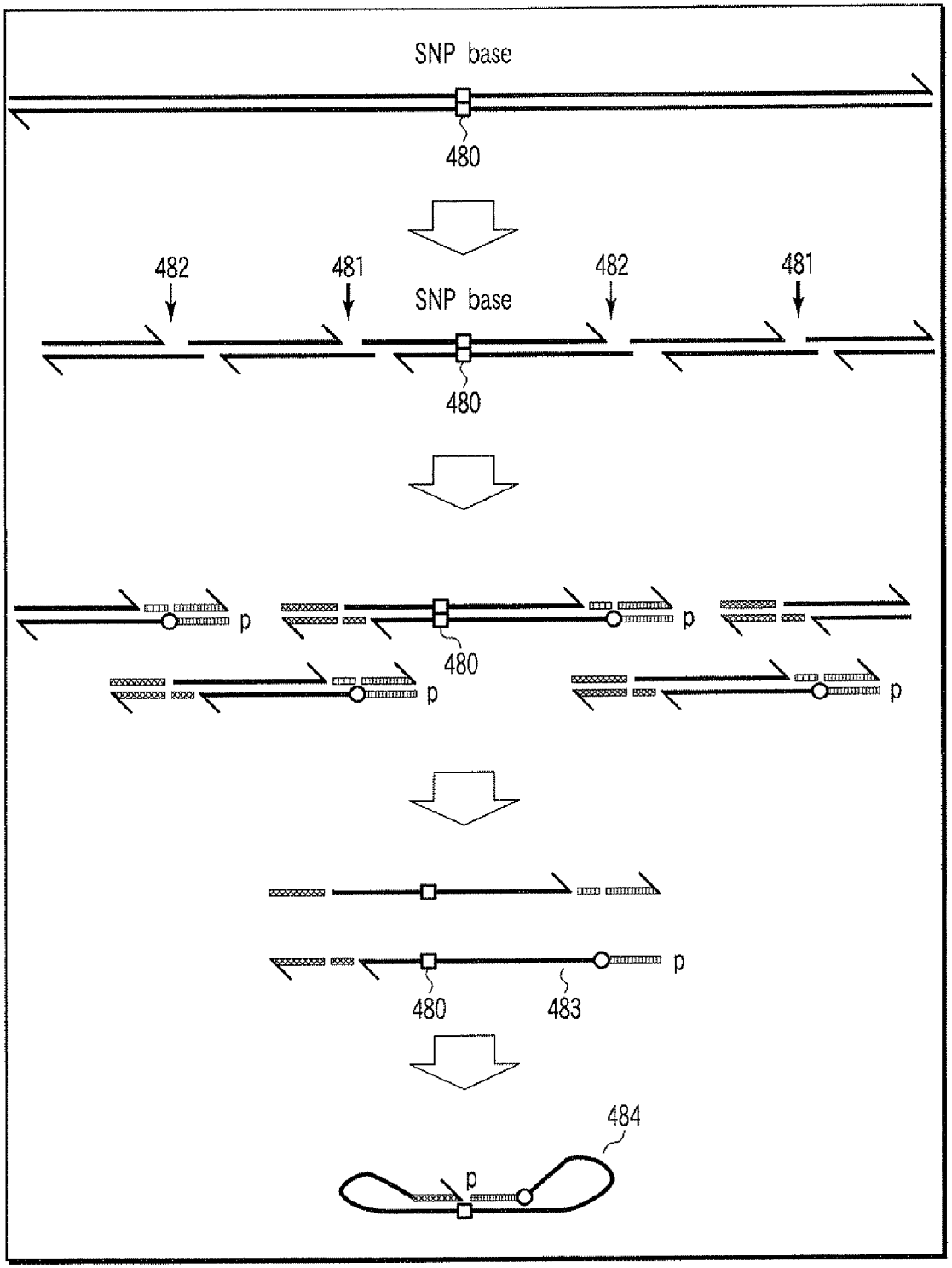
FIG. 32 is a schematic view showing an aspect of the present invention.

Hereinafter, the reaction for obtaining a cyclic structure by using these two adapters will be described. See FIG. 32. In the case of adapter ligation, the nucleotide chain or the nucleotide sample is preferably a double-stranded nucleotide. The kind and the preparation method of the nucleotide are the same as those described above.

For example, when the detecting site 480 is an SNP, the position indicated by an arrow 481 is first digested by the first enzyme, and the position indicated by an arrow 482 is digested with the second enzyme. Then, a first adapter 470 binds to the digestion site of the first enzyme, while a second adapter 471 binds to the digestion site of the second enzyme. The double-stranded chain obtained is denatured, and then, the single-strand chain (referred to as "detecting chain") 483 having a phosphoric acid bound to the 5' side of the partial single-stranded before binding is converted into a dumbbell shape 484 and then into a cyclic structure.

Any detection method described above may be used for detection. The complementary chain synthesis-inhibiting structure is not always needed, and, when there is no complementary chain synthesis-inhibiting structure, the cyclic structure may be detected by electrophoresis or mass spectrometry.

After the cyclic structure is formed, or after the dumbbell shape is formed, the undesirable single-stranded nucleotide may be digested by digestion with a desirable enzyme. In this way, it is possible favorably to obtain high detection sensitivity and/or high operability in the subsequent detection and/or operation.

When there is a complementary chain synthesis-inhibiting structure between the tag and the primer sequence, growth of the complementary chain is terminated at the inhibition position. Thus, favorably, there is no undesirable long chain product generated, when the presence of the cyclic structure is reflected to other nucleotides.

Alternatively, when there is a complementary chain synthesis-inhibiting structure between the tag and the primer sequence, growth of the complementary chain is terminated at the inhibition position. Thus, after termination of the growth of the complementary chain, it is possible to obtain a product having a minimum needed length during tag amplification by in-vitro transcription by using a T7 promoter.

The present invention thus provides a nucleotide sequence-detecting method lower in running cost and resistant to non-specific reaction.

In addition, thermal cycling may be performed in the period from a single-stranded gap ligation and dumbbell forming, to gap ligation. It is thus possible to form the dumbbell molecule in a greater amount.

Thermal cycling may be performed simultaneously with the steps from formation of the detecting chain to formation of the cyclic structure or with the steps after formation of the detecting chain to formation of the cyclic structure. The term "thermal cycling" means control of the temperature of a reaction system in a particular temperature range in such a manner that it is possible to carry out suitable intramolecular hybridization. It is possible to place a step of thermally denaturing the double-stranded chain periodically and reliably by conversion of the double-stranded nucleotide into a single-strand chain by thermal denaturation during intramolecular reaction of the nucleotide obtained after single-stranded gap ligation synthesis, and advantageously to advance the intramolecular hybridization while preventing the inhibition of intramolecular reaction by reassociation of the double-strand.

4. Kit

In another aspect of the present invention, provided is a detection kit, comprising: a first detecting chain-preparing nucleotide containing a sequence complementary to the first sequence located more to the 3' side of the detection site contained in the nucleotide sample for use in the nucleotide sequence-detecting method according to the present invention; a second detecting chain-preparing nucleotide containing a sequence complementary to the second sequence located more to the 5' side of the detecting site, a complementary chain synthesis-inhibiting structure at the 5' side, and a tag sequence additionally at the 5' side; and a reagent including enzymes, nucleotides, substrates, and a buffer. Also provided is a detection kit, comprising the primers and any other components.

It is possible to perform the nucleotide sequence-detecting method according to the present invention easily with these kits.

5. Other Aspects

The detection method according to the present invention has the following aspects (1) to (16).

(1) a Nucleotide Sequence-Detecting Method, Comprising:

(a) preparing a detecting chain;

(b) conducting intramolecular hybridization of the detecting chain under a condition allowing suitable intramolecular hybridization;

(c) ligating and ring-closing the intramolecularly hybridized detecting chain; and (d) obtaining information on a desirable mutation site and/or detecting site by detecting the cyclic structure obtained by the ligation/ring-closure.

(2) The Method Described in (1), Wherein Obtaining a Detecting Chain (a) Further Comprises:

(i) converting the analyte nucleotide into a single-stranded nucleotide sample;

(ii) preparing first and second detecting chain-preparing nucleotides, wherein the first detecting chain-preparing nucleotide contains a primer sequence complementary to the first sequence located at the 3'-sided position of the detecting site contained in the single-stranded nucleotide sample and a first sequence homologous to the detecting-site sequence located at the 3' side of the mutation site of the single-stranded nucleotide sample connected to the 5' side, the second detecting chain-preparing nucleotide contains an oligonucleotide sequence complementary to the second sequence located at the 5' sided position of the detecting site contained in the single-stranded nucleotide sample, a complementary chain synthesis-inhibiting structure connected to the 3' side thereof, and a second sequence homologous to the detecting-site sequence at the 5' side of the mutation site of the single-stranded nucleotide sample connected to the 3' side thereof, and at least one of the 3' terminal of the first detecting chain-preparing nucleotide and the 5' terminal of the second detecting chain-preparing nucleotide is so modified to bind to each other;

(iii) allowing the nucleotide sample prepared in (i) and the first and second detecting chain-preparing nucleotides prepared in (ii) to hybridize to each other;

(iv) elongating the first detecting chain-preparing nucleotide under a condition allowing suitable elongation; and (v) obtaining a detecting chain by binding the 3' terminal of the elongated first detecting chain-preparing nucleotide and the 5' terminal of the second detecting chain-preparing nucleotide to each other, the hybridization in (b) is intramolecular self-hybridization of the detecting chain obtained in (v) by using the first and second sequences contained in the detecting chain, and the ligation/ring closure in (c) is to obtain a cyclic structure by ligation and ring closure of the 5' terminal of the first sequence and the 3' terminal of the second sequence.

(3) The method described in (2), wherein obtaining the information on the mutation site and/or detecting site comprises:

(i) amplifying the sequences at both terminals of the connecting region containing the detection sequence of the cyclic structure into the complementary chain synthesis-inhibiting structure; and (ii) the desired sequence of the nucleotide sample is detected by detection of the amplification product obtained by the amplification in (i).

(4) The nucleotide sequence-detecting method described in (2) or (3), wherein the first detecting chain-preparing nucleotide contains additionally a first tag sequence between the primer sequence and the first sequence, and the second detecting chain-preparing nucleotide contains additionally a second tag sequence between the complementary chain synthesis-inhibiting structure and the second sequence.

(5) The method described in any one of (2) to (4), further comprising digesting the non-ligated/ring-closed nucleotides after the ligation and ring closure.

(6) The method described in any one of (2) to (5), wherein the modification allowing ligation is phosphorylation of the 5' terminal of the oligonucleotide sequence of the second detecting chain-preparing nucleotide.

(7) The method described in (1), wherein obtaining a detecting chain (a) further comprises:

(i) preparing a double-stranded nucleotide sample;

(ii) cleaving the double-stranded nucleotide sample with first and second restriction enzymes;

(iii) binding a first adapter to the first restriction enzyme cleavage site and a second adapter to the second restriction enzyme cleavage site, wherein the first adapter has an adapter terminal phosphorylated at one single-stranded 5'-terminal for binding to the first restriction enzyme cleavage site and a sequence complementary to the 3' side of the detecting region for intramolecular hybridization at the 3'-terminal side of the nucleotide sample of the first chain, the second adapter contains an adapter terminal phosphorylated at one single-stranded 5'-terminal for binding to the second restriction enzyme cleavage site and a chain synthesis-inhibiting structure complementary to the one single-strand chain, and the phosphorylated 5'-terminal-sided sequence of the chain is a sequence complementary to the 5'-sided sequence of the detecting region of the nucleotide sample; and (iv) obtaining the detecting chain from the double-stranded chain obtained in (iii).

(8) The method described in any one of (1) to (7), further comprising digesting non-ligated/ring-closed nucleotides after the ligation and ring closure.

(9) The method described in any one of (1) to (8), further comprising amplifying at least part of the cyclic structure obtained by the ligation and ring closure in (c).

(10) The method described in (9), wherein the amplification is RNA synthesis by in-vitro transcription with an RNA polymerase.

(11) The method described in any one of (1) to (10), wherein thermal cycling of changing the reaction temperature periodically is performed multiple times in the steps of intramolecular hybridization and ligation and ring closure.

(12) The method described in (7) or (8), wherein the step (d) is performed by detection of hybridization between the amplification product and a DNA microarray.

(13) The method described in (1), wherein the step (d) is performed by indirectly detecting the amplification product, by allowing hybridization to the amplification product and hybridization of a nucleotide carrying a detectable label to the amplification product, and detecting the detectable label.

(14) The method described in (7) or (8), wherein the step (d) is performed by mass spectrometry of the amplification product.

(15) The method described in (7) or (8), wherein the step (d) is performed by electrophoresis of the amplification product.

(16) A detection kit for use in the method described in any one of (1) to (15), comprising a reagent including part or all of enzymes, substrates, a buffer, and a detection microarray.

As shown in the aspects of the present invention above, the present invention provides a method of allowing low-cost operation and resistant to nonspecific reaction, without need for addition of a great excess amount of probe nucleotides with respect to the analyte nucleotide in detecting a nucleotide obtained by ligation reaction of a probe.

EXAMPLES

Example 1

An example of a protocol for SNP typing is shown below, and the detection results obtained in the protocol will be described.

Hereinafter, the protocol will be described.

1. Design of Probe and Priming Sequences

The nucleotide sequence of the target SNP was obtained from the Japanese SNP Database JSNP (http://snp.ims.u-tokyo.ac.jp/index_ja.html) available from the Institute of Medical Science, Univ. Tokyo. The accession number of the SNP is IMS-JST 164838, and the sequence around the SNP #3 is shown in Table 1.

TABLE 1

| Sequence around SNP | | | |
|---|---|---|---|
| | | Allele | Sequence around SNP |
| SNP#3 | IMS-JST164838 | G/A | ACGAGATAGC G/A CAGGTCAGGT |

Hereinafter, the SNP will be called simply SNP 003. The detected sample was a human genomic DNA extracted from a human peripheral blood cell line available from Human Science Research Resources Bank of the Human Health Sciences Foundation (http://www.jhsf.or.jp/bank/psc.html).

The sample numbers were PSCDA 0503, PSCDA 0328, PSCDA 0719, PSCDA 0785, PSCDA 0415, PSCDA 0716, PSCDA 0693, and PSCDA 0117, and the eight samples were analyzed. Table 2 shows the sequencing result of the samples by the Sanger's method; PRISM 3100 Genetic Analyzer manufactured by Applied Biosystems was used for sequencing and sequencer-outputting waveform analyzer software Namihei from Mitsui Knowledge Industry for identification of the alleles of each SNP.

TABLE 2

Results of SNP typing of samples by another method

| | Sample No. | | | | | | | |
|---|---|---|---|---|---|---|---|---|
| | 503 | 328 | 719 | 785 | 415 | 716 | 693 | 117 |
| SNP003 | G/A | G/G | G/A | A/A | A/A | G/A | G/A | G/G |

Hereinafter, the method of processing respective genome samples will be described.

2. Detection Experiment (1) Phosphorylation of Probe

LSO primers of first PCR were phosphorylated. 5'-terminal phosphorylation of the ASO primer on the chain used for detection is needed in the ligation or gap ligation in the reaction 3. The following reaction solution was prepared for reaction.

T4 polynucleotide kinase (Takara Bio Inc.) 20 units
T4PK buffer (ditto) 1× (final concentration)
LSO primer 5 μm (final concentration)
ATP 1 mM (final concentration)
Total amount (diluted with ultrapure water as needed) 50 μL.

Temperature condition (PTC-200 manufactured by MJ Research)
1. 37° C. for 60 minutes
2. 95° C. for 15 minutes
3. 10° C. hold.

In this manner, the ASO primers were phosphorylated.

(2) First PCR

In detection in the Example, the region containing the target SNP was first amplified by PCR from 5 ng of genomic DNA. The operation was performed in the following procedure.

The compositions of the solutions used in the PCR reaction are shown below, and the priming sequence is shown in Table 3.

TABLE 3

Sequences for detecting
Underlined parts are artificial sequence

| Name of sequence | Sequence (5'→3') |
|---|---|
| ASO primer (A allele side) | ACAGGTCAGGTGGGAGGTTTTTCTAGAGTGGACACGGAATTGCTCTGCTCTTGTAAGTCTGGGATGCTTTCCT |
| ASO primer (G allele side) | GCAGGTCAGGTGGGATGTTTTGTATTCAAGCGGTGGTAATTGCTCTGCTCTTGTAAGTCTGGGATGCTTTCCT |
| LSO Primer | GCTATCTCGTCAGACGCAGATTCATTGGTCAGAGAACAAGGTGTCAGACATACCCTCTTTTTGGAGATTTCCTGTTCC |
| MT (A allele side) | CCGTGTCCACTCTAGAAAAACCT |
| MT (G allele side) | ACCACCGCTTGAATACATAAAACAT |
| LT | TGTTCTCTGACCAATGAATCTGC |
| Detecting probe | GCAGATTCATTGGTCAGAGAACA |

The priming sequence was designed by using Visual OMP available from U.W. DNA software. Multiplex PCR was performed. ASO and LSO primers were mixed in the number needed for the SNPs. The sequence around SNP 003 was amplified.

PrimeStar (Takara Bio Inc.) 0.025 U/μL (final concentration)
PrimeStar buffer (ditto) 1× (final concentration)
dNTP 200 μm each
Template 5 ng/10 μL
ASO primer 0.1 μm each
LSO primer 0.2 μm
Total amount (diluted with ultrapure water as needed) 10 μL.

Temperature cycle (PTC-200 manufactured by MJ Research)
1. 98° C. for 10 seconds
2. 68° C. for 60 seconds (1 and 2 for 5 cycles)
3. 98° C. for 10 seconds
4. 72° C. for 90 seconds (3 and 4 for 40 cycles)
5. 10° C. hold.

In this manner, 10 μL of a genome amplification solution was obtained.

2. Ligation

Part of the PCR product was separated and subjected to ring-closing ligation reaction. In the Example, the smoothing reaction was eliminated, because a polymerase that seldom connects an adenine base to the terminal by the PCR 1 was used. If the smoothing reaction is needed, an enzyme having an exonuclease activity in the direction of 3'→5' on a single-stranded nucleotide and no activity on a double-stranded chain is used favorably.

The ring-closing ligation is performed in the following solution.

Taq ligase (New England Biolab) 4 U
Taq ligase buffer (ditto) 1× (final concentration)
First PCR product 1 μL
Ultrapure water, until final solution volume
Total volume (diluted with ultrapure water as needed) 10 μL.

Temperature condition (in PTC-200 manufactured by MJ Research)
1. 95° C. for 60 seconds
2. 65° C. for 60 minutes
3. 10° C. hold.

In this way, the LSO and ASO primers with their corresponding SNP alleles deleted were ring-closed intramolecularly, while nucleotides other than those remained as they were single-stranded.

3. Digestion Reaction

The nucleotides remaining as straight chain molecules in the ligation reaction were decomposed. The nucleotides were decomposed by using a KOD polymerase having an exonuclease activity from Toyobo at high temperature. The composition of the reaction solution is shown below:

Ligation product 2.5 μL
KOD polymerase (Toyobo) 0.2 μL/10 μL
KOD buffer #2 (ditto) 1× (final concentration)
Total amount (diluted with ultrapure water as needed) 10 μL.

The reaction was performed at sufficiently high temperature to make the nucleotide have a single-strand-chain structure.

Temperature condition (in PTC-200 manufactured by MJ Research)
1. 74° C. for 30 minutes
2. 10° C. hold.

In this way, the terminals of most of the single-stranded nucleotides were decomposed.

4. Second PCR

Two kinds of MT's fluorescent-labeled respectively with Cy3 and Cy5 (represents a complementary chain) and LT were used as primers in PCR. PCR proceeds only with the closed-ring molecule. The composition of the solution is shown below. The fluorescent dye-modified side of the primer was in an amount 10 times larger than that of the counterpart, for asymmetric PCR.

Titanium Taq (Becton Dickinson) 1× (final concentration)
PrimeStar buffer (Takara Bio Inc.) 1× (final concentration)
dNTP 200 μm each
Smoothed product 1 μL
LT primer 0.01 μm (final concentration)
Cy3-rMT and Cy5-rMT' primers 0.1 μm each (final concentration)
Total amount (diluted with ultrapure water as needed) 20 μL.

The temperature cycle was as follows:
Temperature cycle (in PTC-200 manufactured by MJ Research)
1. 95° C. for 60 seconds
2. 98° C. for 10 seconds
3. 55° C. for 240 seconds (2 and 3 for 30 cycles)
4. 10° C. hold.

In this way, tags corresponding to the genome SNP alleles were amplified.

5. Detection

The following hybridization solution was prepared, and hybridization was detected on a microarray. The microarray used was prepared by placing SP-BIO from Hitachi on a substrate Hubble Slide available from Takara Bio Inc. Probes were selected as shown in Table 3, and typing was performed by comparing the fluorescence intensities of Cy3 and Cy5.

A capillary array (Jpn. Pat. Appln. KOKAI Publication No. 11-75812) was used for detection. The capillary array is a device for detecting nucleotides by hybridization similar to that on DNA microarray, and the probes were spotted along a groove-like channel. On the capillary array used, probes for tag detection are immobilized in one groove, and the volume of the groove was 20 μL. The capillary is formed on a silicone-rubber plate, and a silicone rubber is adhered to a slide glass carrying probes spotted along a straight line. Holes penetrating to the face opposite to the groove were formed at the both ends of the groove, and thus, even when the face having the groove was bonded to the slide glass side, it was possible to inject the sample solution through the penetration holes. Each solution after second PCR was injected therein and allowed to hybridize.

Formamide 15% (final concentration)
0.5×SSC+0.1% SDS
EDTA 1 mM
Second PCR product 10 μL
Total amount 20 μL.

The capillary array was placed in a dark place, placed on a hot plate previously heated to 37° C., and left there for hybridization for 60 minutes. Then, the capillary array was washed in the following manner:

1) The hybridization solution was withdrawn with a pipette.
2) 20 μL of washing solution containing 1×SSC and 0.2% SDS was injected immediately after then for preventing drying.
3) The silicone-rubber groove was removed from the slide glass.
4) The slide glass was shaken in a washing solution containing 1×SSC and 0.2% SDS at room temperature for 5 minutes.
5) Then, the slide glass is washed as shaken in 0.1×SSC at room temperature for 10 minutes.
6) The slide glass is dried by air spraying or centrifugation.

Figure 33:
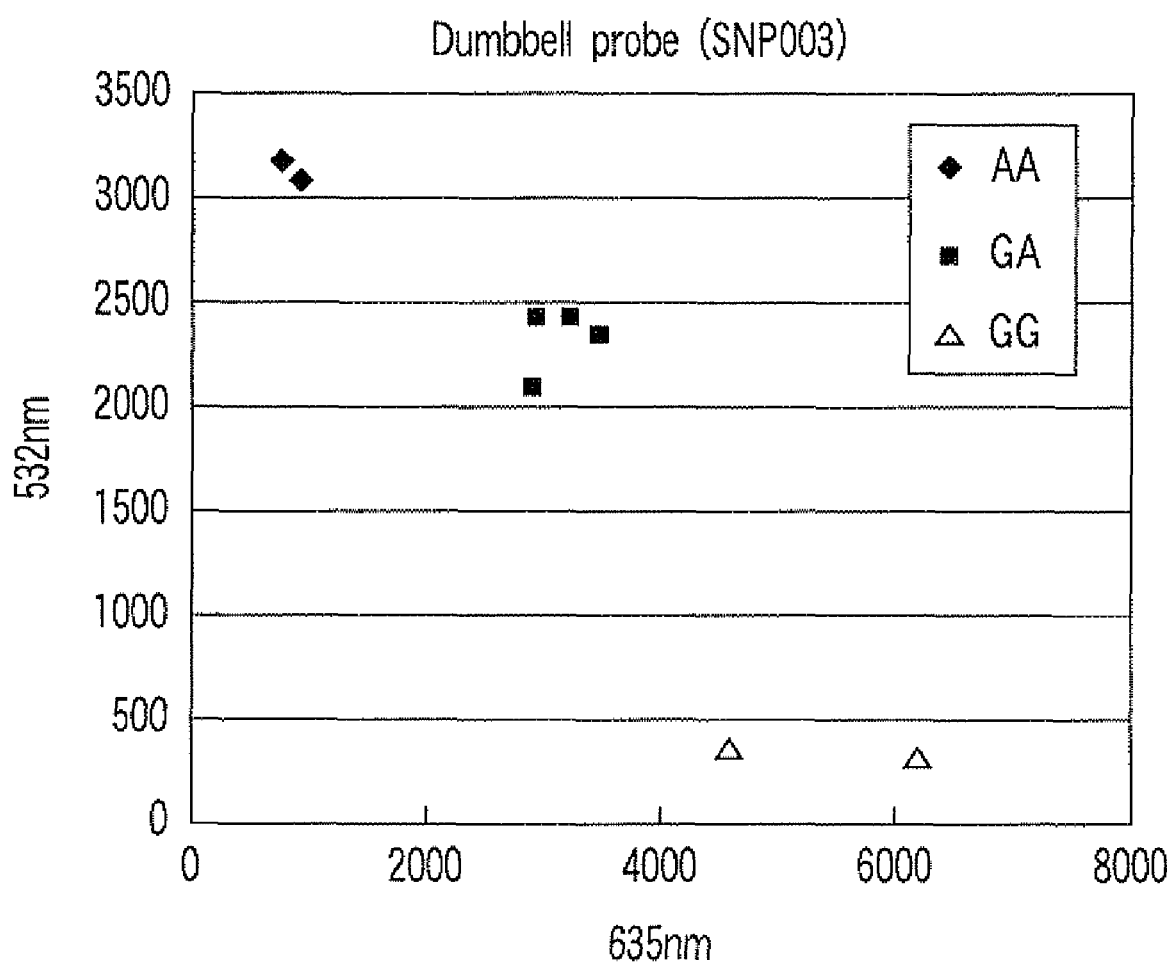
FIG. 33 is a graph showing typing results.

The hybridization reaction was completed in this way, and the hybridization results were analyzed in a microarray scanner, GenePix 4000B manufactured by Axon. The fluorescence images obtained were analyzed with the software attached to the apparatus, and the amount of each allele present in the solution was determined. FIG. 33 is a scatter diagram of fluorescence intensity showing the typing results of the eight samples. The typing results obtained in the present invention agreed well with those by sequencing according to the Sanger's method, indicating that the present invention is an effective detection method.

What is claimed is:

1. A nucleotide sequence-detecting method, comprising:
(a) preparing a nucleic acid sample;
(b) preparing a first intramolecular detecting sequence having a sequence complementary to a first sequence located on a 3'-side of the detecting site contained in the nucleic acid sample and a second intramolecular detecting sequence having a sequence complementary to a second sequence located on a 5'-side of the detecting site, wherein at least one of the 3'-terminal nucleotide of the first intramolecular detecting sequence and the 5'-terminal nucleotide of the second intramolecular detecting sequence is modified in such a manner that they can bind to each other;
(c) preparing a detecting chain containing a sequence of the detecting site by connecting the first intramolecular detecting sequence to the 3' terminal of the nucleic acid sample and the second intramolecular detecting sequence to the 5' terminal;

(d) allowing intramolecular hybridization at two positions of the detecting chain between the first sequence and the first intramolecular detecting sequence and between the second sequence and the second intramolecular detecting sequence;

(e) connecting the 3' terminal of the first intramolecular detecting sequence to the 5' terminal of the second intramolecular detecting sequence directly or indirectly;

(f) obtaining a cyclic structure by the connection (e); and (g) detecting a desired sequence in the nucleic acid sample from the cyclic structure.

2. The nucleotide sequence-detecting method according to claim 1, wherein the connection in (e) between the 5' and 3' terminals of the dumbbell structure occurs by means selected from the group consisting of ligation and gap ligation.

3. The nucleotide sequence-detecting method according to claim 2, wherein formation of the dumbbell structure and the connection thereof in (e) are performed together with thermal cycling under a thermal cycling condition previously determined.

4. The nucleotide sequence-detecting method according to claim 1, wherein the connection in (c) is performed by means selected from the group consisting of PCR by using at least a pair of primers and gap ligation, and restriction-enzyme cleavage and subsequent adapter ligation by using at least a pair of adapters.

5. The nucleotide sequence-detecting method according to claim 1, further comprising digesting un-closed detecting chain with an enzyme after obtaining the cyclic structure in (f).

6. The nucleotide sequence-detecting method according to claim 1, wherein the desired sequence is detected in (g) by detection of the cyclic structure by means selected from the group consisting of DNA microarray, fluorescent beads, electrophoresis and mass spectrometry.

7. The nucleotide sequence-detecting method according to claim 1, wherein the desired sequence is detected in (g) by detection of the cyclic structure by detecting an amplification product obtained by using an elongation reaction using a primer that can detect formation of the connecting region of the cyclic structure.

8. The nucleotide sequence-detecting method according to claim 1, wherein the 5'-terminal of the second intramolecular detecting sequence is phosphorylated.

9. The nucleotide sequence-detecting method according to claim 1, wherein the second intramolecular detecting sequence further includes a primer sequence on the 3' terminal side of the second intramolecular detecting sequence, and the 5' terminal of the first intramolecular detecting sequence is phosphorylated.

10. The nucleotide sequence-detecting method according to claim 1, wherein the connection in (f) is performed by means selected from the group consisting of chemical binding and biochemical binding.

11. The nucleotide sequence-detecting method according to claim 10, wherein the biochemical binding is performed by enzyme-assisted reaction.

12. The nucleotide sequence-detecting method according to claim 1, wherein
the first intramolecular detecting sequence contains a sequence complementary to the first sequence located at the 3' side and a tag sequence previously designed and allocated to carry information about the detection target at the detecting site, and/or
the second intramolecular detecting sequence contains a sequence complementary to the second sequence located at the 5' side of the detecting site and additionally a tag sequence previously designed and allocated to carry information about the detection target at the detecting site.

13. The nucleotide sequence-detecting method according to claim 1, wherein the detecting step is performed by a method selected from the group consisting of SNP detection, gene expression measurement, methylation detection, and detection of deletion, insertion, substitution and microsatellite.

14. A nucleotide mutation-analyzing method, comprising:
(a) preparing a duplicated chain having a sequence that is the same as a nucleic acid analyte having a mutation site and connecting a first and a second fragment to 3' and 5' terminals of the duplicated chain to obtain a detecting chain, the first fragment having a sequence complementary to the mutation site and the region around the mutation site on the nucleic acid analyte the duplicated chain or to the region around the mutation site on the nucleic acid analyte,
wherein the sequences of the first fragment and the second fragment
are different from each other, and the sequence of the first fragment or the second fragment includes a sequence complementary to the sequence of the mutation site on the nucleic acid analyte;
(b) making hybridizations at two regions on the detecting chain to form a dumbbell structure, wherein one region is between the mutation site and the region around the mutation site on the detecting chain and the first fragments in the detecting chain, another region is between the region around the mutation site on the detecting chain and the second fragments in the detecting chain;
(c) connecting the terminals of the detecting chain in the form of dumbbell structure to each other, to form a closed ring-detecting chain, if a desired sequence is present on the mutation site to be detected, through a nucleic acid monomer or a nucleic acid complementary to that of the mutation site or directly;
(d) preparing a fragment having a sequence containing the connecting region of the closed ring-detecting chain or its complementary chain sequence, or both of them; and
(e) analyzing a nucleotide mutation by detecting presence of the sequence containing the connecting region of the prepared closed ring-detecting chain or its complementary sequence.

15. The method according to claim 14,
wherein in step (a), the preparing and connecting are performed by means of PCR to obtain a PCR product as duplicated chains containing the first single-stranded chain having same sequence as that of the nucleic acid analyte and a second single-stranded chain complementary to the first single-stranded chain, the PCR is carried out by using a pair of primers including at least one first primer and at least one second primer,
the first primer includes a first priming sequence and a first probe sequence, the first priming sequence located on a 3' terminal side of the first primer, and the first probe sequence located on a 5' terminal side of the first primer, and the second primer includes a second priming sequence and a second probe sequence, the second priming sequence located on a 3' terminal side of the second primer and a second probe sequence on a 5' terminal side of the second primer,
the first probe sequence is same sequence as a partial sequence at 3' side of the mutation side on the nucleic acid analyte, the second probe sequence is same sequence as a partial sequence at 3' side of the mutation site, and a 5' terminal of the second primer is phosphorylated.

16. The method according to claim 15 wherein the preparing a sequence in (d) is performed by further PCR amplification for the closed ring-detecting chain obtained in (c) as a template to give an amplification product containing the sequence of the mutation site to be detected contained in the closed ring-detecting chain and sequences contained in the same closed ring-detecting chain, and the further PCR amplification carried out with a first primer and a second primer, wherein the analyzing a nucleic acid mutation in (e) is performed by detecting the amplification product obtained by the further PCR amplification.

17. The method according to claim 16, wherein the first primer used in the PCR amplification has an identifiable first chemical labeling substance and the second primer has an identifiable second chemical labeling substance, the PCR amplification product obtained is allowed to react with first particles carrying an antibody to the first chemical labeling substance and second particles carrying an antibody to the second chemical labeling substance, and the mutation to be detected in the nucleic acid analyte is analyzed by detecting the particle aggregation caused by the reaction.

18. The method according to claim 16, wherein first and/or second primers previously labeled with a fluorescent dye are used in the amplification, the amplification product obtained is allowed to hybridize to a DNA microarray carrying a probe for capturing the amplification product, and the mutation to be detected in the nucleic acid analyte is analyzed by detecting fluorescence on the DNA microarray.

19. The method according to claim 16, wherein for the amplification for a part of the closed ring-detecting chain, a plurality of first primers are prepared according to the number of types of the mutation to be detected, each of the plurality of first primers further has an artificially designed sequence between the priming sequence and the probe sequence, the artificially designed sequence contained in each of the plurality of first primers contain a recognizing sequence, the recognizing sequences contained in the plurality of first primers are different from each other which respectively correspond to the mutation types of the mutation site, and each of the artificially designed sequences are respectively labeled with one of a plurality of identifiable fluorescent dyes, the artificially designed sequences are pre-selected so that the multiple identifiable fluorescent dyes are correlated with the mutation types possibly observed at the same mutation site, the artificially designed sequences respectively further contain hybridizing sequences to hybridize to probes immobilized on a microarray respectively, wherein the hybridizing sequences are designed to have a sequence common to all of multiple mutation types possibly observed at the same mutation site on the nucleic acid analyte, and the mutation to be detected in the nucleic acid analyte is analyzed by detecting the fluorescent dyes in multiple colors on a DNA microarray.

20. The method according to claim 16, wherein first and/or second primers previously labeled with a fluorescent dye are used in the PCR amplification for a part of the closed ring-detecting chain to obtain a further PCR amplification product, the PCR amplification product obtained is allowed to hybridize to fluorescent-identifiable particles, each carrying a probe for capturing one kind of artificially designed sequence, and the mutation to be detected in the nucleic acid analyte is analyzed, based on the information on the fluorescence from the fluorescent particle and the further PCR amplifying product.

21. The method according to claim 20, wherein the fluorescence particle is selected from the group consisting of bead and quantum dot containing a fluorescent dye and bead containing multiple kinds of quantum dots.

22. The method according to claim 15, wherein a base bound to a 3' terminal of an first amplification product of (a) is eliminated and the terminal is smoothed after the amplification in (a).

23. The method according to claim 15, further comprising decomposing straight chain nucleic acid molecules other than the closed ring-detecting chain partially or completely.

24. The method according to claim 15, wherein the first and second primers further have an artificially designed sequence usable for identification and/or amplification between the priming sequence and the probe sequence.

25. The method according to claim 15, wherein: the first and second primers further have an artificially designed sequence between the priming sequence and the probe sequence; the artificially designed sequence contains a recognizing sequence having one or more sequences corresponding to the number of a site and/or type of the mutation to be detected; an artificially sequence contained in the first primer is selected corresponding to the mutation type in the mutation site; and an artificially designed sequence contained in the second primer is selected corresponding to the mutation site.

26. The method according to claim 15, wherein: in the first single-stranded chain, the 3' and 5' terminals of the first single-stranded chain hybridize intramolecularly to the mutation site or the region around the mutation site to form a dumbbell structure.

27. The method according to claim 26, wherein the closed ring-detecting chain is formed from the detecting chain in the form of dumbbell structure by action of a ligase.

28. The method according to claim 26, wherein the closed ring-detecting chain is formed from the detecting chain in the form of dumbbell structure by complementary chain synthesis by a polymerase and ligation by a ligase.

29. The method according to claim 26, wherein the closed ring-detecting chain is formed from the detecting chain in the form of dumbbell structure by action of a ligase in the presence of a 5'-terminal-phosphorylated fragment having a sequence complementary to that of mutation site and a region of a single chain of the dumbbell structure.

30. The method according to claim 29, wherein the mutation to be detected is a single-nucleotide mutation.

31. The method according to claim 15, wherein the mutation to be detected is a single-nucleotide mutation and the first primer contains a first probe sequence which is the same sequence as a sequence of the first single-stranded mutation site and part of the sequence close to the 3' end of the mutation site on the 5'-terminal side of the first primer; and the second primer contains a second probe sequence which is the same sequence as a sequence of part of the sequence close to the 3' end of the second single-strand chain mutation site on the 5' end of the second primer.

32. A nucleotide mutation-analyzing method, comprising:
(a) carrying out amplification for a nucleic acid analyte using primers to obtain an amplification product as duplicated chains containing a first detecting chain having the same sequence as that of the nucleic acid analyte and a second detecting chain complementary to the first single-stranded chain, wherein
said primers include first and second primers for amplification of a sequence containing the mutation sequence of the nucleic acid analyte,
the first primer includes a first priming sequence and a first probe sequence, the first priming sequence located on a 3' terminal side of the first primer, and the first probe sequence located on a 5' terminal side of the first primer, and the second primer includes a second priming sequence and a second probe sequence, the second priming located on a 3' terminal side of the second primer and the second probe sequence on a 5' terminal side of the second primer,
the first probe sequence consists of a sequence which is the same as that of the mutation side and a further sequence which is the same as that of sequence located between the 3' side of the mutation side and the 5' side of a site for binding of the first priming sequence on the nucleic acid analyte, the second probe sequence is complementary to a sequence located at between 5' side of the mutation site on the nucleic acid analyte and 3' side of a site for binding of the second priming sequence on the nucleic acid analyte, and the 5' terminal of the second primer is phosphorylated;
(b) converting the amplification product obtained in step (a) into the first detecting chain and the second detecting chain;
(c) making the first detecting chain and/or the second detecting chain hybridize intramolecularly to form a dumbbell structure, and if a desired sequence is present on the mutation site to be detected, from the dumbbell structure by ring-closure reaction to give a closed ring-detecting chain; and
(d) the mutation to be detected in the nucleic acid analyte is analyzed by detecting the difference in conformation between the closed ring-detecting chain and un-closed first and/or second detecting chain.

33. The method according to claim 32, wherein the difference in conformation between the closed-ring nucleic acid molecule and the non-ring-closed straight nucleic acid molecules is detected by an electrophoretic method.

34. A nucleotide sequence-detecting method, comprising:
(a) preparing a nucleic acid sample, wherein the nucleic acid sample contains a detecting site, a first sequence located on a 3' side of the detecting site, and a second sequence located on a 5' side of the detecting site;
(b) preparing a first detecting chain-preparing nucleic acid and a second detecting chain-preparing nucleic acid, wherein
the first detecting chain-preparing nucleic acid contains a first probe sequence located on a 5' terminal side of the first detecting chain-preparing nucleic acid and a primer sequence located on a 3' terminal side of the first detecting chain-preparing nucleic acid, the first probe sequence being same sequence as that of the first sequence of the nucleic acid sample, the primer sequence complementary to that of a region located in a 3' side of the first sequence of the nucleic acid sample,
the second detecting chain-preparing nucleic acid contains a second probe sequence located on a 3' terminal side of the second detecting chain-preparing nucleic acid and a oligonucleotide sequence on a 5' terminal side of the second detecting chain-preparing nucleic acid, a 3' terminal of the second probe sequence having a complementary chain synthesis-inhibiting structure,
the second probe sequence being same sequence as that of the second sequence on the nucleic acid sample, the oligonucleotide sequence complementary to that of a region located in a 5'-side of the second sequence of nucleic acid sample,
wherein at least one of the 5'-terminal nucleotide of the first detecting chain-preparing nucleic acid and the 3'-terminal nucleotide of the second detecting chain-preparing nucleic acid is modified in such a manner that they can bind to each other;
(c) preparing a detecting chain by allowing the primer sequence and the oligonucleotide sequence to hybridize to the nucleic acid sample, allowing elongation reaction of the first detecting chain-preparing nucleic acid with initiation from a 3' terminal of the primer sequence, and allowing ligation reaction between a 3' terminal of the elongated first detecting chain preparing nucleic acid and a 5' terminal of the second detecting chain-preparing nucleic acid;
(d) allowing intramolecular hybridization of the detecting chain at two positions, one position being between a site corresponding to the first sequence and the first probe sequence on the detecting chain, and another position being between a site corresponding to the second sequence and the second probe sequence on the detecting chain detecting chain preparing nucleotides to form a dumbbell structure;
(e) forming a closed ring-detecting chain by connecting between 3' and 5' terminals of the detecting chain in the form of dumbbell structure;
(f) amplifying a nucleic acid having the sequence containing the connecting region of the closed ring-detecting chain; and
(g) detecting the detecting-site sequence in the nucleic acid sample by detecting the amplification product obtained by amplification (f).

35. The method according to claim 34, wherein the connecting in (e) is performed by means selected from the group consisting of ligation and gap ligation.

36. The method according to claim 35, wherein the steps of intramolecular hybridization and ligation for the connecting are performed together with thermal cycling under a thermal cycling condition previously determined.

37. The method according to claim 34, further comprising digesting non-ring-closed nucleic acid molecules after the step (e).

38. The method according to claim 34, wherein the amplifying of (f) is carried out by PCR.

39. The method according to claim 34, wherein the amplifying of (f) is carried out by RNA synthesis by in-vitro transcription with an RNA polymerase.

40. The method according to claim 34, wherein the modification is phosphorylation of a nucleic acid molecule.

41. The method according to claim 34, wherein the step (g) is performed by detecting hybridization between the amplification product and a DNA microarray.

42. The method according to claim 34, wherein the step (g) is performed by indirect detection of the amplification product by means selected from the group consisting of hybridization to the amplification product, hybridization of the amplification product to a nucleic acid carrying a detectable label, and detection of the detectable label.

* * * * *